US010494386B2

(12) United States Patent
Yaghi et al.

(10) Patent No.: US 10,494,386 B2
(45) Date of Patent: Dec. 3, 2019

(54) MESOSCOPIC MATERIALS COMPRISED OF ORDERED SUPERLATTICES OF MICROPOROUS METAL-ORGANIC FRAMEWORKS

(71) Applicant: The Regents of the University of California, Oakland, CA (US)

(72) Inventors: Omar M. Yaghi, Berkeley, CA (US); Kyungmin Choi, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/126,569

(22) PCT Filed: Mar. 17, 2015

(86) PCT No.: PCT/US2015/021090
§ 371 (c)(1),
(2) Date: Sep. 15, 2016

(87) PCT Pub. No.: WO2015/142944
PCT Pub. Date: Sep. 24, 2015

(65) Prior Publication Data
US 2017/0081346 A1 Mar. 23, 2017

Related U.S. Application Data

(60) Provisional application No. 61/955,084, filed on Mar. 18, 2014.

(51) Int. Cl.
| | |
|---|---|
| *C07F 7/00* | (2006.01) |
| *B01J 31/12* | (2006.01) |
| *B01J 20/30* | (2006.01) |
| *B01J 20/22* | (2006.01) |
| *B01J 20/28* | (2006.01) |

(52) U.S. Cl.
CPC ............. *C07F 7/003* (2013.01); *B01J 20/226* (2013.01); *B01J 20/2809* (2013.01); *B01J 20/3085* (2013.01); *B01J 31/123* (2013.01); *B01D 2253/204* (2013.01); *Y02C 10/08* (2013.01)

(58) Field of Classification Search
CPC .... C07F 7/00; B01J 31/12; B01J 20/30; B01J 20/22
See application file for complete search history.

(56) References Cited

U.S. PATENT DOCUMENTS

| | | |
|---|---|---|
| 2,684,967 A | 7/1954 | Berg |
| 4,532,225 A | 7/1985 | Tsao |
| 5,064,804 A | 11/1991 | Soo |
| 5,160,500 A | 11/1992 | Chu |
| 5,208,335 A | 5/1993 | Ramprasad |
| 5,617,467 A | 4/1997 | Bacher et al. |
| 5,648,508 A | 7/1997 | Yaghi |
| 5,733,505 A | 3/1998 | Goldstein |
| 5,779,904 A | 7/1998 | Ruderman |
| 6,479,447 B2 | 11/2002 | Bijl |
| 6,501,000 B1 | 12/2002 | Stibrany |
| 6,617,467 B1 | 9/2003 | Mueller |
| 6,624,318 B1 | 9/2003 | Mueller |
| 6,686,428 B2 | 2/2004 | Zhang |
| 6,893,564 B2 | 5/2005 | Mueller |
| 6,929,679 B2 | 8/2005 | Mueller |
| 6,930,193 B2 | 8/2005 | Yaghi |
| 7,196,210 B2 | 3/2007 | Yaghi |
| 7,202,385 B2 | 4/2007 | Mueller |
| 7,229,943 B2 | 6/2007 | Gibson |
| 7,279,517 B2 | 10/2007 | Mueller |
| 7,309,380 B2 | 12/2007 | Mueller |
| 7,343,747 B2 | 3/2008 | Mueller |
| 7,411,081 B2 | 8/2008 | Mueller |
| 7,524,444 B2 | 4/2009 | Hesse |
| 7,582,798 B2 | 9/2009 | Yaghi |
| 7,637,983 B1 | 12/2009 | Liu |
| 7,652,132 B2 | 1/2010 | Yaghi |
| 7,662,746 B2 | 2/2010 | Yaghi |
| 7,799,120 B2 | 9/2010 | Yaghi |
| 7,815,716 B2 | 10/2010 | Mueller |
| 8,343,260 B2 | 1/2013 | Omary |
| 8,480,955 B2 | 7/2013 | Yaghi |
| 8,501,150 B2 | 8/2013 | Schubert |
| 8,518,264 B2 | 8/2013 | Kiener |
| 8,524,932 B2 | 9/2013 | Leung |
| 8,709,134 B2 | 4/2014 | Yaghi |
| 8,735,161 B2 | 5/2014 | Yaghi |
| 8,742,152 B2 | 6/2014 | Yaghi |
| 9,078,922 B2 | 7/2015 | Yaghi |
| 2003/0004364 A1 | 1/2003 | Yaghi |
| 2003/0078311 A1 | 4/2003 | Muller |
| 2003/0148165 A1 | 8/2003 | Muller |
| 2003/0222023 A1 | 12/2003 | Mueller |
| 2004/0081611 A1 | 4/2004 | Muller |
| 2004/0225134 A1 | 11/2004 | Yaghi |
| 2004/0249189 A1 | 12/2004 | Mueller |
| 2004/0265670 A1 | 12/2004 | Muller |
| 2005/0004404 A1 | 1/2005 | Muller |
| 2005/0014371 A1 | 1/2005 | Tsapatsis |
| 2005/0124819 A1 | 6/2005 | Yaghi |
| 2005/0154222 A1 | 7/2005 | Muller |
| 2005/0192175 A1 | 9/2005 | Yaghi |

(Continued)

FOREIGN PATENT DOCUMENTS

| | | |
|---|---|---|
| CN | 1910191 A | 2/2007 |
| CN | 101270094 A | 9/2008 |

(Continued)

OTHER PUBLICATIONS

Nanocrystal—Wikipedia, 2018, https://en.wikipedia.org/wiki/Nanocrystal.*

(Continued)

*Primary Examiner* — Sun Jae Yoo
(74) *Attorney, Agent, or Firm* — Gavrilovich, Dodd & Lindsey LLP

(57) ABSTRACT

The disclosure provides for MOF heterolites comprised of ordered superlattices of MOFs, the manufacture thereof, and the use of the MOF heterolites for various applications, such as gas separation and/or storage, catalysis, light harvesting, and meta-materials.

20 Claims, 26 Drawing Sheets

(56) References Cited

U.S. PATENT DOCUMENTS

| | | |
|---|---|---|
| 2006/0057057 A1 | 3/2006 | Muller |
| 2006/0135824 A1 | 6/2006 | Mueller |
| 2006/0154807 A1 | 7/2006 | Yaghi |
| 2006/0185388 A1 | 8/2006 | Muller |
| 2006/0252641 A1 | 11/2006 | Yaghi |
| 2006/0252972 A1 | 11/2006 | Pilliod |
| 2006/0287190 A1 | 12/2006 | Eddaoudi |
| 2007/0068389 A1 | 3/2007 | Yaghi et al. |
| 2007/0202038 A1 | 8/2007 | Yaghi |
| 2007/0217982 A1 | 9/2007 | Wright |
| 2007/0248575 A1 | 10/2007 | Connor |
| 2008/0017036 A1 | 1/2008 | Schultink |
| 2008/0184883 A1 | 8/2008 | Zhou |
| 2008/0190289 A1 | 8/2008 | Muller |
| 2009/0155588 A1 | 6/2009 | Hesse |
| 2009/0183996 A1 | 7/2009 | Richter |
| 2009/0216059 A1 | 8/2009 | Reyes |
| 2009/0247654 A1 | 10/2009 | Rajendran |
| 2010/0069234 A1 | 3/2010 | Willis |
| 2010/0132549 A1 | 6/2010 | Yaghi |
| 2010/0143693 A1 | 6/2010 | Yaghi |
| 2010/0186588 A1 | 7/2010 | Yaghi |
| 2010/0286022 A1 | 11/2010 | Yaghi |
| 2011/0015388 A1 | 1/2011 | Youngblood |
| 2011/0137025 A1 | 6/2011 | Yaghi |
| 2011/0282067 A1 | 11/2011 | Li |
| 2011/0282071 A1 | 11/2011 | Shi |
| 2012/0028846 A1 | 2/2012 | Yaghi |
| 2012/0031268 A1 | 2/2012 | Yaghi |
| 2012/0115961 A1 | 5/2012 | Hafizovic et al. |
| 2012/0130113 A1 | 5/2012 | Yaghi |
| 2012/0133939 A1 | 5/2012 | Yaghi |
| 2013/0047849 A1 | 2/2013 | Zhang |
| 2013/0095996 A1 | 4/2013 | Buelow et al. |
| 2013/0096210 A1 | 4/2013 | Yaghi |
| 2014/0037944 A1 | 2/2014 | Dichtel |
| 2014/0148596 A1 | 5/2014 | Dichtel |

FOREIGN PATENT DOCUMENTS

| | | |
|---|---|---|
| DE | 102005023856 A1 | 11/2006 |
| DE | 102005054523 A1 | 5/2007 |
| EP | 1070538 A2 | 1/2001 |
| EP | 1674555 A1 | 6/2006 |
| JP | 2007534658 A | 11/2007 |
| JP | 2011-520592 A | 7/2011 |
| JP | 2013-512223 A | 4/2013 |
| JP | 2013-519687 A | 5/2013 |
| KR | 20100055350 A | 5/2010 |
| WO | 9905151 A1 | 2/1999 |
| WO | 03035717 A1 | 5/2003 |
| WO | 2004101575 A2 | 11/2004 |
| WO | 2006047423 A2 | 5/2006 |
| WO | 2006072573 A2 | 7/2006 |
| WO | 2006110740 A2 | 10/2006 |
| WO | 2006116340 A1 | 11/2006 |
| WO | 2006122920 A1 | 11/2006 |
| WO | 2006125761 A2 | 11/2006 |
| WO | 2007007113 A2 | 1/2007 |
| WO | 2007054581 A2 | 5/2007 |
| WO | 2007098263 A2 | 8/2007 |
| WO | 2007101241 A2 | 9/2007 |
| WO | 2007111739 A2 | 10/2007 |
| WO | 2007118843 A1 | 10/2007 |
| WO | 2008091976 A1 | 7/2008 |
| WO | 2008138989 A1 | 11/2008 |
| WO | 2008140788 A1 | 11/2008 |
| WO | 2009020745 A2 | 2/2009 |
| WO | 2009/042802 A1 | 4/2009 |
| WO | 2009056184 A1 | 5/2009 |
| WO | 2009073739 A1 | 6/2009 |
| WO | 2009149381 A2 | 12/2009 |
| WO | 2010056092 A2 | 5/2010 |
| WO | 2010078337 A1 | 7/2010 |
| WO | 2010080618 A2 | 7/2010 |
| WO | 2010083418 A1 | 7/2010 |
| WO | 2010088629 A1 | 8/2010 |
| WO | 2010090683 A1 | 8/2010 |
| WO | 2010148276 A2 | 12/2010 |
| WO | 2010148374 A2 | 12/2010 |
| WO | 2011014503 A1 | 2/2011 |
| WO | 2011038208 A2 | 3/2011 |
| WO | 2011127301 A2 | 10/2011 |
| WO | 2011146155 A2 | 11/2011 |
| WO | 2012012495 A2 | 1/2012 |
| WO | 2012082213 A2 | 6/2012 |
| WO | 2012100224 A2 | 7/2012 |
| WO | 2012106451 A2 | 8/2012 |

OTHER PUBLICATIONS

Nickitas-Etienne, Athina, International Preliminary Report on Patentability and Written Report, PCT/US2015/021090, The International Bureau of WIPO, dated Sep. 29, 2016.

Doonan et al., "Hydrogen Storage in Metal-Organic Frameworks," Annual Merit Rev. Proceedings of DOE Hydrogen Program, May 22, 2009.

Furukawa et al., "Water Adsorption in Porous Metal-Organic Frameworks and Related Materials," J. of the Amer. Chem. Soc., vol. 136, No. 11, pp. 4369-4381, Mar. 3, 2014.

Gandara et al., "Crystallography of Metal-Organic Framworks," IUCRJ, vol. 130, No. 6, pp. 563-570, Oct. 28, 2014.

Kandiah et al., "Post-synthetic modification of the metal-organic framework compound UiO-66," J. of Mater. Chem., vol. 20, No. 44, pp. 9848-9851, 2010.

Lange, Tim, International Search Report, PCT/US2015/021090, European Patent Office, dated Sep. 9, 2015.

Yang et al., "CH4 storage and CO2 capture in highly porous zirconium oxide based metal-organic framworks," Chem. Comm., vol. 48, No. 79, pp. 9831-9833, 2012.

Yaghi, Omar, 'Hydrogen Storage in Metal-Organic Frameworks,' slide presentation to DOE Hydrogen Program 2007 Annual Merit Review, US Department of Energy, on May 15, 2007 at http://www.hydrogen.energy.gov/pdfs/review07/St_10_yaghi.pdf.

Young, Jung Doo, International Search Report and Written Opinion, Application No. PCT/US2010/050170, dated Jun. 8, 2011.

Ashton, Peter R. et al., 'Hydrogen-Bonded Complexes of Aromatic Crown Ethers with (9-Anthracenyl) methylammonium Derivatives' J. Am. Chem. Soc., 1997, 119 (44), pp. 10641-10651.

Carlucci, Lucia etal., 'Polycatenation, polythreading and polyknotting in coordination network chemistry' Coordination Chemistry Reviews 246, 2003, pp. 247-289.

Han, SS et al., 'Improved designs of metal-organic frameworks for hydrogen storage', Angew. Chem Int. Ed., 2007, 46, pp. 6289-6292.

Loeb, 'Rotaxanes as ligands: from molecules to materials', Chem. Soc. Rev., 2007, 36, 226-235.

Moyse, Ellen, International Preliminary Report on Patentability and Written Opinion, dated Nov. 17, 2009, International Application No. PCT/US08/006008.

Nickitas-Etienne, Athina, International Preliminary Report on Patentability and Written Opinion, dated Jan. 19, 2010, International Application No. PCT/US08/70149.

Park, Kyo Sung et al., 'Exceptional chemical and thermal stability of zeolitic imidazolate frameworks,' Proc. Natl. Acad. Sci., Jul. 5, 2006, vol. 103, No. 27, pp. 10186-10191.

Wong-Foy, Ag et al., 'Exceptional H2 Saturation uptake in microporous metal-organic frameworks' J. Am. Chem. Soc, 2006, 128, pp. 3494-3495.

Young, Lee W., International Search Report and Written Opinion, dated Jan. 12, 2009, International Application No. PCT/US08/70149.

Young, Lee W., 'International search Report and Written Opinion,' PCT/US08/06008, United States Patent & Trademark Office, dated Aug. 20, 2008.

Young, Lee W., International Search Report and Written Opinion, dated Dec. 2, 2008, International Application No. PCT/US08/77741.

(56) References Cited

OTHER PUBLICATIONS

Young, Lee W., International Search Report and Written Opinion, dated May 7, 2008, International Application No. PCT/US08/51859.

O'Keefe et al., 'Germanate Zeolites: Contrasting the Behavior of Germanate and Silicate Structures Built from Cubic T8O20 units (T=Si or Ge),' Chem. Eur. J., 1999, 5, 2796-2801.

Phan et al., 'Synthesis, Structure, and Carbon Dioxide Capture Properties of Zeolitic Imidazolate Frameworks,' Acc. Chem. Res 43:58-67 (2009).

Plevert et al., 'A Flexible Germanate Structure Containing 24-Ring Channels With Very Low Framework Density,' J. Am. Chem. Soc, 2001, 123, 12706-12707.

Plevert et al., 'Synthesis and Characterization of Zirconogermanates,' Inorg. Chem., 42:5954-5959 (2003).

Plevert et al., 'Layered Structures Constructed from New Linkages of Ge7(0,OH,F)19 Clusters,' Chem. Mater. 15:714-718(2003).

Rosi et al., 'Advances in the Chemistry of Metal-Organic Frameworks,' CrystEngComm, 2002, 4, 401-404.

Rosi et al., 'Hydrogen Storage in Microporous Metal-Organic Frameworks,' Science 300:1127-1129 (2003); Featured in (1) Chemical & Engineering News magazine, May 19, 2004, and (2) Technology Research News Magazine, May 21, 2003.

Rowsell et al., 'Hydrogen Sorption in Functionalized Metal-Organic Frameworks,' J. Am. Chem. Soc.126: 5666-5667 (2004).

Rowsell et al., 'Strategies for Hydrogen Storage in Metal-Organic Frameworks,' Angew. Chem. Int. Ed. 44: 4670-4679 (2005).

Rowsell et al., 'Gas Adsorption Sites in a Large-Pore Metal-Organic Framework,' Science 309:1350-1354 (2005).

Rowsell et al., 'Effects of Functionalization, Catenation, and Variation of the Metal Oxide and Organic Linking Units on the Low-Pressure Hydrogen Adsorption Properties of Metal-Organic Frameworks,' J. Am. Chem. Soc. 128: 1304-1315(2006).

Spencer et al., 'Determination of the Hydrogen Absorption Sites in Zn4O(1,4-benzenedicarboxylate) by Single Crystal Neutron Diffraction,' Chem. Commun. 3:278-280 (2006); Epub Dec. 6, 2005.

Sudik et al., 'Metal-Organic Frameworks Based on Trigonal Prismatic Building Blocks and the New 'acs' Topology,' Inorg. Chem. 44:2998-3000 (2005).

Sudik et al., 'A Metal-Organic Framework with a Hierarchical System of Pores and Tetrahedral Bbuilding Blocks,' Angew. Chem. Int. Ed. 45:2528-2533 (2006).

Wang et al., 'Colossal Cages in Zeolitic Imidazolate Frameworks as Selective Carbon Dioxide Reservoirs,' Nature 453:207-211 (2008).

Yaghi et al., 'Selective binding and removal of guests in a microporous metal-organic framework,' Nature, Dec. 1995, pp. 703-706, vol. 378.

Yaghi et al., 'Conversion of Hydrogen-Bonded Manganese(II) and Zinc(II) Squarate (C4O42-) Molecules, Chains, and Sheets to 3-D Cage Networks,' J. Chem. Soc, Dalton Trans., 1995, 727-732.

Yaghi et al., 'Conversion of Molecules and Clusters to Extended 3-D Cage and Channel Networks,' Metal Containing Polymeric Materials, C. U. Pittman, C. E. Carraher, B. M. Culbertson, M. Zeldin, J. E. Sheets, Eds., Plenum: New York p.. 219(1996).

Yaghi et al., 'Transformation of Germanium Dioxide to 4-Connected Porous Germanate Net,' J. Am. Chem. Soc, 20:10569-10570(1998).

Yaghi et al., 'Reticular Chemistry and Metal-Organic Frameworks for Clean Energy,' MRS Bulletin 34:682-690 (2009).

Li et al., 'Docking in Metal-Organic Frameworks', Science, 325, 855 (2009).

Zhao, Wei, First Office Action for Chinese Application No. 200880003157.2,The State Intellectual Property Office of the People's Republic of China, dated Aug. 5, 2011.

Burrows et al., 'Post-Synthetic Modification of Tagged MOFs,' Angew. Chem. Int. Ed. 47:8482-8486 (2008).

Banerjee et al., 'High-Throughput Synthesis of Zeolitic Imidazolate Frameworks and Application to CO2 Capture,' Science, 2008, pp. 939-943, vol. 319.

Banerjee et al., 'Control of Pore Size and Functionality in Isoreticular Zeolitic Imidazolate Frameworks and their Carbon Dioxide Selective Capture Properties,' J. Am. Chem. Soc. 131:3875-3877 (2009).

Barman et al., 'Azulene Based Metal-Organic Frameworks for Strong Adsorption of H2,' Chem. Commun. 46:7981-7983 (2010).

Bloch et al., 'Metal Insertion in a Microporous Metal-Organic Framework Lined with 2,2'-Bipyridine' J. Am. Chem. Soc. 132:14382-14384 (2010).

Czaja et al., 'Industrial applications of metal-organic frameworks,' Chemical Society Reviews 38(5):1284-1293 (2009).

Delgado-Friedrichs et al., 'Three-Periodic Nets and Tilings: Regular and Quasiregular Nets,' Acta Cryst. A59:22-27 (2003).

Delgad0-Friedrichs et al., 'Three-Periodic Nets and Tilings: Semiregular Nets,' Acta Cryst. A59:515-525 (2003).

Delgado-Friedrichs et al., 'The CdSO4, Rutile, Cooperate and Quartz Dual Nets: Interpenetration and Catenation,' Solid State Sciences 5:73-78 (2003).

Ockwig et al., 'Reticular Chemistry: Occurrence and Taxonomy of Nets, and Grammar for the Design of Frameworks,' Acc. Chem. Res. 38:176-182 (2005).

Delgado-Friedrichs et al. 'What Do We Know About Three-Periodic Nets?,' J. Solid State Chem. 178:2533-2554 (2005).

Delgado-Friedrichs et al. 'Three-Periodic Nets and Tilings: Edge-Transitive Binodal Structures,' Acta Cryst. 62:350-355 (2006).

Delgado-Friedrichs et al., 'Taxonomy of Periodic Nets and the Design of Materials,' Phys. Chem. 9:1035-1043 (2007).

Deng et al., 'Robust dynamics' Nature Chem. 2:439-443 (2010).

Carlucci et al., 'Nanoporous three-dimensional networks topologically related to cooperite from the self-assembly of copper(I)centres and 1,2,4,5-tetracyanobenzene,' New J. Chem. 23(23):397-401 (1999).

Caskey et al., 'Dramatic Tuning of CO2 Uptake via Metal Substitution in a Coordination Polymer with Cylindrical Pores,' JACS 130(33):10870-10871 (2008).

Caskey et al., 'Selected Applications of Metal-Organic Frameworks in Sustainable Energy Technologies,' Material Matters 4.4:111 (2009).

Chae et al., 'Tertiary Building Units: Synthesis, Structure, and Porosity of a Metal-Organic Dendrimer Framework (MODF-1),' J. Am. Chem. Soc, 2001, 123, 11482-11483.

Chae et al., 'Design of Frameworks with Mixed Triangular and Octahedral Building Blocks Exemplified by the Structure of [Zn4O(TCA)2] Having the Pyrite Topology,' Angew. Chem. Int. Ed. 42:3907-3909 (2003).

Chen et al., 'Cu2(ATC) 6H20: Design of Open Metal Sites in Porous Metal-Organic Crystals (ATC: 1,3,5,7-adamantane tetracarboxylate),' J. Am. Chem. Soc, 2000,122,11559-11560.

Chen et al., 'Interwoven Metal-Organic Framework on a Periodic Minimal Surface with Extra-Large Pores,' Science, 2001, 291,1021-1023: Featured in Chemical and Engineering News, Feb. 21, 2001.

Chen et al., 'High H2 Adsorption in a Microporous Metal-Organic Framework with Open-Metal Sites,' Angew. Chem. Int. Ed. 44:4745-4749 (2005).

Choi et al., 'Heterogeneity within Order in Crystals of a Porous Metal Organic Framework,' J. Am. Chem. Soc. 133:11920-11923 (2011).

Costa et al., 'Chemical Modification of a Bridging Ligand Inside a Metal-Organic Framework while Maintaining the 3D Structure,' Eur. J. Inorg. Chem. 10:1539-1545 (2008).

Cui et al., 'In Situ Hydrothermal Growth of Metal-Organic Framework 199 Films on Stainless Steel Fibers for Solid-Phase Microextraction of Gaseous Benzene Homologues,' Anal. Chem. 81(23):9771-9777 (2009).

Doonan et al., 'Isoreticular Metalation of Metal-Organic Frameworks,' J. Am. Chem. Soc. 131:9492-9493 (2009).

Dugan et al., 'Covalent modification of a metal-organic framework with isocyanates: probing substrate scope and reactivity,' 29:3366-3368 (2008).

Eddaoudi et al., 'Design and Synthesis of Metal-Organic Frameworks with Permanent Porosity,' In Topics in Catalysis, G. A. Somorjai and J. M. Thomas, Eds., 9:105 (1999).

Eddaoudi et al., 'Highly Porous and Stable Metal-Organic Framework: Structure Design and Sorption Properties,' J. Am. Chem. Soc. 121:1391-1397 (2000).

(56) References Cited

OTHER PUBLICATIONS

Eddaoudi et al., 'Porous Metal-Organic Polyhedra: 25 A Cuboctahedron Constructed from Twelve Cu2(C02)4 Paddle-Wheel Building Blocks,' J. Am. Chem. Soc. 123:4368-4369 (2001).
Eddaoudi et al., 'Cu2[o-Br-C6H3(C02)2]2(H20)2-(DMF)8(H20)2: A Framework Deliberately Designed to have the NbO Structure Type,' J. Am. Chem. Soc.124:376-377 (2002).
Furukawa et al., 'Crystal Structure, Dissolution, and Deposition of a 5 nm Functionalized Metal-Organic Great Rhombicuboctahedron,' J. Am. Chem. Soc. 128:8398-8399 (2006).
Furukawa et al., 'Independent verification of the saturation hydrogen uptake in MOF-177 and establishment of a benchmark for hydrogen adsorption in metal-organic frameworks,' J. Mater. Chem. 17:3197-3204 (2007).
Galli et al., 'Adsorption of Harmful Organic Vapors by Flexible Hydrophobic Bis-pyrazolate Based MOFs,' Chem. Mater. 22(5):1664-1672 (2010).
Glover et al., 'MOF-74 building unit has a direct impact on toxic gas adsorption,' J. Chem. Eng. Sci. 66:163-170 (2011).
Gould et al., "Amphidynamic Character of Crystalline MOF-5: Rotational Dynamics of Terephthalate Phenylenes in a Free-Volume, Sterically Unhindered Environment", J. Am. Chem. Soc. 130:3246-3247 (2008).
Huang et al., 'Thermal Conductivity of Metal-Organic Framework 5 (MOF-5): Part II Measurement,' Int. J. Heat Mass Transfer 50:405-411 (2007).
Ingleson et al., 'Framework fractionalization triggers metal complex binding,' Chem. Comm. 23:2680-2682 (2008).
Isaeva et al., 'Metal-organic frameworks-new materials for hydrogen storage,' Russian Journal of General Chemistry 77(4):721-739(2007).
Kaye et al., 'Impact of Preparation and Handling on the Hydrogen Storage Properties of Zn4O(1,4-benzenedicarboxylate)3 (MOF-5),' J. Am. Chem. Soc. 129:14176-14177 (2007).
Li et al., 'Coordinatively Unsaturated Metal Centers in the Extended Porous Framework of Zn3(BDC)36CH30H (BDC=1,4-Benzenedicarboxylate),' J. Am. Chem. Soc, 1998, 120, 2186-2187.
Li et al., 'A metal-organic framework replete with ordered donor-acceptor catenanes,' Chem. Commun. 46:380-382 (2010).
Li et al., 'A Catenated Strut in a Catenated Metal-Organic Framework,' Angew. Chem. Int. Ed. 49:6751-6755 (2010).
Llabres, Francesc X. et al., 'Activity, reusability and shape-sensitivity of a Pd-containing MOF', Journal of Catalysis, Sep. 10, 2007, 250, pp. 294-298.
Milllward et al., 'Metal-Organic Frameworks with Exceptionally High Capacity for Storage of Carbon Dioxide at Room Temperature,' J. Am. Chem. Soc. 127:17998-17999 (2005).
Morris et al., 'Postsynthetic Modification of a Metal-Organic Framework for Stabilization of a Hemiaminal and Ammonia Uptake,' Inorg. Chem. 50:6853-6855 (2011).
Natarajan et al., 'Non-carboxylate based metal-organic frameworks (MOFs) and related aspects,' Current Opinion in Solid State and Materials Science 13(3-4):46-53 (2009).
"IUPAC Gold Book-macrocycle". http://goldbook.iupac.org/M03662.html, accessed Jan. 30, 2014.
Liu., Y., "Dynamic Chirality in Donor-Acceptor Pretzelanes", Journal of Organic Chemistry, 2005, 70, 9334-9344.
"IUPAC Gold Book-cryptand", http://goldbook.iupac.org/C01426.html, accessed Jan. 30, 2014.
Deska, Malgorzata, "Donor-acceptor rotaxanes with tetracationic cyclophane ring", ARKIVOC, 2013, i, 185-242.
Deska, Malgorzata, "Rotaxanes and pseudorotaxanes with threads containing viologen units", ARKIVOC, 2013, i, 66-100.
Chambron, Jean-Claude, "Interlacing molecular threads on transition metals", Pure and Applied Chemistry, 1990, 62(6), 1027-1034.
Niu et al., 'Synthesis and structural characterization of the one dimensional polymers [Rh2(OAc)4(NCPhCN)S, S=CH3COCH3, CH30H, C2H50H, C4H80, and C6H6,' Polyhedron 17(23-24):4079-89 (1998).

Wu et al., 'Structural Study of New Hydrocarbon Nano-Crystals by Energy-Filtered Electron Diffraction,' Ultramicroscopy 98:145-150 (2004).
Pawsey et al., 'Hyperpolarized 129Xe Nuclear Magnetic Resonance Studies of Isoreticular Metal-Organic Frameworks,' Phys. Chem. 111:6060-6067 (2007).
Chan et al., 'Metal-Organic Frameworks of Vanadium as Catalysts for Conversion of Methane to Acetic Acid,' Inorg. Chem. 50:7388-7390 (2011).
Reineke et al., 'From Condensed lanthanide Coordination Solids to Microporous Frameworks having Accessible Metal Sites,' J. Am. Chem. Soc, 1999, 121, 1651-1657.
Reineke et al., 'A Microporosity of Lanthanide-Organic Frameworks,' Angew. Chem. Int. Ed. 38:2590-2594 (1999).
Reineke et al., 'Large Free Volume in Interpenetrating Networks: The Role of Secondary Building Units Exemplified by Tb2(ADB)3[(CH3)2SO]4-16[(CH3)2SO],' J. Am. Chem. Soc, 2000, 122, 4843-4844: Featured in Science Magazine, Editors Choice, Nov. 2000.
Holler et al., 'The first dinitrile frameworks of the rare earth elements: [LnCl3(1,4-Ph(CN)2] and [Ln2Cl6(1,4Ph(CN)2], Ln=Sm, Gd, Tb, Y; Access to novel metal-organic frameworks by solvent free synthesis in molten 1,4-benodinitrile,' Inorganic Chemistry 47(21): 10141-9 (2008).
Jeong et al., 'Asymmetric Catalytic Reactions by NbO-Type Chiral Metal-Organic Frameworks,' Chem. Sci. 2:877-882 (2011).
Li et al., 'Establishing Microporosity in Open Metal-Organic Frameworks: Gas Sorption Isotherms for Zn(BDC) (BDC=1,4-Benzenedicarboxylate),' J. Am. Chem. Soc, 1998, 120, 8571-8572.
Li, Hailian, et al., 'Porous Germanates: Synthesis, Structure and Inclusion Properties of Ge7014.5F2[(CH3)2NH2]3 (H20) 0.86,' J. Am. Chem. Soc, 1998, 120, 8567-8568.
Ling et al., 'A zinc(II) metal-organic framework based on triazole and dicarboxylate ligands for selective adsorption of hexane isomers,' Chem. Comm. 47:7197-7199 (2011).
Song et al., 'Hydrothermal Synthesis and Structural Characterization of Three-dimensional Metal-organic Framework [Zn3(C2H2N3)2(C7H502)4],' Chem. Res. Chinese Universities 25(1):1-4 (2009).
Yang et al. 'Two Novel Triazole-Based Metal-Organic Frameworks Consolidated by a Flexible Dicarboxylate Co-ligand: Hydrothermal Synthesis, Crystal Structure, and Luminescence Properties,' Australian Journal of Chemistry 61 (10):813-820 (2008).
Zhang et al., 'Syntheses, Structures, and Porous/Luminescent Properties of Silver 3-Alkyl-1,2,4-Triazolate Frameworks with Rare 3-Connected Topologies,' Crystal Growth and Design 11:796-802 (2011).
Adkins, Chinessa T. Nonfinal Office Action for U.S. Appl. No. 12/524,205, dated Apr. 17, 2012.
Adkins, Chinessa T. Final Office Action for U.S. Appl. No. 12/524,205, dated Sep. 27, 2012.
Barman et al., 'Incorporation of active metal sites in MOFs via in situ generated ligand deficient metal-linker complexes' Chem. Commun. 47:11882-11884 (Oct. 11, 2011).
Bork, Ana-Marie., International Search Report for PCT/US2011/24671, European Patent Office, dated Nov. 30, 2011.
Chen et al., 'Noncovalently Netted, Photoconductive Sheets with Extremely High Carrier Mobility and Conduction Anisotropy from Triphenylene-Fused Meetal Trigon Conjugates,' In. J. Am. Chem. Soc. 131:7287-7297 (2009).
Choi et al., 'Reversible Interpenetration in a Metal-Organic Framework Triggered by Ligand Removal and Addition,' Angew. Chem. Int. Ed. 51:8791 -8795 (2012).
Coskun et al., 'Metal-Organic Frameworks Incorporating Copper-Complexed Rotaxanes,' Angew. Chem. Int. Ed., 51:2160-2163 (2012).
Chun et al., 'Concomitant Formation of N-Heterocyclic Carbene-Copper Comlexies within a Supramolecular Network in the Self-Assembly of Immidzolium Dicarboxylate with Metal Ions,' Inorganic Chemistry, Jul. 20, 2009, pp. 6353-6355, vol. 48, No. 14.

(56) References Cited

OTHER PUBLICATIONS

Chun et al., 'Cu2O: A versatile Reagent for Base-Free Direct Synthesis of NHC-Copper Complexes and Decoration of 3D-MOF with Coordinatively Unsaturated NHC-Copper Species,' Organometallics, Mar. 16, 2010, pp. 1518-1521, vol. 29, No. 7.
Cordero Garcia, Marcela M. Nonfinal Office Action for U.S. Appl. 12/680,141, dated Nov. 2, 2012.
Crees et al., 'Synthesis of a Zinc(II) Imidazolium Dicarboxylate Logand Metal-Organic Framework (MOF): a Potential Precursor to MOF-Tethered N-Heterocyclic Carbene Compounds,' Inorganic Chemistry, Jan. 19, 2010, vol. 49, No. 4, pp. 1712-1719.
Deng et al., 'Large-Pore Apertures in a Series of Metal-Organic Frameworks,' Science 336:1018-1023 (May 25, 2012).
Fracaroli et al., 'Isomers of Metal-Organic Complex Arrays,' Inorg. Chem. 51: 6437-6439 (Jun. 5, 2012).
Furukawa et al., 'Isoreticular Expansion of MetalOrganic Frameworks with Triangular and Square Building Units and the Lowest Calculated Density for Porous Crystals,' Inorg. Chem. 50:9147-9152 (2011).
Gandara et al., 'Porous, Conductive Metal-Triazolates and Their Structural Elucidation by the Charge-Flipping Method,' Chem. Eur. J. 18:10595-10601 (2012).
Gassensmith et al., 'Strong and Reversible Binding of Carbon Dioxide in a Green Metal-Organic Framework,' J. Am. Chem. Soc. 133:15312-15315 (Aug. 30, 2011).
Hmadeh et al., 'New Porous Crystals of Extended Metal-Catecholates,' J. Chem. Mater. 24:3511-3513 (Aug. 28, 2012).
Jones, Christopher. Nonfinal Office Action for U.S. Appl. No. 12/598,855, dated Jun. 14, 2012.
Jones, Christopher. Nonfinal Office Action for U.S. Appl. No. 12/598,855, dated Oct. 12, 2012.
Koh et al., 'A Crystalline Mesoporous Coordination Copolymer with High Microporosity,' Angew Chem Int'l, 2008, pp. 677-680, vol. 47.
Demir et al., 'Role of Copper Species in the Oxidative Dimerization of Arylboronic Acids: Synthesis of Symmetrical Biaryls', Journal of Organic Chemistry 68(26):10130-10134 (2003).
Gonzalez-Arellano et al., 'Homogeneous and heterogeneous Au(III) Schiff base-complexes as selective and general catalysts for self-coupling of aryl boronic acids,' Chem. Comm. 15:1990-1992 (2005).
Kirai et al., 'Homocoupling of arylboronic acids catalyzed by 1,10-phenanthroline—ligated copper complexes in air,' European Journal of Organic Chemistry 12:1864-1867 (2009).
Koza et al., 'An efficient High Yielding Approach for the Homocoupling of Aryl Boronic Acids,' Synthesis 15:2183-2186 (2002).
Lawrence, Frank M. Nonfinal Office Action for U.S. Appl. No. 12/699,616, dated Apr. 10, 2012.
Lee et al., 'Synthesis and Gas Sorption Properties of a Metal-Azolium Framework (MAF) Material,' Inorganic Chemistry, Nov. 2, 2009, pp. 9971-9973, vol. 48, No. 21.
McKeown et al., 'Phthalocyanine-Based Nanoporous Network Polymers,' Chem. Comm. 23:2780-2781 (Oct. 31, 2002).
McKeown et al., 'Porphyrin-Based Nanoporous Network Polymers,' Chem. Comm. 23:2782-2783 (Oct. 31, 2002).
Morris et al., 'Framework mobility in the metal-organic framework crystal IRMOF-3: Evidence for aromatic ring and amine rotation,' Journal of Molecular Structure 1004:94-101 (2011).
Morris et al., 'NMR and X-ray Study Revealing the Rigidity of Zeolitic Imidazolate Frameworks,' J. Phys. Chem. 116(24)13307-13312 (Jun. 1, 2012).
Morris et al., 'Synthesis, Structure, and Metalation of Two New Highly Porous Zirconium Metal-Organic Frameworks,' Inorg. Chem. 51:6443-6445 (Jun. 7, 2012).
O'Keeffe et al., 'Deconstructing the Crystal Structures of Metal-Organic Frameworks and Related Materials into Their Underlying Nets,' Chem. Rev. 112(2):675-702 (Feb. 8, 2012).
Queen et al., 'Site-Specific CO2 Adsorption and Zero Thermal Expansion in an Anisotropic Pore Network,' J. Phys. Chem. C, 115:24915-24919 (Nov. 8, 2011).
Rinkel, Bert. Extended European Search Report for European Patent Application EP08713961, dated Jan. 2, 2012.
Rouseau-Jager, Nadia, International Search Report and Written Opinion, PCT/US2011/024671, European Patent Office, dated Dec. 13, 2011.
Sines, Brian J. Nonfinal Office Action for U.S. Appl. No. 13/142,564, dated Jul. 9, 2012.
Song et al., 'A Multiunit Catalyst with Synergistic Stability and Reactivity: A PolyoxometalateMetal Organic Framework for Aerobic Decontamination,' J. Am. Chem. Soc. 133(42):16839-16846 (Sep. 13, 2011).
Spitler et al., 'Lewis acid-catalysed formation of two-dimensional phthalocyanine covalent organic frameworks', Nature Chemistry, vol. 2, Aug. 2010, pp. 672-677.
Tilford et al., 'Facile Synthesis of a Highly Crystalline, Covalently Porous Boronate Network,' 18(22):5296-5301 (Oct. 11, 2006).
Tranchemontagne et al., 'Hydrogen Storage in New Metal-Organic Frameworks,' J. Phys. Chem. C 116(24):13143-13151 (May 24, 2012).
Wan et al, 'A Belt-Shaped, Blue Luminescent, and Semiconducting Covalent Organic Framework.' Angew. Chem. Int. Ed. 47:8826-8830 (2008).
Wan et al., 'Covalent Organic Frameworks with High Charge Carrier Mobility,' Chem. Mater. 23:4094-4097 (Aug. 22, 2011).
Young, Jung Doo. International Search Report and Written Opinion for PCT/US2011/053423, dated Jul. 23, 2012.
Zhou et al., 'Introduction to Metal-Organic Frameworks,' Chemical Reviews 112:673-674 (Jan. 26, 2012).
Goto, Y et al., "Clickable Metal-Organic Framework," J. Am. Chem. Soc. 130:14354-14355 (2008).
Kyoungmoo et al., "A Crystalline Mesoporous Coordination Copolymer with High Microporosity," Angew. Chem. Int. Ed. 47(4):689-92 (2008).
Duren et al., 'Design of New Materials for Methane Storage,' Langmuir 20:2683-2689 (2004).
Eddaoudi et al., 'Modular Chemistry: Secondary Building Units as a Basis for the Design of Highly Porous and Robust Metal-Organic Carboxylate Frameworks' Acc. Chem. Res. 34:319-330 (2001).
Eddaoudi et al., 'Geometric Requirements and Examples of Important Structures in the Assembly of Square Building Blocks,' Proc. Natl. Acad. Sci. 99:4900-4904 (2002).
Eddaoudi et al., 'Systematic Design of Pore Size and Functionality in Isoreticular Metal-Organic Frameworks and Application in Methane Storage,' Science 295:469-472 (2002): Featured in (1) Chemical and Engineering News, Jan. 21, 2002, and (2) Chemical Insight magazine, Nov. 15, 2002.
Furukawa et al., 'Control of Vertex Geometry, Structure Dimensionality, Functionality, and Pore Metrics in the Reticular Synthesis of Crystalline Metal-Organic Frameworks and Polyhedra,' J. Am. Chem. Soc.130:11650-11661 (2008).
Furukawa et al., 'Ultra-High Porosity in Metal-Organic Frameworks,' Science 239:424-428 (2010).
Grzesiak et al., 'Polymer-Induced Heteronucleation for the Discovery of New Extended Solids,' Angew. Chem. Int. Ed. 45:2553-2556 (2006).
Halper et al., 'Topological Control in Heterom etal lie Metal-Organic Frameworks by Anion templating and Metalloligand Design,' J. Am. Chem. Soc, 2006, pp. 15255-15268, vol. 128.
Hayashi et al., 'Zeolite A Imidazolate Frameworks,' Nature Materials 6:501-506 (Jul. 2007).
Hexiang et al., 'Multiple Functional Groups of Varying Rations in Metal-Organic Frameworks,' Science 327(5967):846-850 (2010).
Huang et al., 'Ligand-Directed Strategy for Zeolite-Type Metal—Organic Frameworks: Zinc(ii) Imidazolates with Unusual Zeolitic Topologies,' Angew. Chem. Int. Ed. 45:1557-1559 (2006).
Kim et al., 'Assembly of Metal-Organic Frameworks from Large organic and Inorganic Secondary Building Units: New Examples and Simplifying Principles for Complex Structures,' J. Am. Chem. Soc, 2001, 123, 8239-8247.
Li et al., 'Design and Synthesis of an Exceptionally Stable and Highly Porous Metal-Organic Framework,' Nature, 1999, 402, 276-279: Featured in (1) Chemical and Engineering News, Nov. 22, 1999, and (2) Science News, Nov. 20, 1999.

(56) References Cited

OTHER PUBLICATIONS

Long et al., 'The Pervasive Chemistry of Metal-Organic Frameworks,' Chem. Soc. Rev. 38:1213-1214 (2009).
Lu et al., 'Synthesis and Structure of Chemically Stable Metal-Organic Polyhedra,' J. Am. Chem. Soc. 131:(35)12532-12533 (2009).
Morris et al., 'Crystals as Molecules: Postsynthesis Covalent Functionalization of Zeolitic Imidazolate Frameworks,' J. Am. Chem. Soc. 130:12626-12627 (2008).
Morris et al., 'A Combined Experimental—Computational Investigation of Carbon Dioxide Capture in a Series of Isoreticular Zeolitic Imidazolate Frameworks,' J. Am. Chem. Soc. 132:11006-11008 (2010).
Mulfort et al., 'Chemical Reduction of Metal-Organic Framework Materials as a Method to Enhance Gas Uptake and Binding,' J. Am. Chem. Soc. 129:9604-9605 (2007).
Ni et al., 'Porous Metal-Organic Truncated Octahedron Constructed from Paddle-Wheel Squares and Terthiophene Links,' J. Am. Chem. Soc. 127:12752-12753 (2005).
Young, Lee W., International Search Report and Written Opinion, Application No. PCT/US08/70149, dated Jan. 12, 2009.
Sigma-Aldrich, Citric acid, ACS reagent. Accessed online at https://www.sigmaaldrich.com/catalog/product/sial/251275?lang=en&region=US, 1 page.
Wardencki et al. Green Chemistry—Current and Future Issues. Review. Polish Journal of Environmental Studies. 2005. vol. 14, No. 4, pp. 389-395.
Whitfield et al. Metal-organic frameworks based on iron oxide octahedral chains connected by benzendicarboxylate dianions. Solid State Sciences, 2005. vol. 7, pp. 1096-1103.
Fang et al. A Metal-Organic Framework with the Zeolite MTN Topology Containing Large Cages of vol. 2.5 nm3. Ang Chem Int Ed 2005, vol. 44, pp. 3845-3848.
Zhao et al., 'Rigid-Strut-Containing Crown Ethers and [2]Catenanes for Incorporation into Metal-Organic Frameworks,' Chem. Eur. J. 15:13356-13380 (2009).
Peterson et al., 'Ammonia Vapor Removal by Cu3(BTC)2 and Its Characterization by MAS NMR,' J. Phys. Chem. C. 113(32):13906-13917 (2009).
Rosi et al., 'Infinite Secondary Building Units and Forbidden Catenation in Metal-Organic Frameworks,' Angew. Chem. Int. Ed. 41:294-297 (2002).
Rosi et al., 'Rod-Packings and Metal-Organic Frameworks Constructed from Rod-Shaped Secondary Building Units,' J. Am. Chem. Soc. 127:1504-1518 (2005).
Rowsell et al., 'Metal-Organic Frameworks: A New Class of Porous Materials,' Microporous Mesoporous Mater. 73:3-14 (2004).
Rowsell et al., 'Characterization of H2 Binding sites in prototypical metal-organic frameworks by inelastic neutron scattering,' J. Am. Chem. Soc. 127:14904-14910 (2005).
Seo et al., 'A homochiral metal-organic porous material for enantioselective separation and catalysis,' Nature 404:982-986 (2000).
Siberio-Perez, 'Raman Spectroscopic Investigation of CH4 and N2 Adsorption in Metal-Organic Frameworks,' Chem. Mater. 19:3681-3685 (2007).
Smaldone et al., 'Metal-Organic Frameworks from Edible Nature Products,' Angew. Chem. Int. Ed. 49:8630-8634 (2010).
Stallmach et al., 'NMR Studies on the Diffusion of Hydrocarbons on the Metal-Organic Framework Material MOF-5,' Angew. Chem. Int. Ed. 45:2123-2126 (2006).
Sudik et al., 'Design, Synthesis, Structure, and Gas (N2, Ar, CO2, CH4 and H2) Sorption Properties of Porous Metal-Organic Tetrahedral and Heterocuboidal Polyhedra,' J. Am. Chem. Soc. 127:7110-7118 (2005).
Tanabe et al., 'Systematic Functionalization of a Metal-Organic Framework via a Postsynthetic Modification Approach,' J. Am. Chem. Soc. 130(26):8508-8517 (2008).
Tranchemontagne et al. 'Metal-Organic Frameworks with High Capacity and Selectivity for Harmful Gases,' Proc. Natl. Acad. Sci. USA 105:11623-11627 (2008).
Tranchemontagne et al., 'Reticular Chemistry of Metal-Organic Polyhedra,' Angew. Chem. Int. Ed., 2008, 47:5136-5147 (2008).
Tranchemontagne et al., 'Room Temperature Synthesis of Metal-organic Frameworks: MOF-5, MOF-74, MOF-177, MOF-199, and IRMOF-0,' Tetrahedron 64:8553-8557 (2008).
Tranchemontagne et al. 'Secondary Building Units, Nets and Bonding in the Chemistry of Metal-Organic Frameworks,' Chem. Soc. Rev. 38:1257-1283 (2009).
Vairaprakash et al., 'Synthesis of Metal-Organic Complex Arrays,' J. Am. Chem. Soc. 133:759-761 (2011).
Valente et al., 'Metal-organic Frameworks with Designed Chiral Recognition Sites,' Chem. Commun. 46:4911-4913 (2010).
Vitillo et al., 'Role of Exposed Metal Sites in Hydrogen Storage in MOFs,' J. Am. Chem. Soc. 130(26):8386-8396 (2008).
Vodak et al., 'Metal-Organic Frameworks Constructed from Pentagonal Antiprismatic and Cuboctahedral Secondary Building Units,' Chem. Commun. 2534-2535 (2001).
Walton et al., 'Understanding Inflections and Steps in Carbon Dioxide Adsorption Isotherms in Metal-Organic Frameworks,' J. Am. Chem. Soc.130:406-407 (2008).
Wang et al., 'Postsynthetic Covalent Modification of a Neutral Metal-Organic Framework,' J. Am. Chem. Soc. 129(41):12368-12369 (2007).
Wang et al., 'Tandem Modification of Metal-Organic Frameworks by a Postsynthetic Approach,' Angew. Chem. Int. 47:4699-4702 (2008).
Yaghi et al., 'Mutually Interpenetrating Sheets and Channels in the Extended Structure of Cu(4,4'-Bipyridine)CI,' Angew. Chem. Int. Ed. Engl., 1995, 34, No. 2, 207-209.
Braun et al., '1,4-Benzenedicarboxylate Derivatives as Links in the Design of Paddle-Wheel Units and Metal-Organic Frameworks,' Chem. Commun. 24:2532-2533 (2001).
Britt et al., 'Highly efficient separation of carbon dioxide by a metal-organic framework replete with open metal sites,' Proc. Natl. Acad. Sci. USA 106:20637-20640 (2009).
Becamel, Philippe, International Preliminary Report on Patentability, PCT/US2012/023516, The International Bureau of WIPO, dated Aug. 6, 2013.
Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.
El-Kaderi, Hani M., et al., "Designed Synthesis of 3D Covalent Organic Frameworks", Science 316, 268 (Published Apr. 13, 2007), S1-S75.
El-Kaderi et al., "Supporting Online Material for Designed Synthesis of 3D Covalent Organic Frameworks", Science 316, 268 (2007).
Klemperer et al., "New Directions in Polyvanadate Chemistry: From Cages and Clusters to Baskets, Belts, Bowls, and Barrels", Angew. Chem. Int. Ed. Engl. 31 (1992) No. 1, pp. 49-51.
Koh et al., "A Crystalline Mesoporous Coordination Copolymer with High Microporosity", Angew. Chem. Int. Ed. 2008, 120, pp. 689-692.
Prajapati et al., "Metal-organic frameworks (MOFs) constructed from Znll/Cdll-2,2'-bipyridines and polycarboxylic acids: Synthesis, characterization and microstructural studies", Polyhedron 28 (2009) 600-608.
Shi-Jie et al., "Synthesis and Structural Characterization of a New 3D Lead Coordination Polymer with a Tetrazole-1-acetate Ligand", Chinese J. Struct. Chem., vol. 30, No. 7, 2011, pp. 1049-1053.
Wang, Yiting, First Office Action, Chinese Patent Application No. CN201080036940.6, dated Dec. 4, 2013.
Barman et al., "Incorporation of active metal sites in MOFs via in situ generated ligand deficient metal-linker complexes", Chem. Comm., 2011, pp. 1-3.
Britt et al., "Metal-Organic frameworks with high capacity and selectivity for harmful gases", PNAS, 2008, vol. 105, No. 33, pp. 11623-11627.
Che et al., "Mono- and Diprotonation of the [(n5-C5H5)Ti(W5O18)]3- and [(n5-C5Me5)Ti(W5O18)]3-Anions," Inorg. Chem. 1992, 31, 2920-2928.

(56) References Cited

OTHER PUBLICATIONS

Chen et al. "Photoluminescent Metal-Organic Polymer Constructed from Trimetallic Clusters and Mixed Carboxylates", Inorg. Chem. 2003, 42, 944-946.

Day et al., "A New Structure Type in Polyoxoanion Chemistry: Synthesis and Structure of the V5O143-Anion", J. Am. Chem. Soc. 1989, 111, 4518-4519.

Day et al., "Synthesis and Characterization of a Soluble Oxide Inclusion Complex, [CH3CNC(V12O324-)]", J. Am. Chem. Soc. 1989, 111, 5959-5961.

Yaghi et al., "Rhenium-Selenium-Chlorine Solid Phases: Cluster Excision and Core Substitution Reactions of Molecular Species", Inorg. Chem. 1992, 31, 4778-4784.

Yaghi et al., "Directed Transformation of Molecules to Solids: Synthesis of a Microporous Sulfide from Molecular Germanium Sulfide Cages", J. Am. Chem. Soc. 1994, 116, 807-808.

Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).

Zhao, Office Action in Chinese Patent Application No. 20088031572, dated Aug. 5, 2011.

Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.

Kim, Su Mi, International Search Report and Written Opinion, PCT/US2010/039154, Korean Intellectual Property Office, dated Feb. 23, 2011.

Burrows, Andrew D., et al., "Post-Synthetic Modification of Tagged MOFs", Angewa. Chem. Int . Ed., (20081020), vol. 47, pp. 8482-8486, XP008150669.

Koh, Kyoungmoo, et al., "A Crystalline Mesoporous Coordination Copolymer with High Microporosity", Angewandte Chemie International Edition, (Jan. 11, 2008), vol. 47, No. Issue, pp. 689-692, XP008150670.

Kim et al., "Isoreticular MOFs based on a rhombic dodecahedral MOP as a tertiary building unit", CrystEngComm, Mar. 3, 2014, vol. 16, pp. 6391-6397.

Patteux, Claudine, International Search Report and Written Opinion, Application No. PCT/US2010/043373, dated Oct. 6, 2010.

Jia, Xiao, The Third Office Action, Chinese Patent Application No. 201080021284.2, dated Aug. 19, 2014.

Mashiyama, Shinya, Office Action issued in Japanese Patent Application No. 2012-522962, Japanese Patent Office, dated May 27, 2014.

Lee, Ji Min, International Search Report and Written Opinion, Application No. PCT/US2010/039284, dated Feb. 23, 2011.

Oisaki et al., "A Metal-Organic Framework with Covalently Bound Organometallic Complexes," J. of the Amer. Chem. Soc., pp. 9262-9264, vol. 132, No. 27, 2010.

Sigma-Aldrich, Basolite C300 (MOF-199), catalog No. 688614; Copyright 2014.

Eiichiro Mizushima, Notice of Reasons for Rejection, Japanese Patent Application No. 2012-516363, dated Aug. 26, 2014.

Fei et al., 'A Nearly Planar Water Sheet Sndwiched between Strontium-Imidazolium Carboxylate Coordination Polymers,' Inorg. Chem., 2005, pp. 5200-5202, vol. 44.

Kokubo, Atsuki, Office Action, Japanese Patent Application No. 2012-553065, dated Feb. 3, 2015.

Kim, Su Mi, International Search Report and Written Opinion, Application No. PCT/US09/046463, dated Feb. 24, 2010.

Klaes, Daphane, International Search Report and Written Opinion for PCT/US2010/021201, European Patent Office, dated Apr. 27, 2010.

Lawrence, Frank M., Non-Final Office Action for U.S. Appl. No. 12/699,616, dated Aug. 3, 2012.

Liu, Lei, First Office Action, Chinese Patent Application No. 201180009370.6,The State Intellectual Property Office of the People's Republic of China, dated Mar. 3, 2014.

Moyse, Ellen, International Preliminary Report on Patentability and Written Opinion, PCT/US08/006008, The International Bureau of WIPO, dated Nov. 26, 2009.

Mulhausen, Dorothee, International Preliminary Report on Patentability, PCT/US2010/021201, The International Bureau of WIPO, dated Jul. 28, 2011.

Park, Jae Woo. International Search Report for PCT/US2010/039123, Korean Intellectual Property Office, dated Feb. 24, 2011.

Tranchemontagne et al. "Hydrogen Storage in New Metal-Organic Frameworks," J. Phys. Chem. C 116, 13143-13151.

Baharlou, Simin, International Preliminary Report on Patentability for PCT/US2009/043373, The International Bureau of WIPO, dated Feb. 9, 2012.

Baharlou, Simin, International Preliminary Report on Patentability for PCT/US2011/024671, The International Bureau of WIPO, dated Aug. 23, 2012.

Finger, Gabriela, International Search Report and Written Opinion, PCT/US2010/043373, European Patent Office, dated Oct. 6, 2010.

Deng, H. et al., "Large-Pore Apertures in a Series of Metal-Organic Frameworks," Science, vol. 336, No. 6084, May 12, 2012, pp. 1018-1023.

Eberhard, Michael, International Search Report and Written Opinion, PCT/US2012/059877, European Patent Office, dated Oct. 15, 2013.

McDonald, Thomas M. et al., 'Capture of Carbon Dioxide from Air and Flue Gas in the Alkylamine-Appended Metal-Organic Framework mmen-Mg 2 (dobpdc)', Journal of the American Chemical Society, vol. 134, No. 16, Apr. 4, 2012, pp. 7056-7065.

Becamel, Philippe, International Preliminary Report on Patentability, PCT/US2012/059877, The International Bureau of WIPO, dated Sep. 18, 2014.

Costa ("Chemical Modification of a Bridging Ligand Inside a Metal-Organic Framework while Maintaining the 3D Structure" Eur J. Inorg. Chem (2008) 10, 1551-1554).

Young, Jung Doo, International Search Report & Written Opinion, Korean Application No. PCT/US2011/044625, dated Feb. 24, 2012.

Szeto et al., "A Thermally Stable Pt/Y-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.

Szeto et al., "Characterization of a New Porous Pt-Containing Metal-Organic Framework Containing Potentially Catalytically Active Sites: Local Electronic Structure at the Metal Centers", Chem. Mater., 2007, 19, 211-220.

First Office Action issued in Chinese Patent Application No. 201180045210.8, dated Sep. 28, 2014.

Dhakshinamoorthy et al., "Metal-organic frameworks as heterogeneous catalysts for oxidation reactions", Catal. Sci. Technol., Apr. 28, 2011, 1, 856-867.

Eberhard, Michael, Extended European Search Report, EP11810321, dated Jan. 14, 2014.

Hassan et al., "Aryl-Aryl Bond Formation One Century After the Discovery of the Ullmann Reaction", Chem. Rev., Published on Web: Mar. 8, 2002, 102, 1359-1469.

Leus et al., "The remarkable catalytic activity of the saturated metal organic framework V-MIL-47 in the cyclohexene oxidation", Chem. Comm., Jun. 18, 2010, 46, 5085-5087.

Lindner, Nora, International Preliminary Report on Patentability and Written Opinion, The International Bureau of WIPO, PCT/US2011/044625, dated Jan. 31, 2013.

Meneses, Ociel Esau Andrade, First Office Action, Mexican Application No. MX/a/2013/00469, Mexican Institute of Industrial Property (IMPI), dated Jan. 26, 2015.

Young, Jung Doo, Written Opinion, PCT/US2011/053423, Korean Intellectual Property Office, dated Jul. 23, 2012.

Lindner, Nora, International Preliminary Report on Patentability, PCT/US2011/053423, The International Bureau of WIPO, dated Apr. 2, 2013.

(56) References Cited

OTHER PUBLICATIONS

Richter, Herbert, Supplementary European Search Report, European Patent Application No. 11848340.3, European Patent Office, dated Feb. 6, 2014.
Qiu, Xiaowei, Chinese Patent Application No. 201180056905.5, First Office Action, dated Jul. 18, 2014.
Qiu, Xiaowei, Chinese Application No. 201180056905.5, Second Office Action, dated Feb. 3, 2015.
Mineko Mohri, International Preliminary Report on Patentability and Written Opinion, PCT/US2015/016555, The International Bureau of WIPO, dated Sep. 1, 2016.
Carboni et al., "Highly porous and stable metal-organic frameworks for uranium extraction," Chemical Science, 4:2396-2402, Apr. 4, 2013.
Corma et al., "From MOFs to zeolites: zirconium sites for epoxide rearrangement," New J. of Chem. 37:3496-3502, Aug. 2, 2013.
Garibay et al., "Isoreticular synthesis and modification of frameworks with the UiO-66 topology," Chemical Communications, 46:7700-7702, Sep. 27, 2010.
Hurenkamp, Jaap, International Search Report and Written Opinion, PCTUS2015/016555, European Patent Office, dated May 6, 2015.
Bjai, Lingfei, International Preliminary Report on Patentability and Written Opinion, PCT/US2015/021107, The International Bureau of WIPO, dated Sep. 20, 2016.
Bhakta et al., 'Metal organic frameworks as templates for nanoscale NaAlH4', Journal of American Chemical Society, vol. 131, No. 37, Sep. 23, 2009, pp. S1-S14.
Finger, Gabriela, International Search Report and Written Opinion, PCT/US2015/021107, European Patent Office, dated Aug. 17, 2015.
Gandara et al., 'High Methane Storage Capacity in Aluminum Metal-Organic Frameworks', Journal of the American Chemical Society, vol. 136, No. 14, Mar. 21, 2014, pp. 5271-5274.
Mason, Jarad A., "Evaluating metal-organic frameworks for natural gas storage", Chemical Science, vol. 5, Accepted Oct. 22, 2013, pp. 32-51.
Peng et al., 'Methane Storage in Metal-Organic Frameworks: Current Records, Surprise Findings, and Challenges', Journal of the American Chemical Society, vol. 135, No. 2, Aug. 14, 2013, pp. 11887-11894.
Dietzel, Pascal D. C., et. al., "Application of metal-organic frameworks with coordinatively unsaturated metal sites in storage and separation of methane and carbon dioxide", Journal of Materials Chemistry, (20090821), vol. 19, No. 39, doi:10.1039/b911242a, ISSN 0959-9428, pp. 7362-7370, XP055197279.
Ren Shi-Bin et al, "The variety of conformational isomerism of a flexible organic linker induced by the position and amounts of aromatic carboxylic groups", Polyhedron, (20140604), vol. 83, doi:10.1016/J.POLY.2014.05.069, ISSN 0277-5387, pp. 130-136, XP029080831.
Chen, Binling, et. al., "Zeolitic imidazolate framework materials: recent progress in synthesis and applications", Journal of Materials Chemistry A: Materials for Energy and Sustainability, GB, (20140717), vol. 2, No. 40, doi:10.1039/C4TA02984D, ISSN 2050-7488, pp. 16811-16831, XP055337959.
Li et al., 'Transformation of Germanium Dioxide to 4-Connected Porous Germanate Net,' J. Am. Chem. Soc, 1998, 120, 10569-10570.
Li et al., 'An Open-Framework Germanate with Polycubane-Like Topology,' Angew. Chem. Int. Ed., 38:653-655 (1999).
Li et al., 'Supertetrahedral Sulfide Crystals with Giant Cavities and Channels,' Science, 1999, 283, 1145-1147.
Li et al., 'Non-interpenetrating Indium Sulfide with a Supertetrahedral Cristobalite Framework,' J. Am. Chem. Soc, 1999, 121,6096-6097.
Li et al., 'Ge2Zr06F2 (H2DAB)H20: A 4-Connected Microporous Material with 'Bow Tie' Building Units and an Exceptional Proportion of 3-Rings,' J. Am. Chem. Soc, 2000, 122, 12409-12410.
Li et al., '20 A [Cd4In16S35]14—Supertetrahedral T4 Clusters as Building Units in Decorated Cristobalite Frameworks,' J. Am. Chem. Soc, 2001, 123, 4867-4868.

Li et al.,'[Cd16In64S134]44-: 31-A Tetrahedron with a Large Cavity,' Angew. Chem. Int. Ed., 42:1819-1821 (2003).
Centrone et al., 'Raman Spectra of Hydrogen and Deuterium Adsorbed on a Metal-Organic Framework,' Chem. Phys. Lett. 411:516-519 (2005).
Chen et al., 'Transformation of a Metal-Organic Framework from the NbO to PtS Net,' Inorg. Chem. 41:181-183 (2005).
Chen et al., 'A Microporous Metal-Organic Framework for Gas-Chomatographic Separation of Alkanes,' Angew. Chem. Int. Ed. 45:1390-1393 (2006).
Cho et al., 'A metal-organic framework material that functions as an enantioselective catalyst for olefin epoxidation,' Chem. Comm. 24:2563-2565 (2006).
Yaghi et al., 'Open-Framework Solids with Diamond-Like Structures Prepared from Clusters and Metal-Organic Building Blocks,' Mater. Res. Soc. Symp. Proc, 1995, 371, 15.
Yaghi et al., 'Hydrothermal Synthesis of a Metal-Organic Framework Containing Large Rectangular Channels,' J. Am. Chem. Soc, 1995, 117, 10401-10402.
Yaghi et al., 'Selective Guest Binding by Tailored Channels in a 3-D Porous Zinc(II)-1,3,5-Benzenetricarboxylate Network,' J. Am. Chem. Soc, 1997, 119, 2861-2868.
Yaghi et al., 'Crystal Growth of Extended Solids by Nonaqueous Gel Diffusion,' Chem. Mater., 1997, 9, 1074-1076.
Yaghi et al., 'A Molecular Railroad with Large Pores: Synthesis and Structure of Ni(4,4'-bpy)2.5(H20)2(CI04)2.1.5 (4,4'-bpy)2(H2O),' Inorg. Chem., 1997, 36, 4292-4293.
Yaghi et al., 'Construction of a New Open-Framework Solid from 1,3,5-Cyclohexanetricarboxylate and Zinc(II) Building Blocks,' J. Chem. Soc, Dalton Trans., 1997, 2383-2384.
Yaghi et al., 'T-Shaped Molecular Building Units in the Porous Structure of Ag(4,4'-bpy) N03,' J. Am. Chem. Soc, 1996, 118, 295-296.
Yaghi et al., 'Synthesis and Structure of a Metal-Organic Solid Having the Cadmium (II) Sulfate Net,' Mater. Res. Soc. Symp. Proc. 453:127, (1997).
Zhaofu et al., 'A Nearly Planar Water Sheet Sandwiched between Strontium-Imidazolium Carboxylate Coordination Polymers,' Inorg. Chem. 44:5200-5202 (2005).
Nickitas-Etienne, Athina, International Preliminary Report on Patentability, PCT/US2009/068731, The International Bureau of WIPO, dated Jun. 30, 2011.
Wang, Zhenqiang, et al., 'Postsynthetic Covalent Modification of a Neutral Metal—Organic Framework', J. Am. Chem. Soc., (2007), vol. 129, No. 41, pp. 12368-12369.
Morris, et al., 'Crystals as Molecules: Postsynthesis Covalent Functionalization of Zeolitic Imidazolate Frameworks', J. Am. Chem. Soc., (Aug. 2008), vol. 130, No. 38, pp. 12626-12627.
Zhenqiang Wang et al., 'Tandem Modification of Metal-Organic Frameworks by a Postsynthetic Approach', Angew Chem Int Ed, (200800686), vol. 47, pp. 4699-4702.
Britt et al., 'Ring-Opening Reactions Within Metal-Organic Frameworks,' Inorg. Chem. 49:6387-6389 (2010).
Sigma-Aldrich, Basolite C300 (MOF-199), catalog No. 688614; http://www.sigmaaldrich.com/catalog/ProductDetail.do?D7=0&N5=SEARCH.sub.--CONCAT.sub.-PNO%7CBRAND.sub.-KEY&N4=688614%7CALDRICH&N25=0&Qs=ON&F=SPEC-, obtained online in 2014.
Eddaoudi, M et al., "Systematic Design of Pore Size and Functionality in Isoreticular MOFs and Their application in Methane Storage" Science, (2002), vol. 295, pp. 469-472.
Akporiaye et al., 'Combinatorial Approach to the Hydrothermal Synthesis of Zeolites,' Angew. Chemie 37(5):609-611 (1998).
Corma et al., 'A large-cavity zeolite with wide pore windows and potential as an oil refining catalyst,' Nature, vol. 418, pp. 514-517 (0812002).
Ferragut et al., 'Positronium Formation in Porous Materials for Antihydrogen Production,' J. Phys. Conf. Ser. 225:1-8 (2010).
Forster et al., 'A High-Throughput Investigation of the Role of pH, Temperature, Concentration, and Time on the Synthesis of Hybrid Inorganic-Organic Materials,' Angew. Chemie Int Ed. 44(46):7608-7611 (2005).

(56) References Cited

OTHER PUBLICATIONS

Howe, Patrick, International Search Report and Written Opinion, Application No. PCT/US2009/068849, dated Jun. 4, 2010.
Klein et al., 'Combinatorial Material Libraries on the Microgram Scale with an Example of Hydrothermal Synthesis,' Angew. Chemie 37(24):3369-3372 (1998).
Novoa, Carlos, International Search Report and Written Opinion for PCT/US2010/021201, European Patent Office, dated Apr. 27, 2010.
Holler et al., "The First Dintrile Frameworks of the Rare Earth Elements: 3[LnCL3(1,4-Ph(CN2)] and 3[Ln2CL6(1,4-Ph (CN)2)], Ln=Sm, Gd, Tb, Y; Access to Novel Metal-Organic Frameworks by Solvent Free Synthesis in Molten 1,4-Benzodinitrile," Inorganic Chemistry, 2008, pp. 10141-10149, vol. 47, No. 21.
Holler, Christoph J.,et. al., "The first dinitrile frameworks of the rare earth elements: [LnCl3(1,4-Ph(CN)2] and [Ln2Cl6(1,4Ph(CN)2], Ln=Sm, Gd, Tb, Y;Access to novel metal-organic frameworks by solvent free synthesis in molten 1,4-benzodinitril", Inorganic Chemistry, (20080810), vol. 47, No. 21, p. 10141, XP002574067.
Zhang et al., 'Crystal engineering of binary metal imidazolate and triazolate frameworks,' Chem. Comm. 1689-1699 (2006).
Zhu, A. et al., 'Isomeric Zinc(II) Triazolate Frameworks with 3-Connected Networks: Syntheses, Structures, and Sorption Properties,' Inorg. Chem. 48:3882-3889 (2009).
Zhou, X et al., 'Hydrothermal Syntheses and Structures of Three Novel Coordination Polymers Assembled from 1,2,3-Triazolate Ligands,' CrystEngComm. 11:1964-1970 (2009).
Demessence, A et al., 'Strong CO2 Bnding in a Water-Stable, Triazolate-Bridged Metal-Organic Framework Functionalized with Ethylenediamine,' J. Am. Chem. Soc. 131:8784-8786 (2009).
Young, Jung Doo, International Search Report and Written Opinion, Application No. PCT/US2012/022114, dated Aug. 22, 2012.
Bai, Lingfei, International Preliminary Report on Patentability and Written Opinion, the International Bureau of WIPO, PCT/US2012/022114 dated Jul. 23, 2013.
Yang et al., 'Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties,' Crystal Growth Design 7(10):2009-2015 (2007).
Park, H. et al., 'Synthesis, Structure Determination and Hydrogen Sorption Studies of New Metal-Organic Frameworks Using Triazole and Naphthalenedicarboxylic Acid,' Chem. Natur. 19:1302-1308 (2007).
Li, Y. et al., 'Hydrogen Storage in Metal-Organic and Covalent-Organic Frameworks by Spillover,' AIChe Journal 54 (1):269-279 (2008).
Gadzikwa, T. et al., 'Selective Bifunctional Modification of a Non-catenated Metal-Organic Framework Material via Click Chemistry,' J. Am. Chem. Soc. 131:13613-13615 (2009).
Zhang, J. et al., 'Exceptional Framework Flexibility and Sorption Behavior of a Multifunctional Porous Cuprous Triazolate Framework,' J. Am. Chem. Soc. 130:6010-6017 (2008).
Luo et al., 'Two new metal-triazole-benzenedicarboxylate frameworks affording an uncommon 3,4-connected net and unique 4,6-connected rod packing: hydrothermal synthesis, structure, thermostability and luminescence studies,' CrystEngComm 11 (6): 1097-1102 (2009).
Li et al., 'Synthesis and Structural Characterization of a New 3D Lead Coordination Polymer with a Tetrazole-1-acetate Ligand,' Chinese J. Struct. Chem. 30(7): 1049-1053 (2011).
Furukawa et al., "Structuring of metal-organic frameworks at the mesoscopiclmacroscopic scale", Chemical Society Reviews, vol. 43, No. 16, Jan. 1, 2014, pp. 5700-5734.
Lange, Tim, Communication Pursuant to Article 94(3) EPC, Application No. 15717990.4, European Patent Office, dated Mar. 9, 2018.
Reboul, Julien et al., "Mesoscopic architectures of porous coordination polymers fabricated by pseudomorphic replication", Nature Materials, vol. 11, No. 8, Aug. 1, 2012, pp. 717-723.
Nickitas-Etienne, Athina, International Preliminary Report on Patentability and Written Opinion, Application No. PCT/US2015/023173, dated Oct. 4, 2016.

Burrows, Andrew D., 'Mixed-component metal-organic frameworks (MC-MOFs): enhancing functionality through solid solution formation and surface modifications', Crystengcomm, vol. 13, No. 11, Jan. 1, 2011, pp. 3623-3642.
Deng et al., 'Multiple Functional Groups of Varying Ratios in Metal-Organic Frameworks', Science, vol. 327, No. 5967, Feb. 12, 2010, pp. 846-850.
Fracaroli, A.M. et al., Metal-Organic Frameworks with Precisely Designed Interior for Carbon Dioxide Capture in the Presence of Water, J. Am. Chem. Soc, Jun. 25, 2014, vol. 136, No. 25, pp. 8863-8866.
Duval, Eric, International Search Report and Written Opinion, Application No. PCT/US2015/023173, dated Apr. 11, 2016.
Kong et al., 'Mapping of Functional Groups in Metal-Organic Frameworks', Science, vol. 341, No. 6148, Jul. 25, 2013, pp. 882-885.
Baharlou, Simin, International Preliminary Report on Patentability for PCT/US2009/046463, The International Bureau of WIPO, dated Dec. 16, 2010.
Barton et al., 'Tailored Porous Materials,' Chem. Mater. 11:2633-2656 (1999).
Chae et al., 'A Route to High Surface Area, Porosity and Inclusion of Large Molecules in Crystals,' Nature427, 523-527 (2004); Featured in (1) Chemical & Engineering News magazine, Feb. 9, 2004, (2) BBC World Service, Feb. 2004, (3) New Scientist, Feb. 2004.
Cote et al., 'Porous, Crystalline, Covalent Organic Frameworks,' Science 310:1166-1170 (2005).
Cote et al., 'Reticular Synthesis of Microporous and Mesoporous 2D Covalent Organic Frameworks,' J. Am. Chem. Soc. 129:12914-12915 (2007).
Doonan et al., 'Exceptional ammonia uptake by a covalent organic framework,' Nature Chem. 2:235-238 (2010).
Furukawa et al., 'Storage of Hydrogen, Methane, and Carbon Dioxide in Highly Porous Covalent Organic Frameworks for Clean Energy Applications,' J. Am. Chem. Soc. 25:8876-8883 (2009).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Han et al., 'Covalent Organic Frameworks as Exceptional Hydrogen Storage Materials,' J. Am. Chem. Soc. 130: 11580-11581 (2008).
Honda, Masashi, International Preliminary Report on Patentability for PCT/US2008/051859, dated Jul. 28, 2009.
Howe, Patrick, International Search Report and Written Opinion, Application No. PCT/US2010/022777, dated Jun. 7, 2010.
Hunt et al., 'Reticular Synthesis of Covalent Organic Borosilicate Frameworks,' J. Am. Chem. Soc. 130: 11872-11873 (2008).
El-Kaderi et al., 'Designed Synthesis of 3D Covalent Organic Frameworks,' Science 316:268-272 (2007).
Kim, Su Mi, International Search Report and Written Opinion for PCT/US2009/068731, dated Aug. 19, 2010.
Kim, Su Mi. International Search Report for PCT/US2010/039154, dated Feb. 23, 2011.
Klaes, Daphne. International Search Report and Written Opinion for PCT/US2010/021201, dated Apr. 27, 2010.
Kyoungmoo et al., 'A Crystalline Mesoporous Coordination Copolymer with High Microporosity,' Angew. Chem. Int. Ed. 47(4):677-680 (2008).
Linder, Nora, International Preliminary Report on Patentability and Written Opinion, Application No. PCT/US2010/022777, dated Aug. 2, 2011.
Mendoza-Cortes et al., 'Adsorption Mechanism and Uptake of Methane in Covalent Organic Frameworks: Theory and Experiment,' J. Phys. Chem. 114:10824-10833 (2010).
Michalitsch, Richard, International Search Report and Written Opinion for PCT/US2009/069700, European Patent Office, dated May 7, 2010.
Mulhausen, Dorothee, International Preliminary Report on Patentability, PCT/US2009/069700, The International Bureau of WIPO, dated Jul. 7, 2011.

(56) References Cited

OTHER PUBLICATIONS

Mulhausen, Dorothee. International Preliminary Report on Patentability for PCT/US2010/021201, dated Jul. 28, 2011.
Nickitas-Etienne, Athina, International Preliminary Report on Patentability,PCT/US2008/077741, The Internationa Bureau of WIPO, dated Mar. 30, 2010.
Nickitas-Etienne, Athina. International Preliminary Report on Patentability for PCT/US2009/068731, dated Jun. 21, 2011.
Nickitas-Etienne, Athina. International Preliminary Report on Patentability for PCT/US2009/068849, dated Jun. 30, 2011.
O'Keeffe et al., 'Frameworks for Extended Solids: Geometrical Design Principles,' J. Solid State Chem. 152:3-20 (2000).
Okeefffe et al., 'Reticular Chemistry—Present and Future Prospects—Introduction,' J. Solid State Chem.178:V-VI (2005).
O'Keeffe et al., 'The Reticular Chemistry Structure Resource (RCSR) Database of, and Symbols for, Crystal Nets,' Am. Chem. Res. 41:1782-1789 (2008).
Park, Jae Woo. International Search Report for PCT/US2010/039123, dated Feb. 24, 2011.
Patteux, Claudine. International Search Report for PCT/US2010/043373, dated Oct. 10, 2010.
Uribe-Romo et al., 'A Crystalline Imine-Linked 3-D Porous Covalent Organic Framework,' J. Am. Chem. Soc. 131:4570-4571 (2009).
Uribe-Romo et al., 'Crystalline Covalent Organic Frameworks with Hydrazone Linkages,' J. Am. Chem. Soc. 133: 11478-11481 (2011).
Vodak et al., 'One-Step Synthesis and Structure of an Oligo(spiro-orthocarbonate),' J. Am. Chem. Soc.124 (18):4942-4943 (2002).
Vodak et al., 'Computation of Aromatic C3N4 Networks and Synthesis of the Molecular Precursor N(C3N3)3C16,' Chem. Eur. J. 9:4197-4201 (2003).
Yaghi et al., 'Construction of Microporous Materials from Molecular Building Blocks,' Fundamental Materials Research, T. J. Pinnavaia and M. F. Thorpe, eds., vol. II, Plenum: New York, p. 111 (1995).
Yaghi et al., 'Construction of Porous Solids from Hydrogen-Bonded Metal Complexes of 1,3,5-Benzenetricarboxylic Acid,' J. Am. Chem. Soc, 1996, 118, 9096-9101.
Yaghi et al., 'Designing Microporosity in Coordination Solids,' Modular Chemistry, J. Michl (ed.), Kluwer Academic Publishers, p. 663-670 (1997).
Yaghi et al., 'Synthetic Strategies, Structure Patterns, and Emerging Properties in the Chemistry of Modular Porous Solids,' Acc. Chem. Res. 31:474-484 (1998).
Yaghi et al., 'Design of Solids Molecular Building Blocks: Golden Opportunities for Solid State Chemistry,' J. Solid State Chem. 152, 1-2 (2000).
Yaghi et al., 'A Molecular World Full of Holes,' Chem. Innov. p. 3 (2000).
Yaghi et al., 'Reticular Synthesis and the Design of New Materials,' Nature 423:705-714 (2003).
Yaghi, Omar., 'Porous Crystals for Carbon Dioxide Storage,' slide presentation at the Fifth Annual Conference on Carbon Capture & Sequestration, US Department of Energy on May 10, 2006 http://www.netl.doe.gov/publications/proceedings/06/carbon-seq/Tech.degre- e.20Session.degree.20193.pdf.
Yaghi et al., 'Metal-Organic Frameworks: A Tale of Two Entanglements,' Nature materials 6:92-93 (2007).
Takahashi, Narinori, Office Action, Application No. 2016-557628, Japanese Patent Office, dated Jan. 8, 2019.

* cited by examiner

MESOSCOPIC MATERIALS COMPRISED OF ORDERED SUPERLATTICES OF MICROPOROUS METAL-ORGANIC FRAMEWORKS

CROSS REFERENCE TO RELATED APPLICATIONS

This application is a U.S. National Stage Application filed under 35 U.S.C. 371 and claims priority to International Application No. PCT/US2015/021090, filed Mar. 17, 2015, which application claims priority under 35 U.S.C. § 119 from Provisional Application Ser. No. 61/955,084, filed Mar. 18, 2014, the disclosures of which are incorporated herein by reference.

TECHNICAL FIELD

The disclosure provides for mesoscopic materials which are comprised of ordered superlattices of metal-organic frameworks (MOFs), the manufacture thereof, and the use of the mesoscopic materials for various applications, such as catalysis, light harvesting, and meta-materials.

BACKGROUND

Metal-organic frameworks (MOFs) are porous crystalline nano-materials that are constructed by linking metal clusters called Secondary Binding Units (SBUs) and organic linking moieties. MOFs have high surface area and high porosity which enable them to be utilized in diverse fields, such as gas storage, catalysis, and sensors.

SUMMARY

The disclosure provides for innovative mesoscopic materials (MOF heterolites), comprising ordered superlattices of a plurality of microporous metal-organic framework (MOF) nanocrystals. The MOF heterolites disclosed herein exhibit chemical and physical properties based on the interplay between the nanoscopic MOF building blocks at the mesoscopic level. Due to the long range crystalline ordering of the MOF heterolites, the mesoscopic materials are open materials that are ideal for catalysis, gas storage and gas separation. The MOF heterolites unit lengths can be tuned to any frequency of interest, leading to the use of MOF heterolites in light capturing applications, catalysis, and metamaterials.

The disclosure also provides methods which allow for the targeted self-assembly of the MOF heterolites disclosed herein. Moreover, the self-assembly methods allow for size and shape directed sedimentation of MOFs, including MOFs with large chemical differences, to form permanently porous supercrystals. The methods further provide for the precise surfactant functionalization of MOFs.

In a particular embodiment, the disclosure provides for a metal-organic framework (MOF) heterolite mesoscopic material that is comprised of an ordered superlattice of metal-organic frameworks (MOFs). In a further embodiment, the MOF heterolite disclosed herein is comprised of a plurality of MOFs, wherein the MOFs are comprised of a plurality of linked M-X-L secondary binding units (SBUs), wherein M is a metal, metal ion, or metal containing complex; X is an atom from an organic linking ligand that can form one or more bonds with M; and L is an organic linking ligand comprising an optionally substituted ($C_1$-$C_{20}$) alkyl, optionally substituted ($C_1$-$C_{20}$) alkenyl, optionally substituted ($C_1$-$C_{20}$) alkynyl, optionally substituted ($C_1$-$C_{20}$) hetero-alkyl, optionally substituted ($C_1$-$C_{20}$) hetero-alkenyl, optionally substituted ($C_1$-$C_{20}$) hetero-alkynyl, optionally substituted ($C_3$-$C_{12}$) cycloalkyl, optionally substituted ($C_3$-$C_{12}$) cycloalkenyl, optionally substituted aryl, optionally substituted heterocycle or optionally substituted mixed ring system. In yet a further embodiment, the MOFs making up the MOF heterolite comprise a metal or metal ion selected from $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and combinations thereof, including any complexes which contain the metals or metal ions listed above, as well as any corresponding metal salt counter-anions. In another embodiment, the MOF heterolite disclosed herein is comprised of a plurality of zirconium based MOFs.

In a certain embodiment, the disclosure provides that the MOF heterolite disclosed herein is comprised of homogeneous MOFs. In an alternate embodiment, the MOF heterolite disclosed herein is comprised of heterogeneous MOFs. In a further embodiment, the MOF heterolite is comprised from two to eight structurally different MOFs. In another embodiment, the MOF heterolite is comprised of structurally different MOFs that have different gas sorption and/or gas separation properties or catalytic properties. In yet a further embodiment, a MOF heterolite disclosed herein is comprised of at least one MOF that catalyzes the oxidation of water, and at least one MOF that catalyzes the reduction of carbon dioxide. In another embodiment, the disclosure provides for a MOF heterolite that comprises a supercrystal that is between 250 nm to 1500 nm in size, or is between 500 nm to 1000 nm in size.

In a certain embodiment, the disclosure provides a method to produce a MOF heterolite disclosed herein comprising: preparing a MOF reaction mixture comprising metal or metal ions, organic molecules comprising multidentate functional groups, a suitable modulating agent, and a suitable solvent system; crystallizing the MOFs by adding a dilute base to the reaction mixture, and then heating at a predetermined temperature and sufficient period of time to allow for crystal formation; preparing a colloidal solution comprising the MOFs; assembling the MOFs from the colloidal solution into MOF heterolites by using accelerated sedimentation in a centrifuge or gravimetric sedimentation in a pipette assembly. In another embodiment, a surfactant is added to colloidal solution. Examples of surfactants include: polyvinylpyrrolidone, sodium dodecyl sulfate, cetrimonium bromide and triton X-100.

In a particular embodiment, the disclosure provides for a device (e.g., a gas storage and/or separation device) which comprises a MOF heterolite of the disclosure.

The disclosure provides a metal-organic framework (MOF) heterolite mesoscopic material that is comprised of an ordered superlattice of metal-organic frameworks (MOFs). In one embodiment, the heterolite is comprised of a plurality of MOFs, wherein the MOFs are comprised of a plurality of linked M-X-L units, wherein M is a metal, metal ion, or metal containing complex; X is an atom from an organic linking ligand that can form one or more bonds with M; and L is an organic linking ligand comprising an optionally substituted ($C_1$-$C_{20}$) alkyl, optionally substituted ($C_1$-$C_{20}$) alkenyl, optionally substituted ($C_1$-$C_{20}$) alkynyl, optionally substituted ($C_1$-$C_{20}$) hetero-alkyl, optionally substituted ($C_1$-$C_{20}$) hetero-alkenyl, optionally substituted ($C_1$-$C_{20}$) hetero-alkynyl, optionally substituted ($C_3$-$C_{12}$) cycloalkyl, optionally substituted ($C_3$-$C_{12}$) cycloalkenyl, optionally substituted aryl, optionally substituted heterocycle or optionally substituted mixed ring system, wherein the linking ligand comprises at least two or more carboxylate linking clusters. In a further embodiment, the organic linking ligand is selected from the group consisting of:

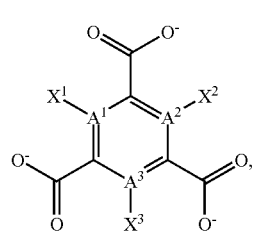
(I)

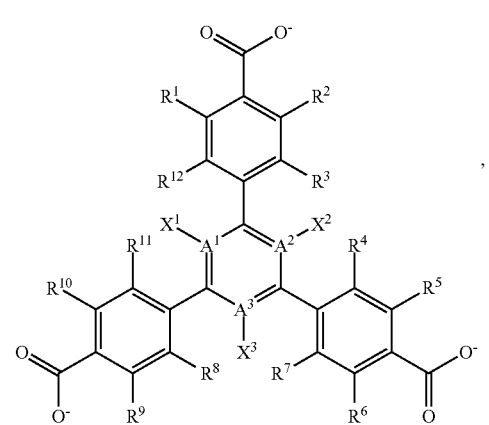
(II)

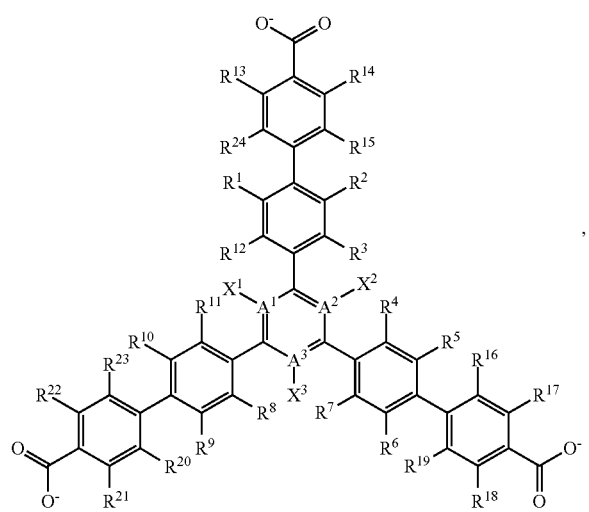
(III)

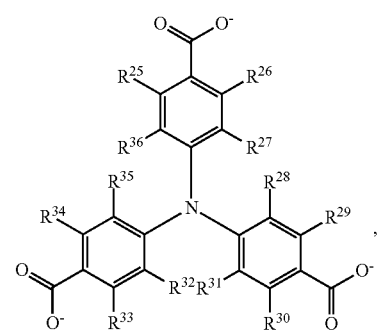
(IV)

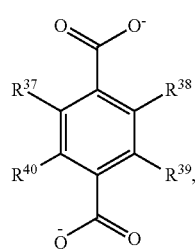
(V)

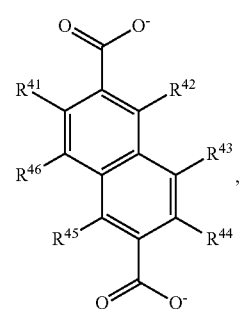
(VI)

-continued
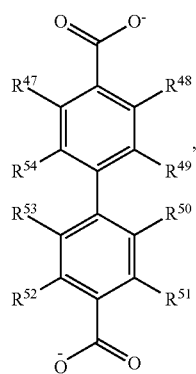
(VII)
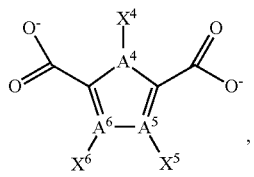
(VIII)
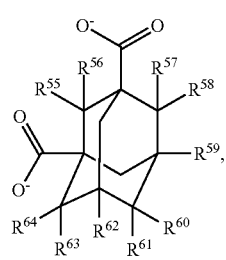
(IX)
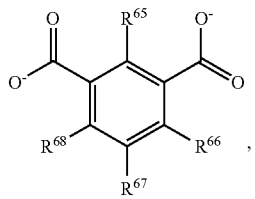
(X)
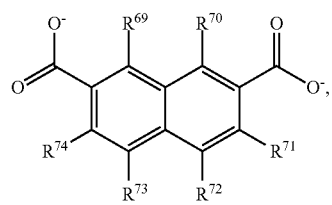
(XI)
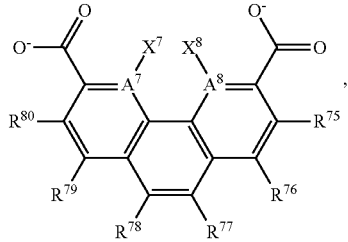
(XII)
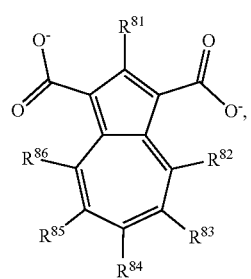
(XIII)
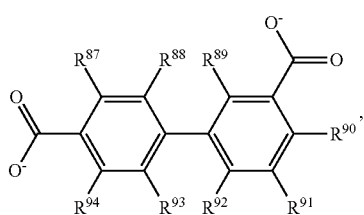
(XIV)
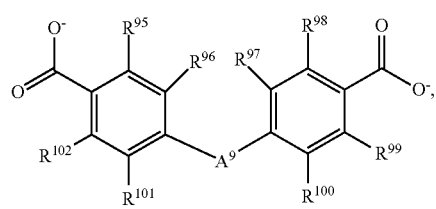
(XV)
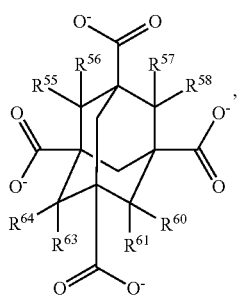
(XVI)

-continued
(XVII)
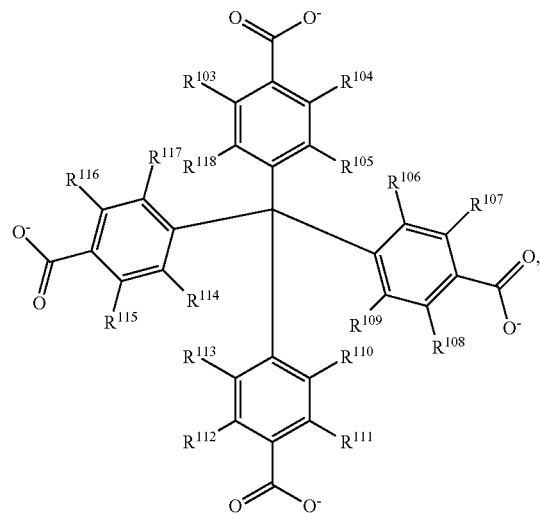
(XVIII)
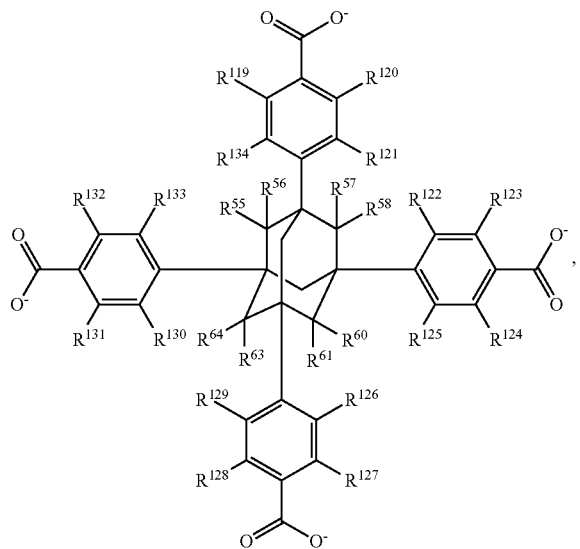
(XIX)
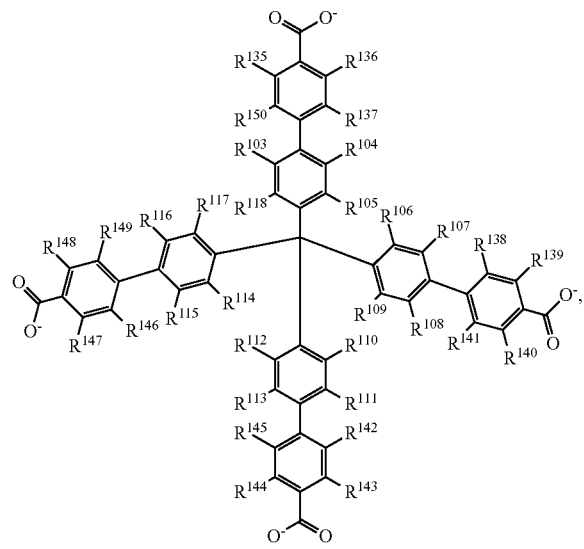
(XX)
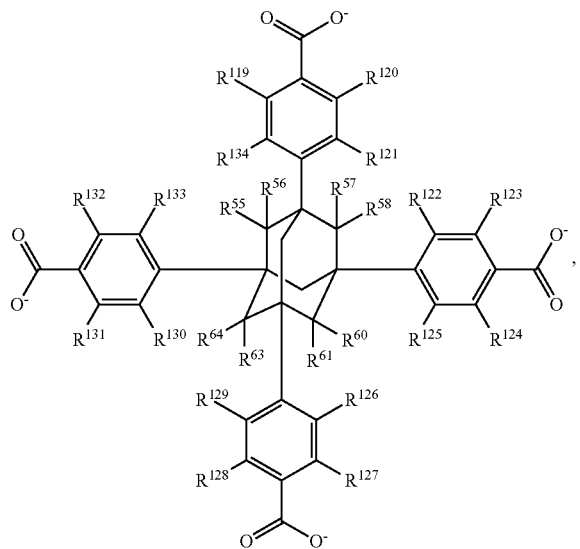

-continued

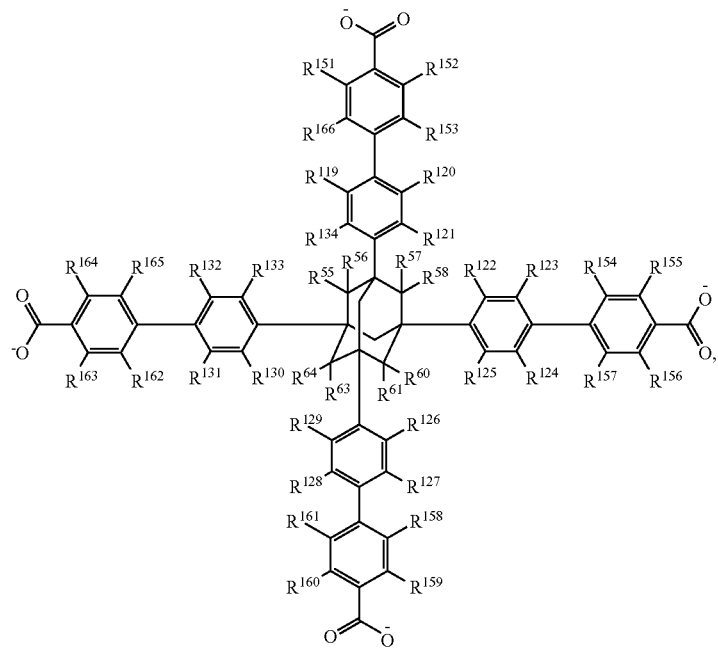

(XXI)

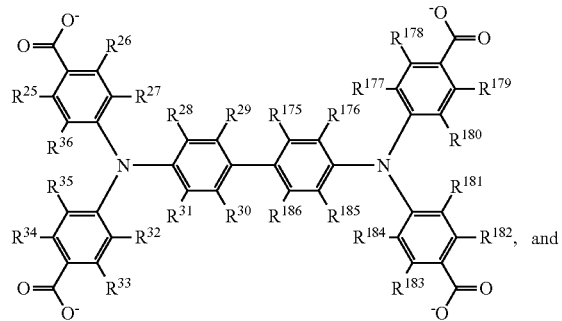

(XXII)

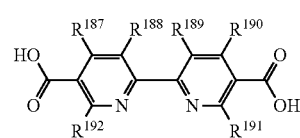

Formula XXIII wherein the carboxylate groups depicted in formulas I-XXXIII form a bond with a metal, metal ion or metal complex, and wherein, $A^1$-$A^8$ are independently a C, N, O, or S; $A^9$ is selected from

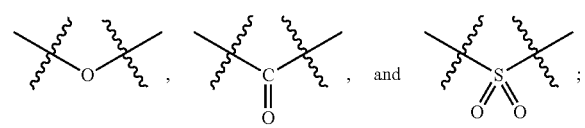

$X^1$-$X^8$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$ alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$ cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^1$-$R^{192}$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$ alkenyl, optionally substituted $(C_1$-$C_{19})$heteroalkenyl, optionally substituted $(C_1$-$C_{19})$ alkynyl, optionally substituted $(C_1$-$C_{19})$heteroalkynyl, optionally substituted $(C_1$-$C_{19})$ cycloalkyl, optionally substituted $(C_1$-$C_{19})$ cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In still a further embodiment, the organic linking ligand comprises a structured selected from the group consisting of:

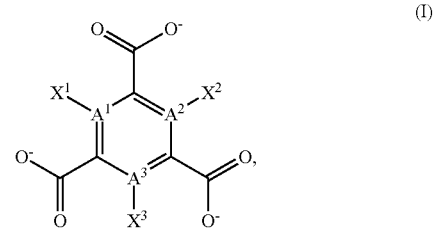

(I)

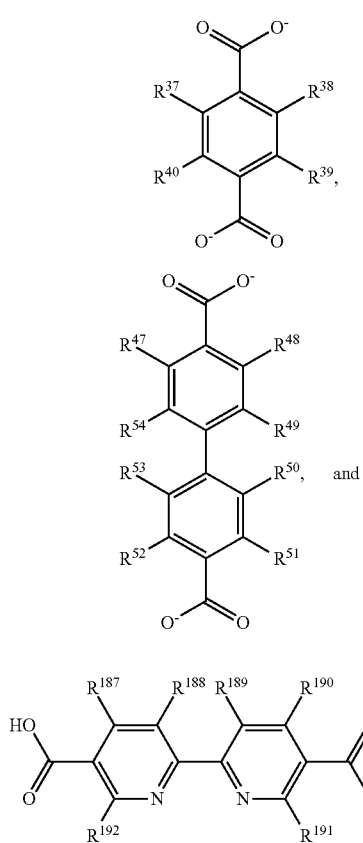

Formula XXIII wherein the carboxylic acid groups in Formula I, V, VII and XXIII undergo condensation with a metal, metal ion or metal complex, and wherein $A^1$-$A^3$ are independently a C, N, O, or S, $X^1$-$X^3$ are independently selected from H, D, optionally substituted FG, optionally substituted ($C_1$-$C_{20}$) alkyl, optionally substituted ($C_1$-$C_{19}$)heteroalkyl, optionally substituted ($C_1$-$C_{20}$)alkenyl, optionally substituted ($C_1$-$C_{19}$) heteroalkenyl, optionally substituted ($C_1$-$C_{19}$) alkynyl, optionally substituted ($C_1$-$C_{19}$)heteroalkynyl, optionally substituted ($C_1$-$C_{19}$)cycloalkyl, optionally substituted ($C_1$-$C_{19}$) cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^{37}$-$R^{40}$, $R^{47}$-$R^{54}$, $R^{187}$-$R^{192}$ are independently selected from H, D, optionally substituted FG, optionally substituted ($C_1$-$C_{20}$) alkyl, optionally substituted ($C_1$-$C_{19}$)heteroalkyl, optionally substituted ($C_1$-$C_{20}$)alkenyl, optionally substituted ($C_1$-$C_{19}$) heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In further embodiments of any of the foregoing, $R^1$-$R^{192}$ can be independently selected from:

-continued
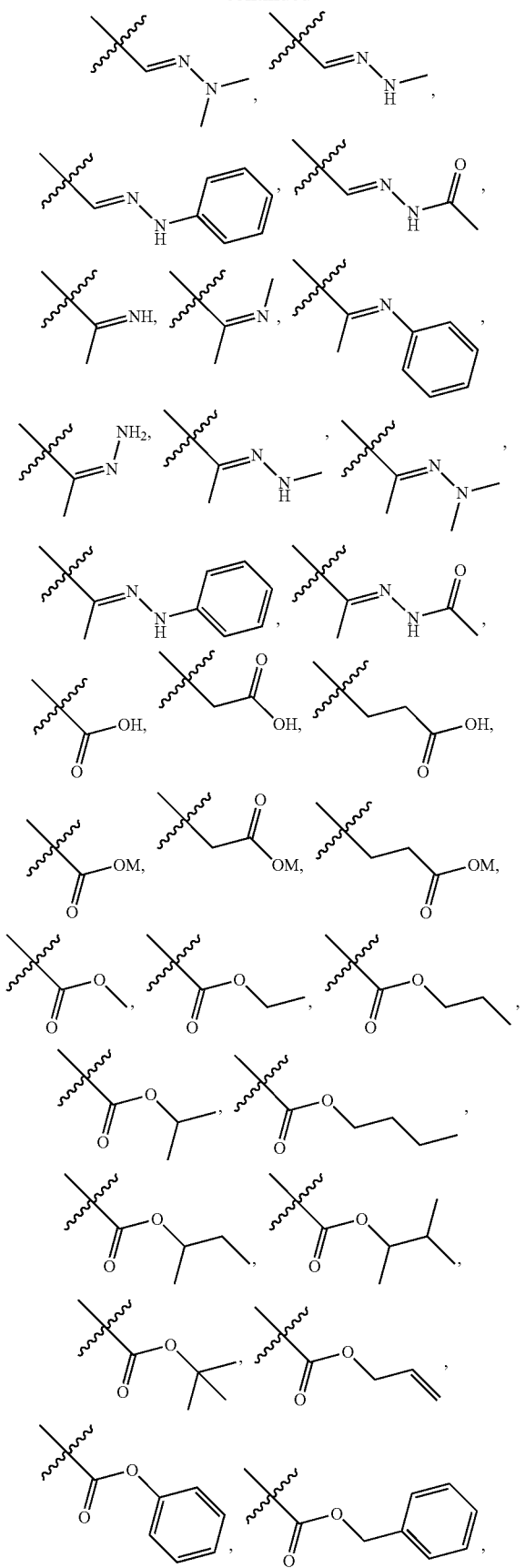
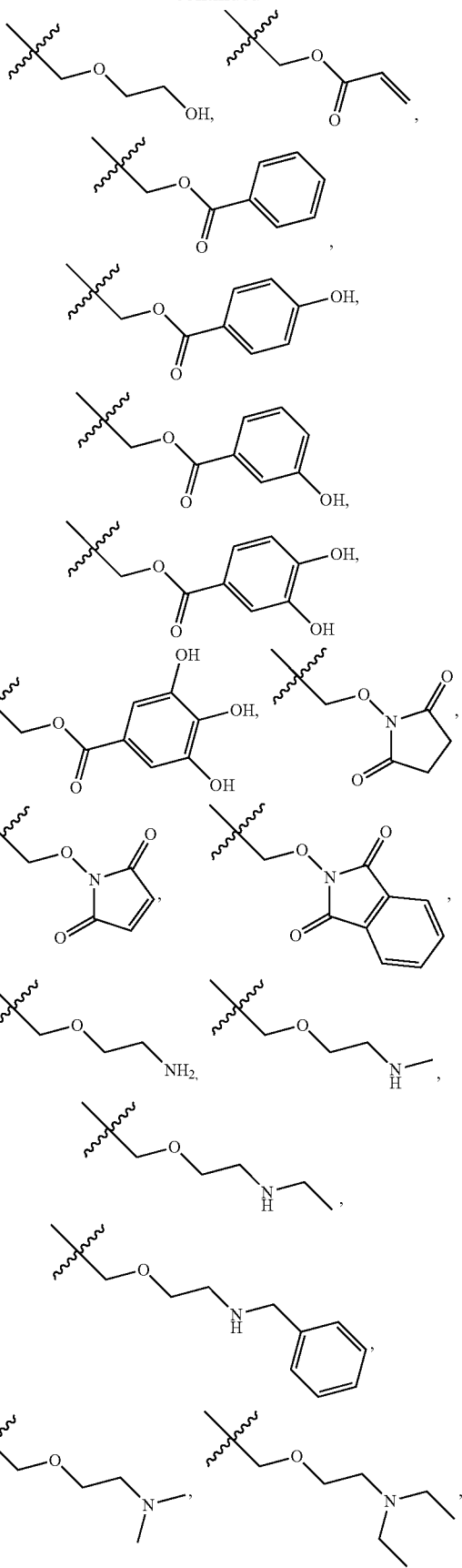

-continued
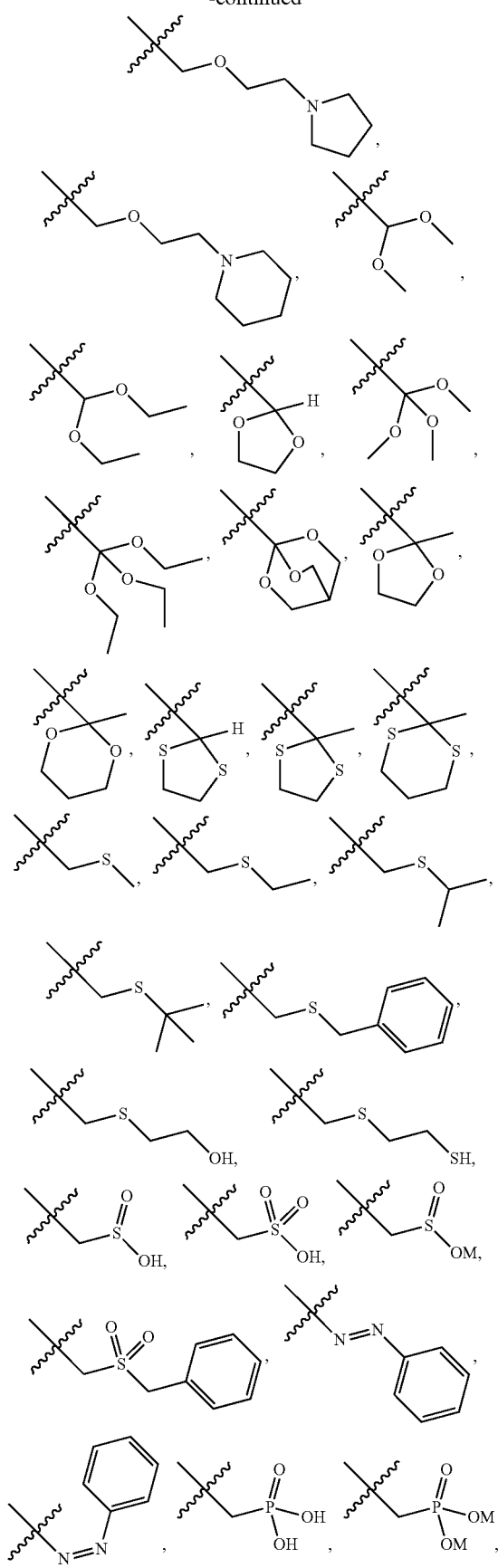
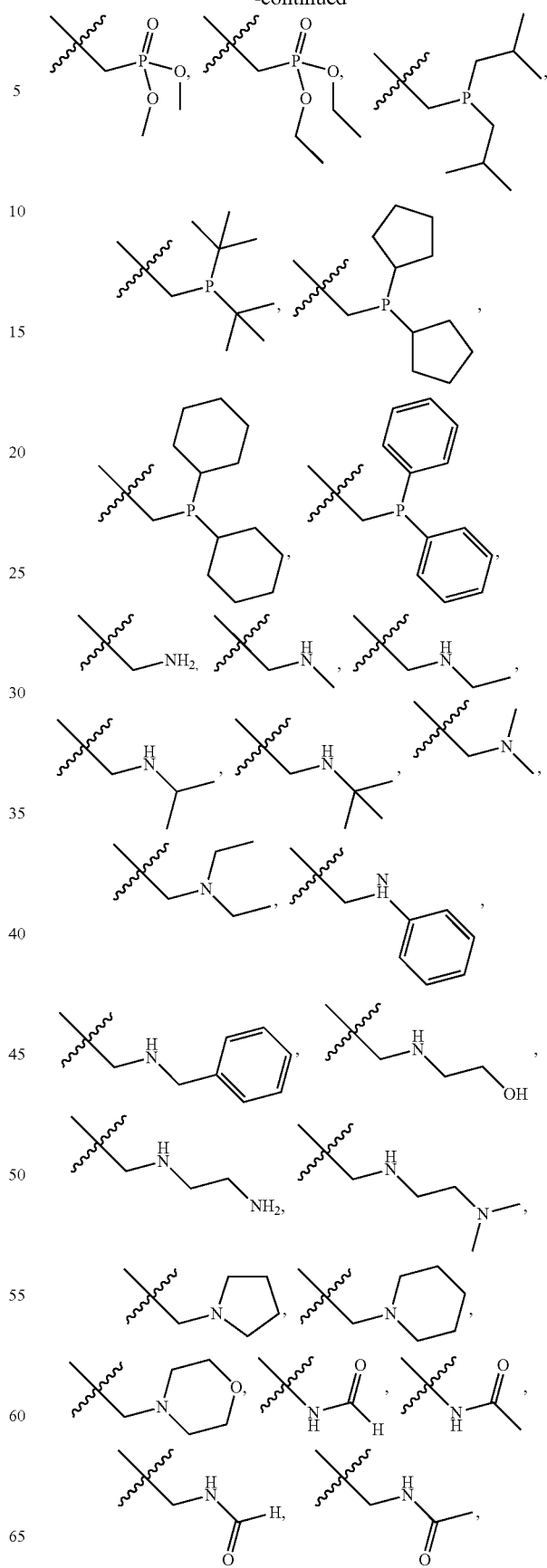

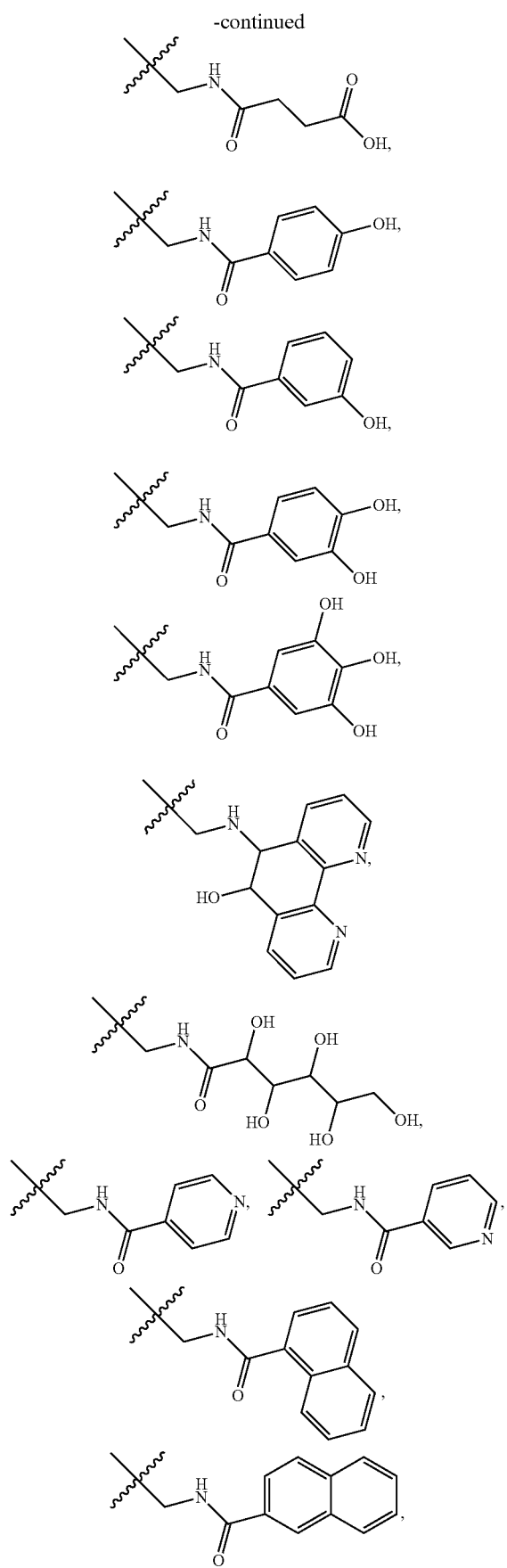
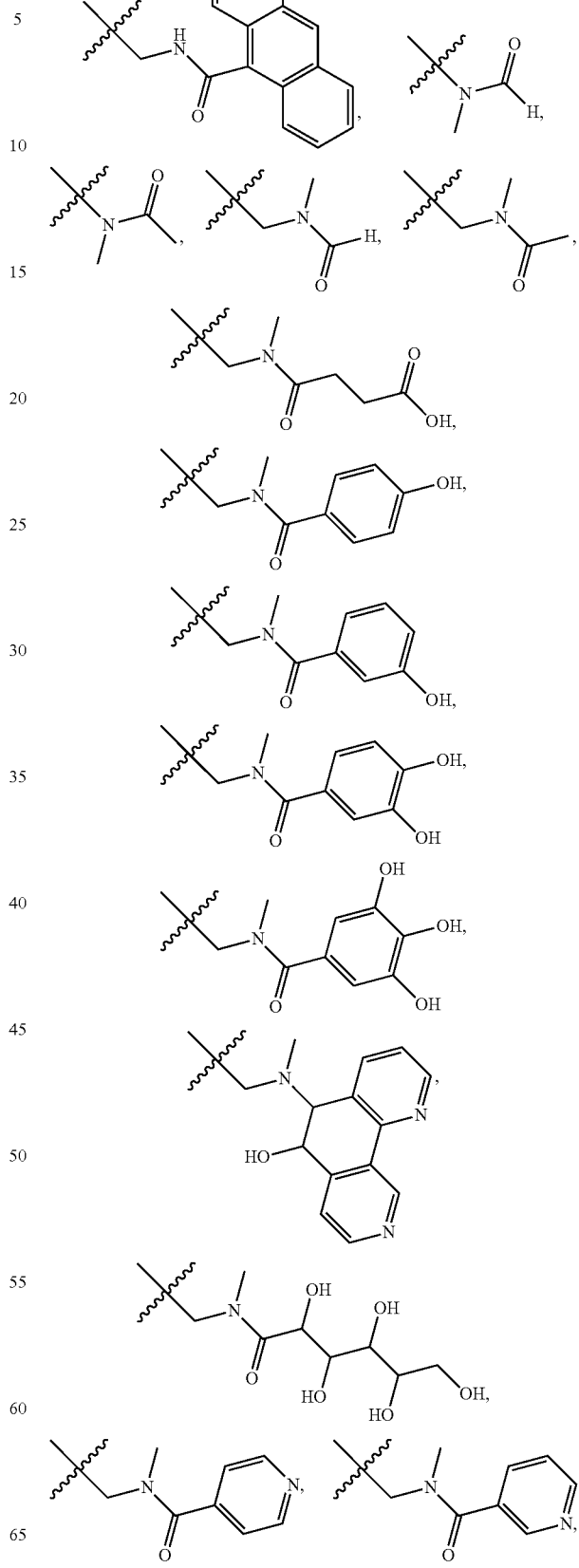

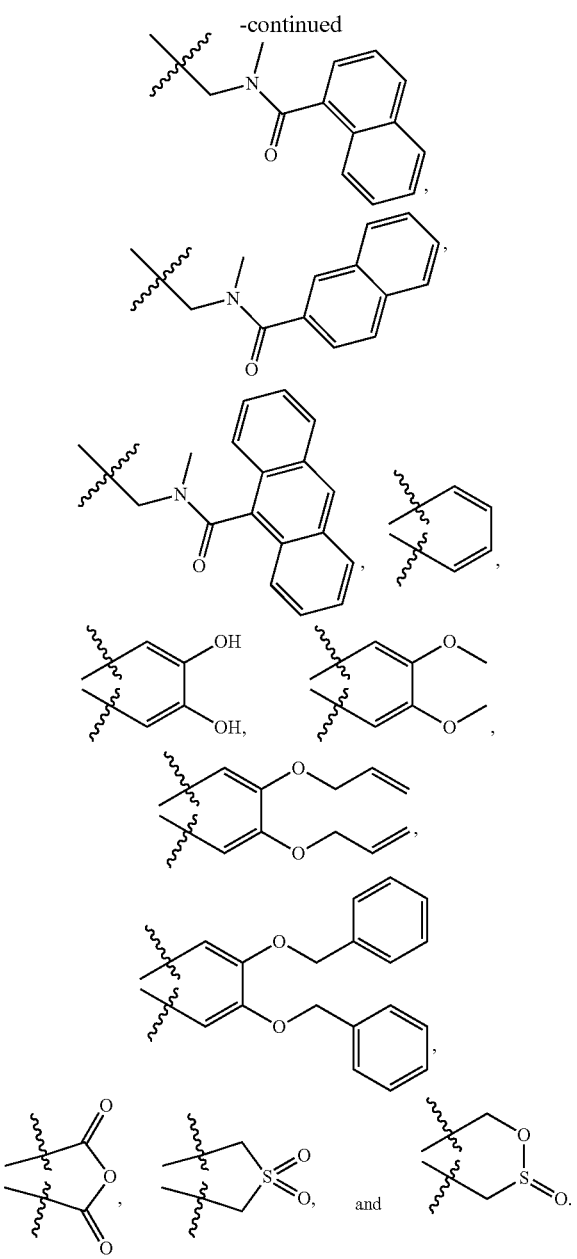

In yet another embodiment, M is a metal or metal ion selected from $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and combinations thereof, including any complexes which contain the metals or metal ions listed above, as well as any corresponding metal salt counter-anions. In a further embodiment of any of the foregoing embodiments, the MOF heterolite is comprised of a plurality of zirconium based MOFs. In yet a further embodiment of any of the foregoing, the heterolite is comprised of homogeneous MOFs. In another embodiment, the heterolite is comprised of heterogeneous MOFs. In yet another embodiment, the heterolite comprises from two to eight structurally different MOFs. In another embodiment, the structurally different MOFs have different gas sorption and/or gas separation properties. In still another embodiment, the structurally different MOFs have different catalytic properties. In another embodiment of any of the foregoing embodiments, the MOF heterolite comprises a supercrystal that is between 250 nm to 1500 nm in size. In yet another embodiment, the MOF heterolite comprises a supercrystal that is between 500 nm to 1000 nm in size. In yet another embodiment, the heterolite is nucleated with an inorganic nanoparticle.

The disclosure also provides a method to produce a MOF heterolite of any proceeding claim comprising, preparing a MOF reaction mixture comprising metal or metal ions, organic molecules comprising multidentate functional groups, a suitable modulating agent, and a suitable solvent system; heating at a predetermined temperature and sufficient period of time to allow for crystal formation; preparing a colloidal solution comprising the MOFs; assembling the MOFs from the colloidal solution into MOF heterolites by using accelerated sedimentation in a centrifuge or gravimetric sedimentation in a pipette assembly. In one embodiment, a surfactant is added to colloidal solution. In a further embodiment, the surfactant is selected from polyvinylpyrrolidone, sodium dodecyl sulfate, cetrimonium bromide and triton X-100.

DETAILED DESCRIPTION

Figure 1:
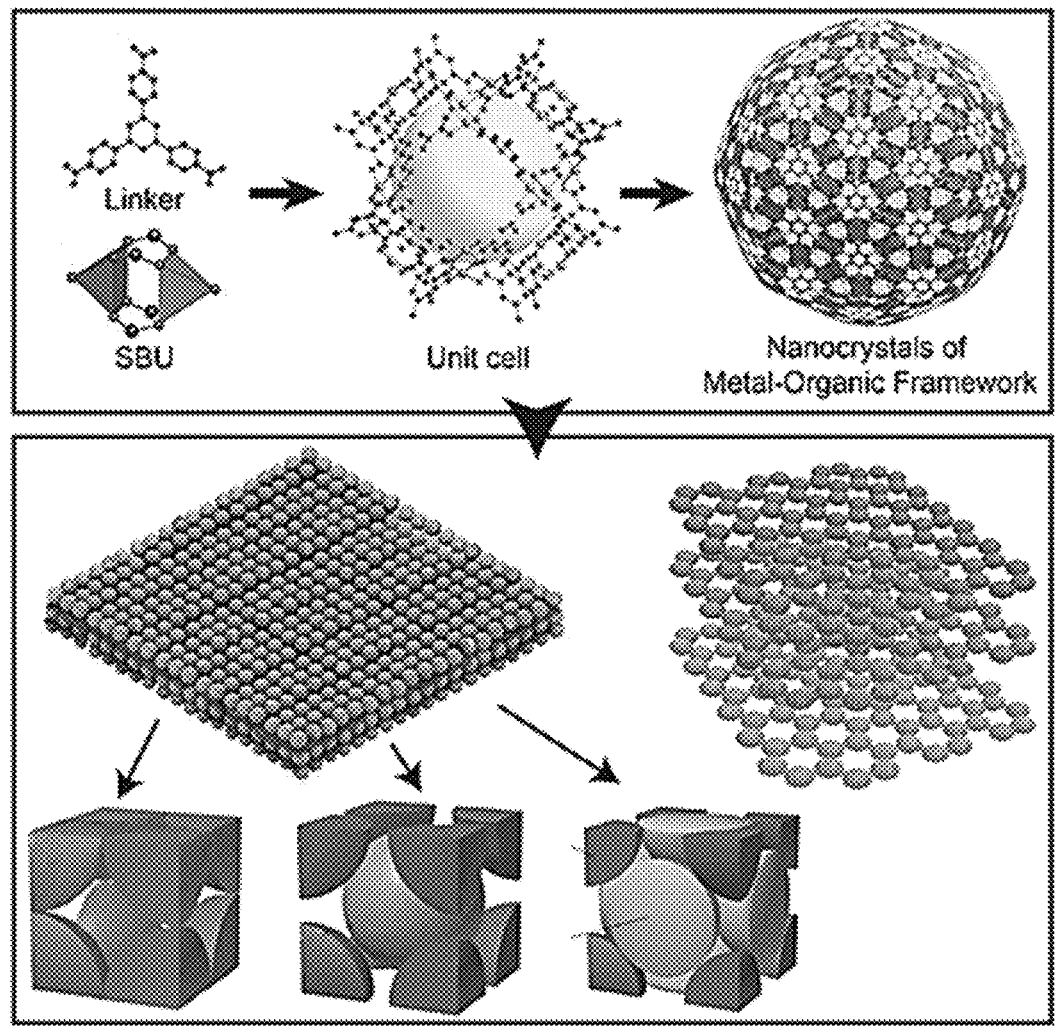
FIG. 1 presents a diagram showing a formation of nanocrystals of metal organic frameworks (top) and their mesoscopic assembly (bottom).
Figure 2:
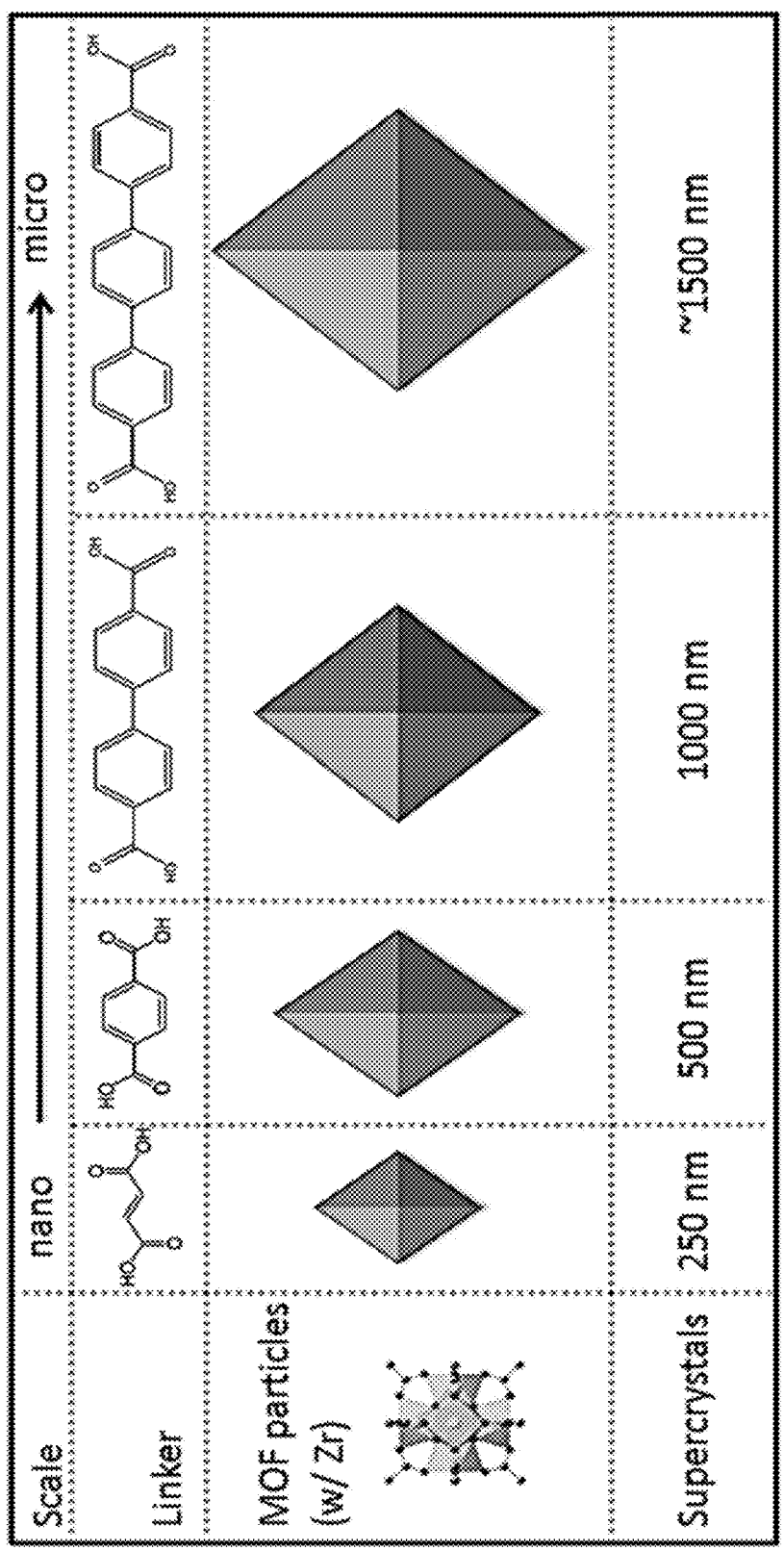
FIG. 2 shows examples of supercrystals having different sizes of MOF supercrystals constructed from different linker lengths.
Figure 3:
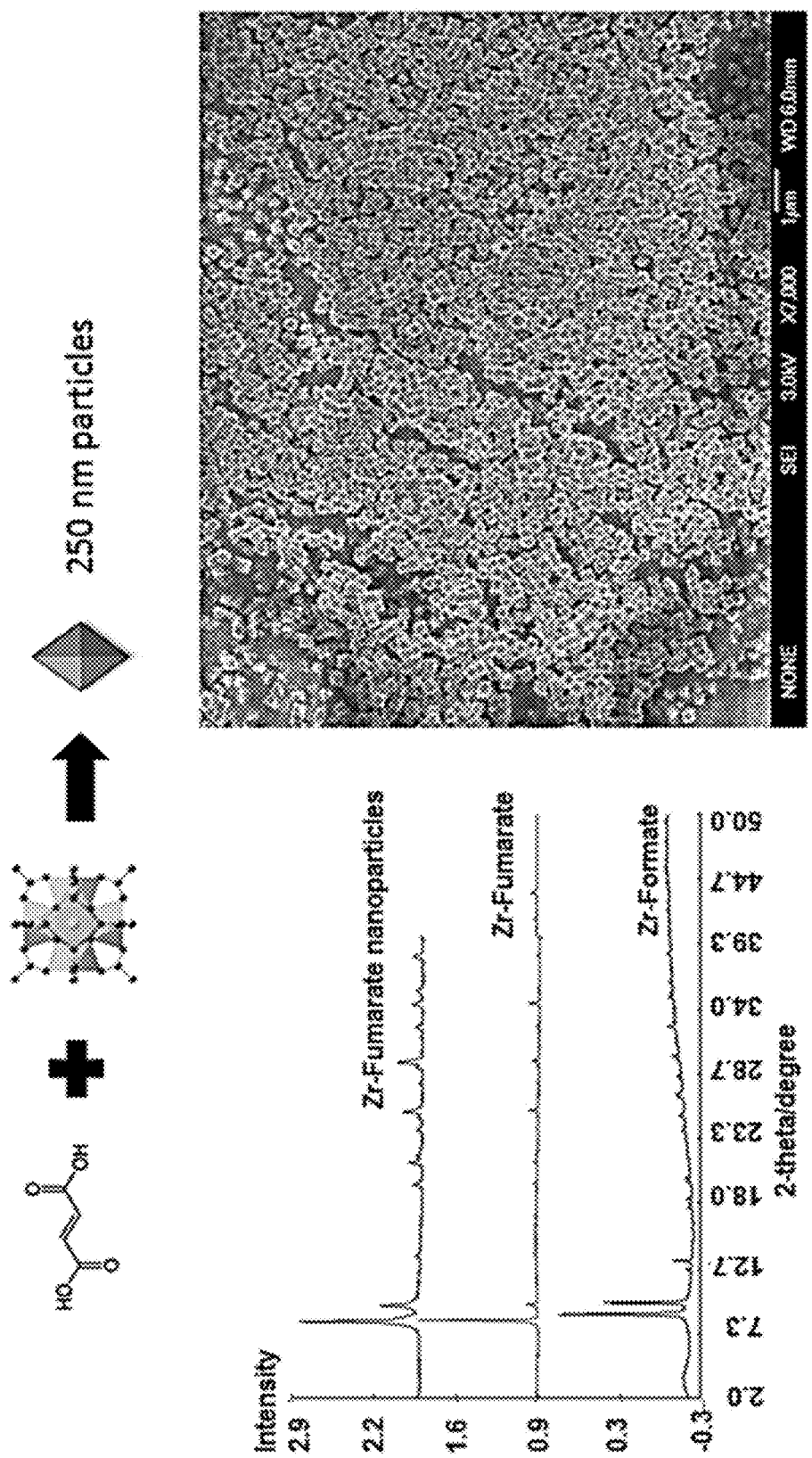
FIG. 3 demonstrates that by using the methods of the disclosure, MOF-801 heterolites can be produced as 250 nm sized nanocrystals with homogeneous size and morphology. (Top) generalized scheme to make MOF-801 supercrystals with homogeneous size distribution (heterolites). (Bottom left) powder X-ray patterns of MOF-801 heterolites. (Bottom right) scanning electron image (SEM) of a MOF-801 heterolite.
Figure 4:
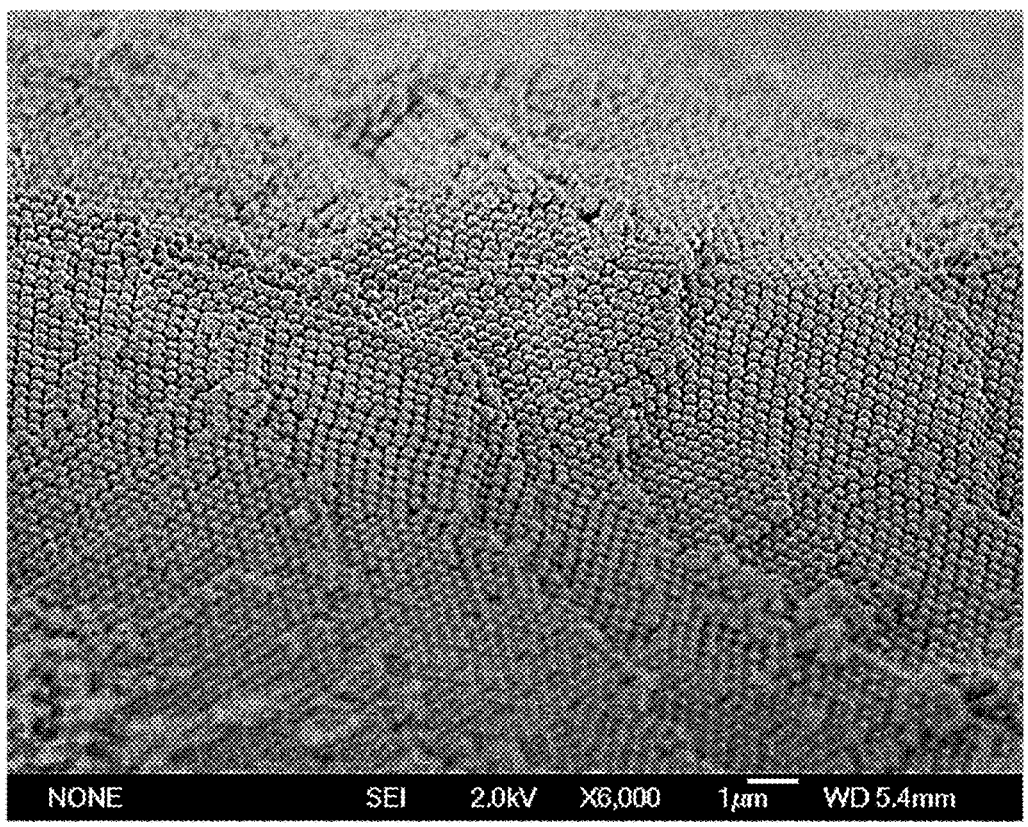
FIG. 4 presents a magnified SEM image of a MOF-801 heterolite.
Figure 5:
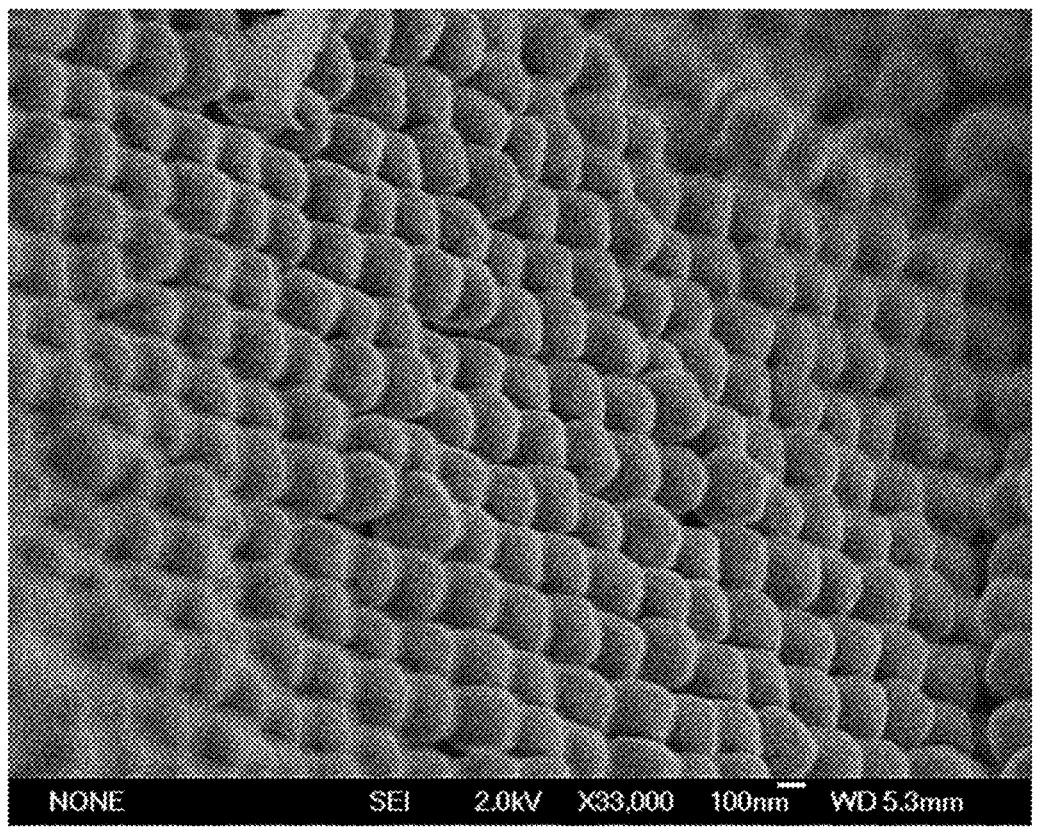
FIG. 5 presents a highly magnified SEM image of a MOF-801 heterolite.
Figure 6:
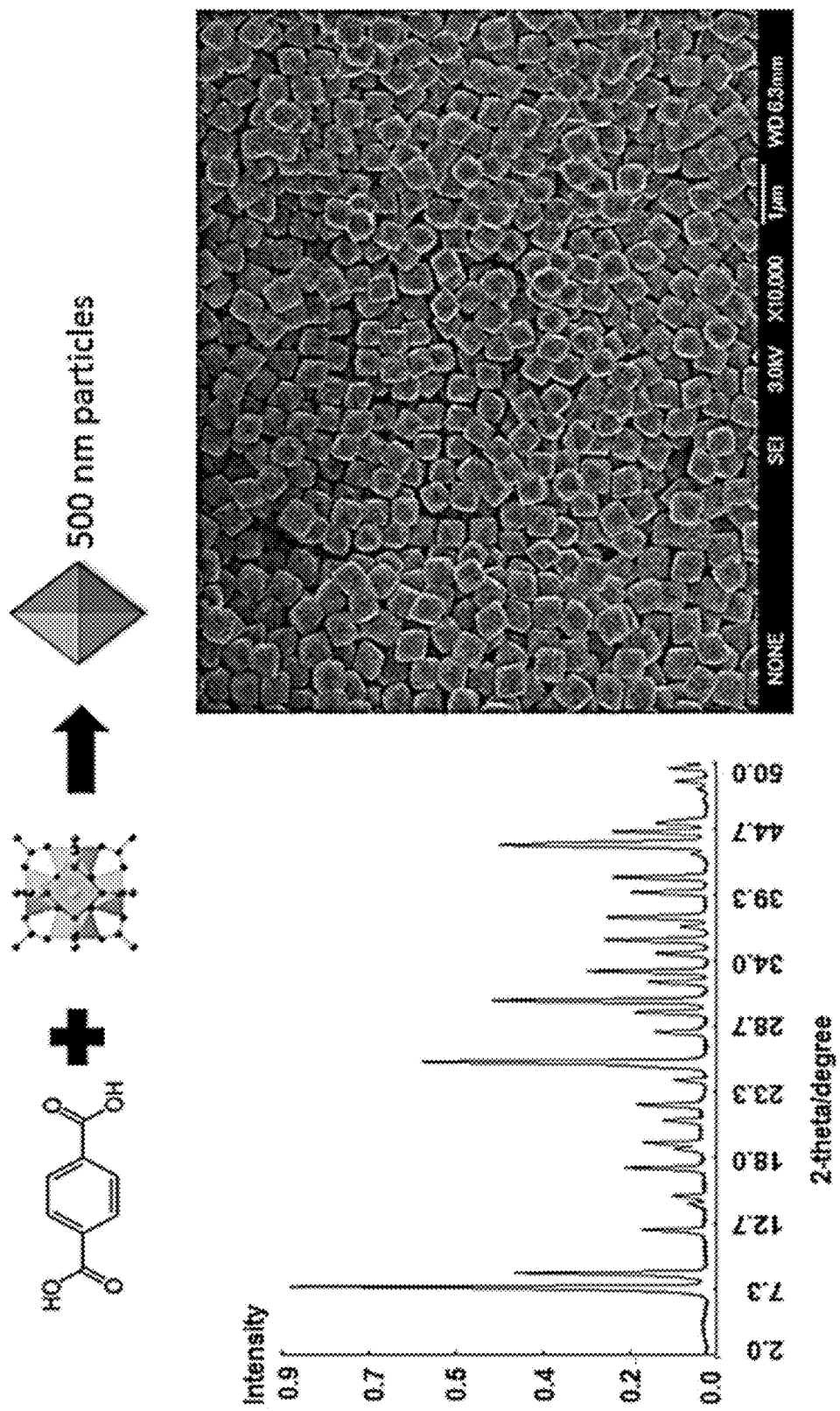
FIG. 6 demonstrates that by using the methods of the disclosure, Uio-66 MOF heterolites can be produced as 500 nm sized nanocrystals with homogeneous size distribution. (Top) generalized scheme to make Uio-66 MOF heterolite. (Bottom left) X-ray pattern of Uio-66 MOF heterolite. (Bottom right) scanning electron image (SEM) of a Uio-66 MOF heterolite.
Figure 7:
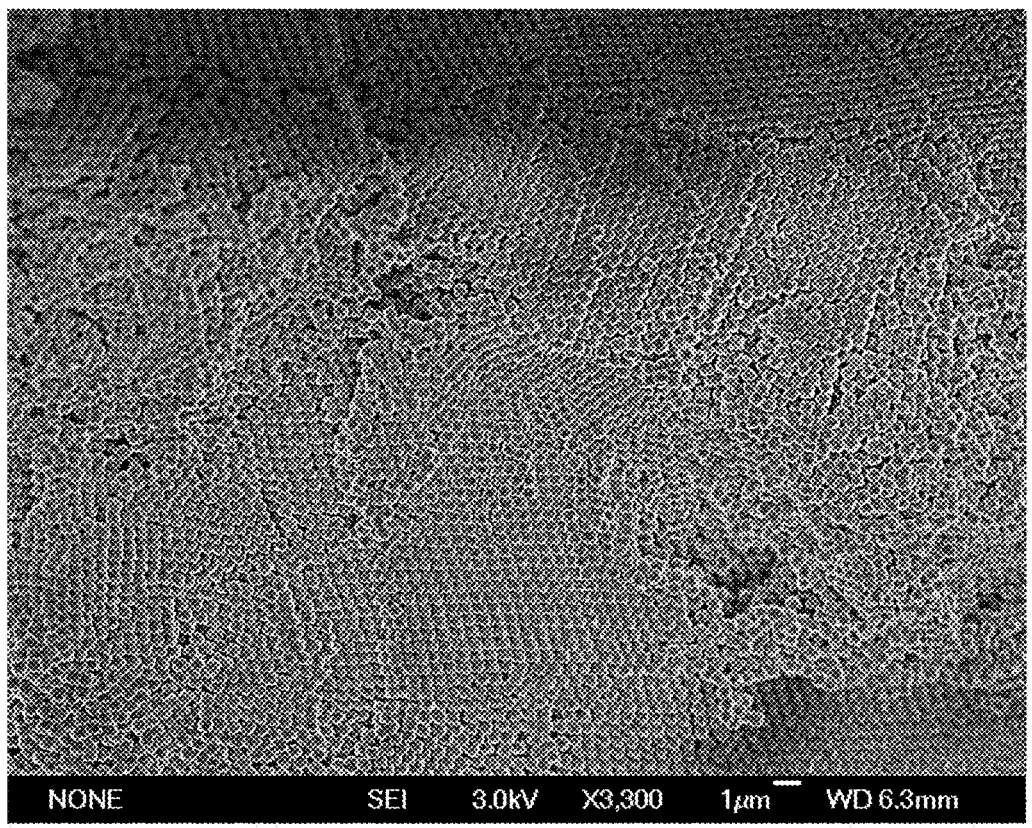
FIG. 7 presents a magnified SEM image of a Uio-66 MOF heterolite.
Figure 8:
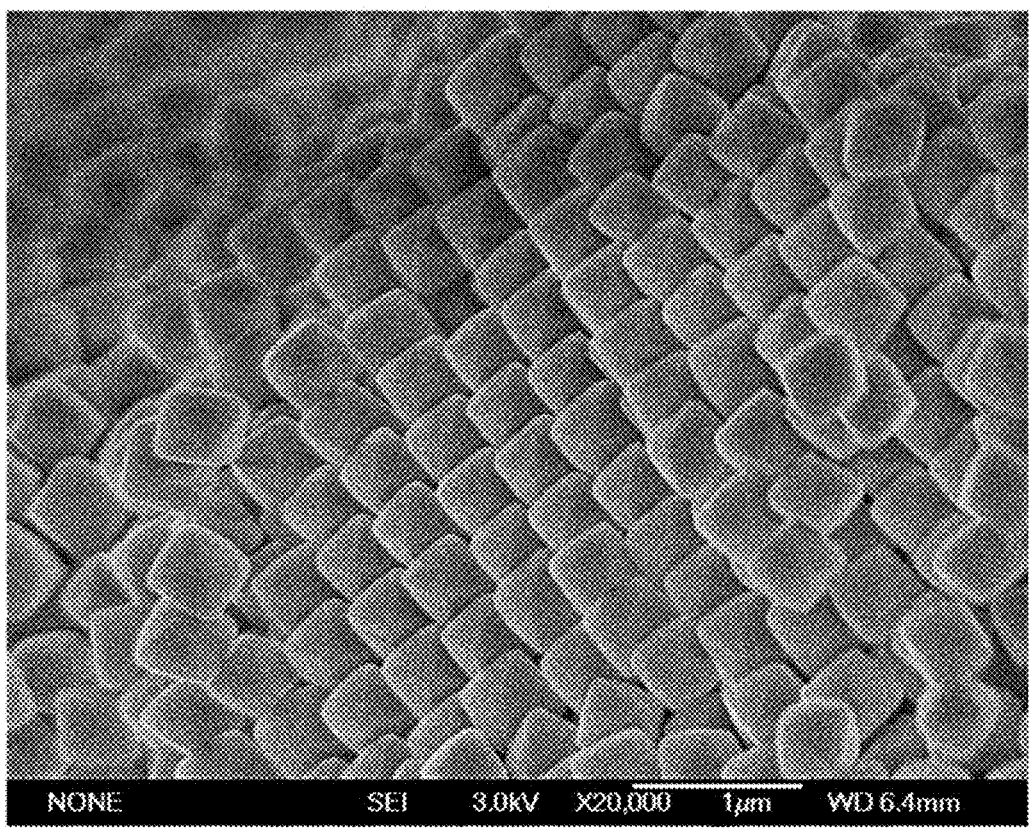
FIG. 8 presents a highly magnified SEM image of a Uio-66 MOF heterolite.
Figure 9:
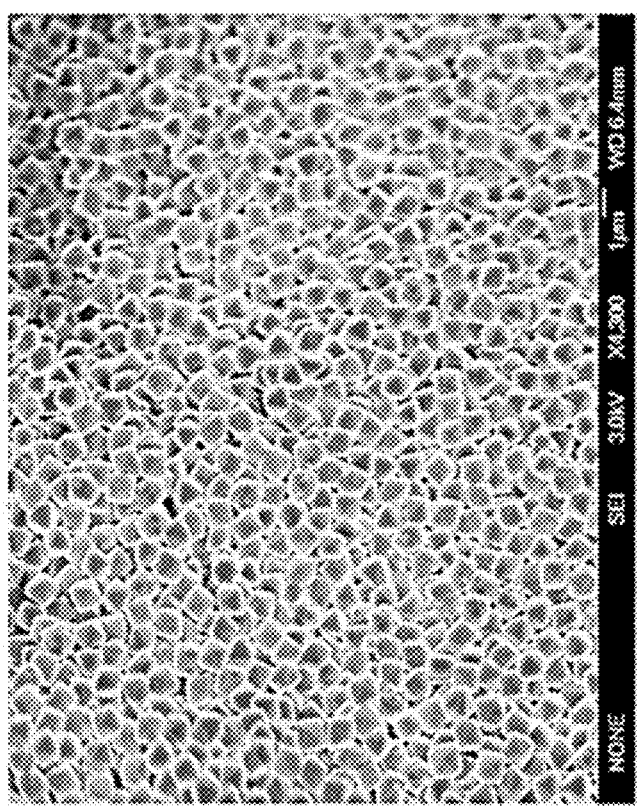
FIG. 9 demonstrates that by using the methods of the disclosure, Uio-67 MOF heterolites can be produced as 1 µm sized nanocrystals with homogeneous size distribution. (Top) generalized scheme to make a Uio-67 MOF heterolite. (Bottom left) powder X-ray pattern of a Uio-67 MOF heterolite. (Bottom right) scanning electron image (SEM) of a Uio-67 MOF heterolite.
Figure 9:
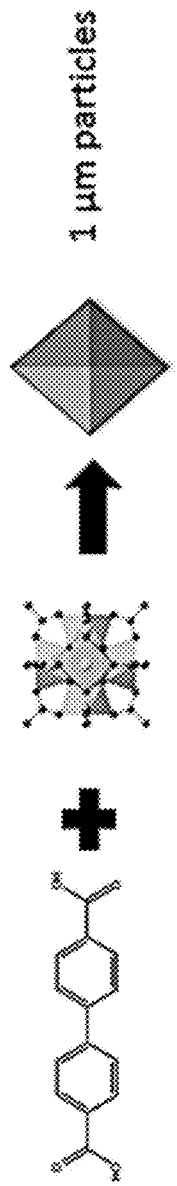
Figure 9:
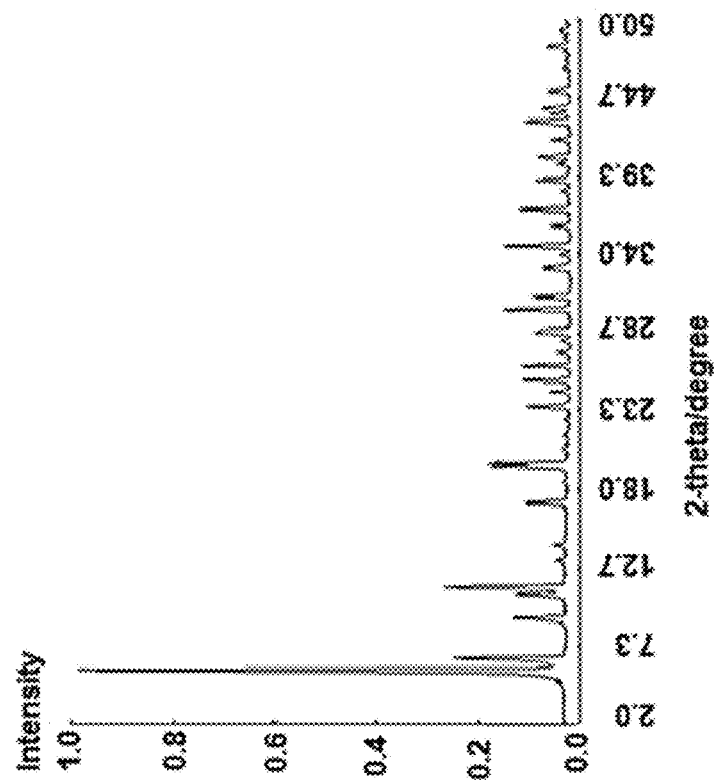
Figure 10:
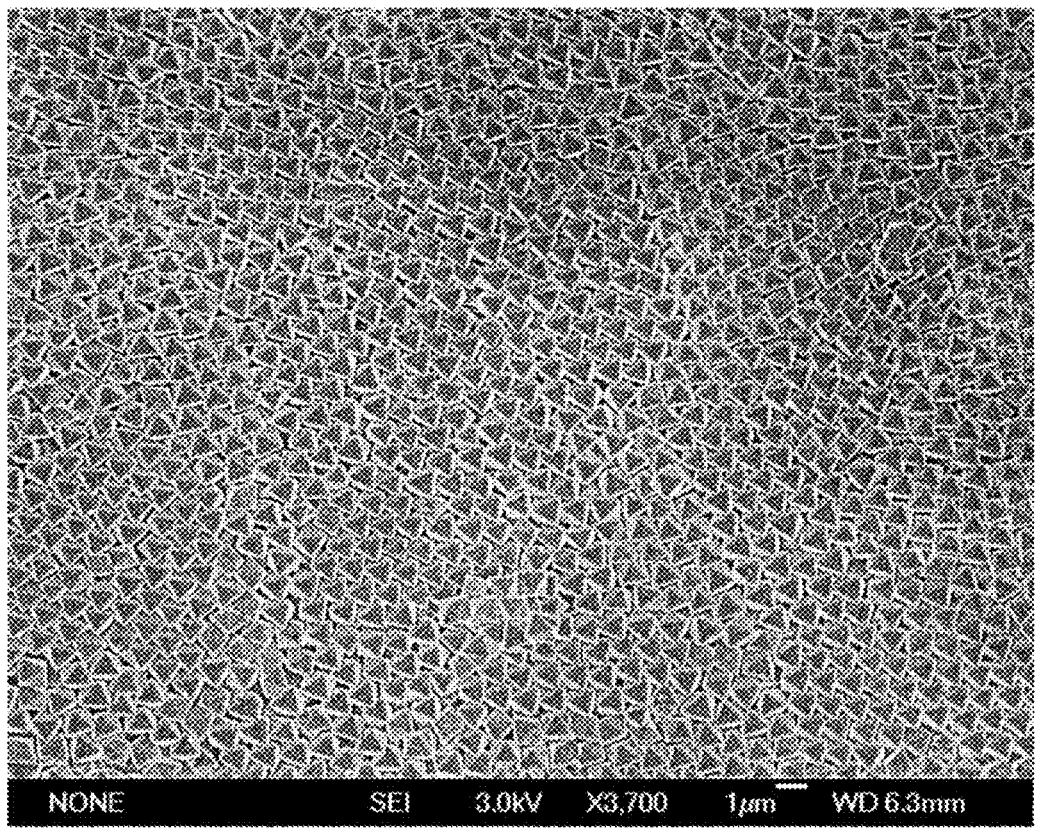
FIG. 10 presents a magnified SEM image of a Uio-67 MOF heterolite.
Figure 11:
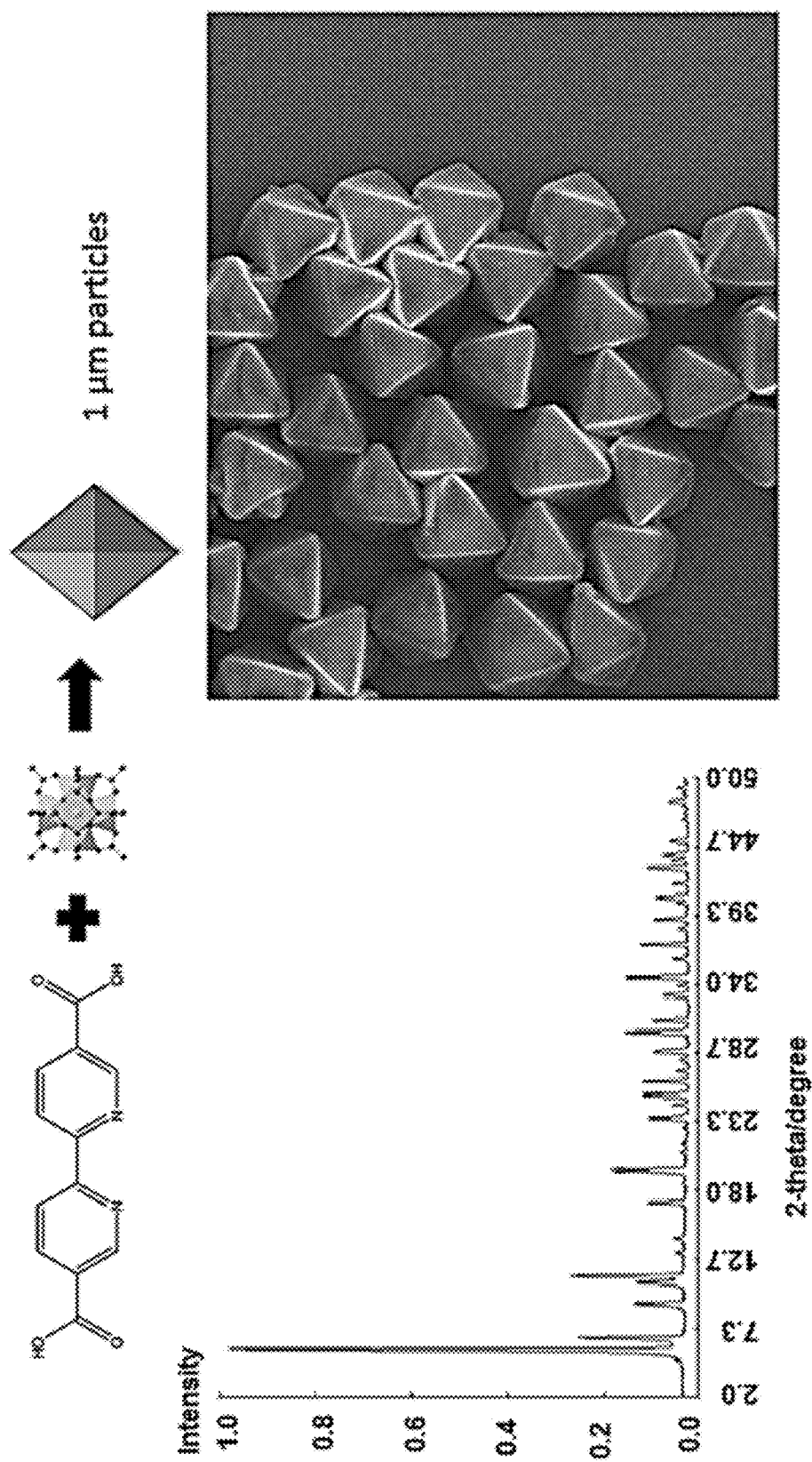
FIG. 11 demonstrates that by using the methods of the disclosure, MOF-867 heterolites can be produced as 1 µm sized nanocrystals with homogeneous size distribution. (Top) generalized scheme to make MOF-808 supercrystals. (Bottom left) powder X-ray pattern of a MOF-867 heterolite. (Bottom right) scanning electron image (SEM) of a MOF-867 heterolites.
Figure 12:
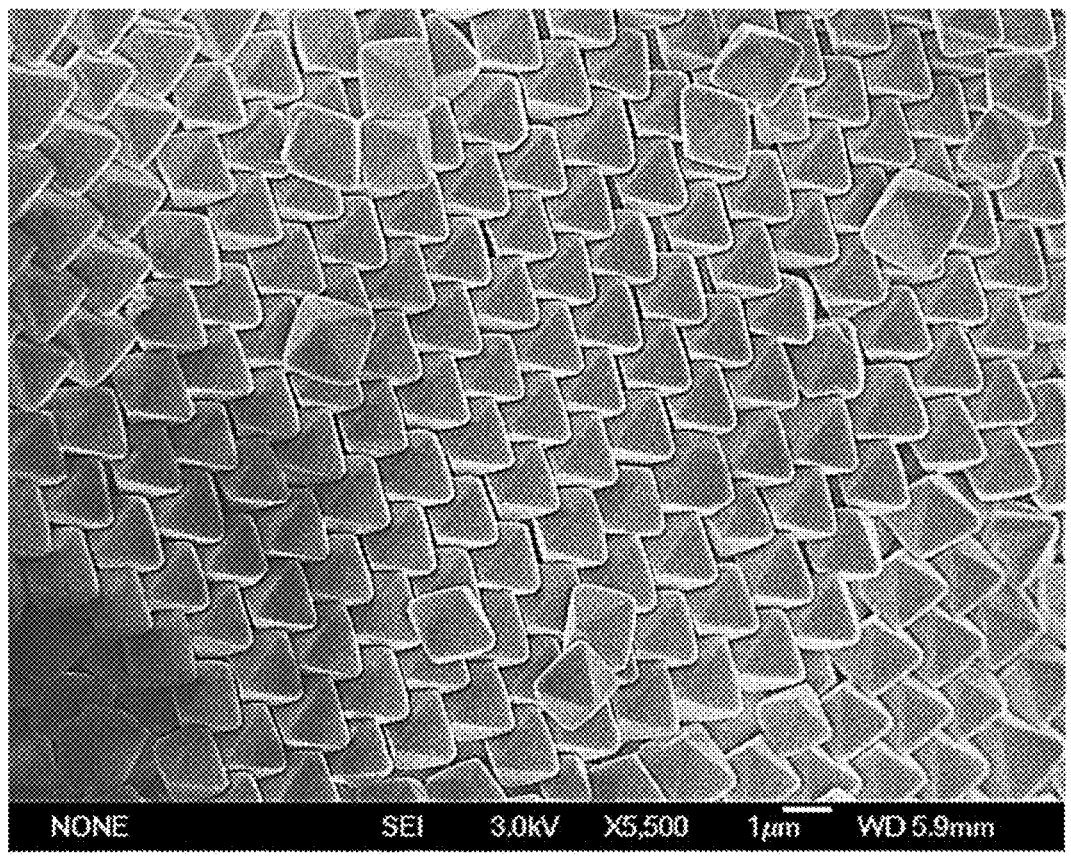
FIG. 12 presents a magnified SEM image of a MOF-867 heterolite.
Figure 13:
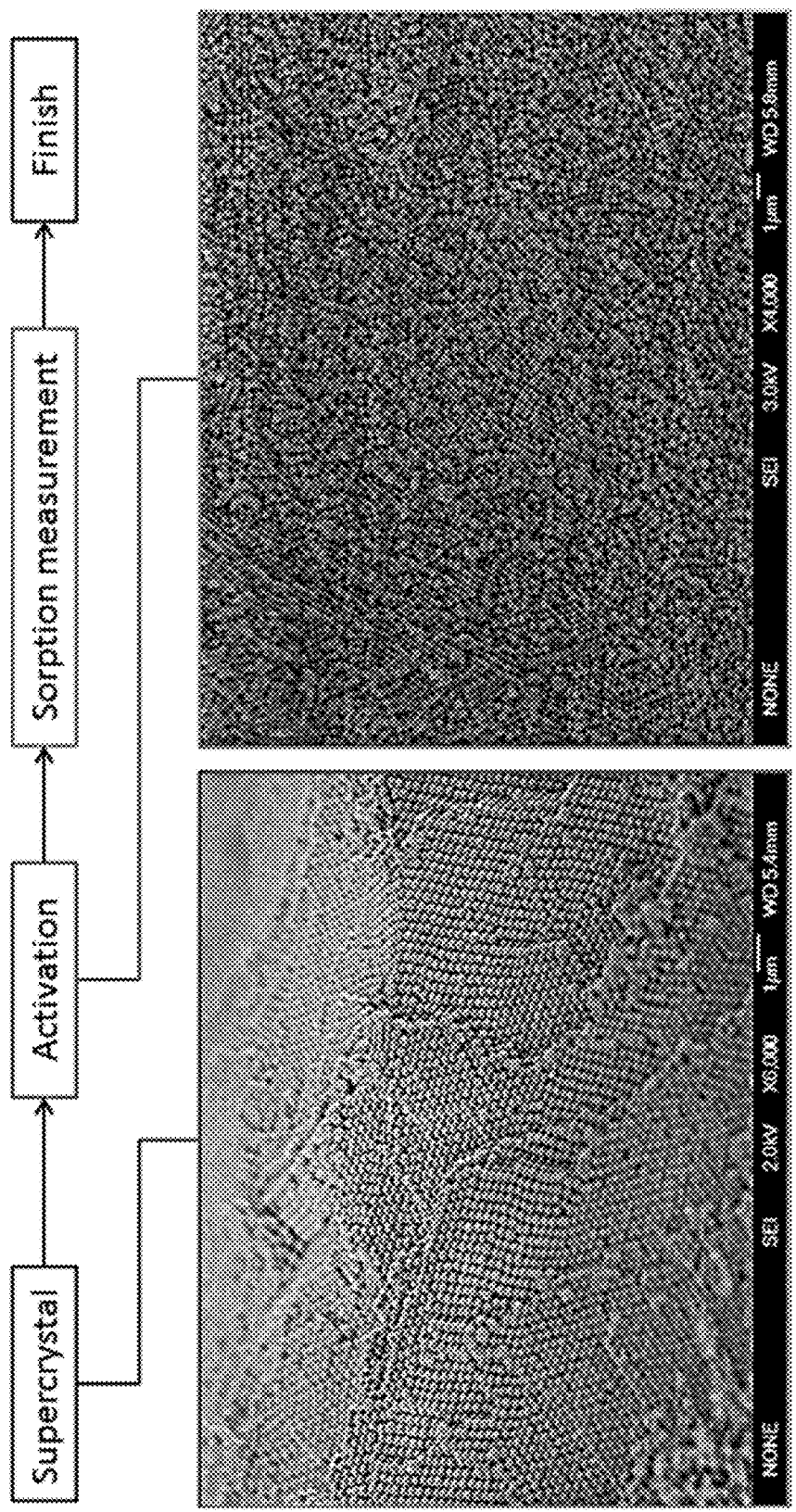
FIG. 13 presents a method for characterizing MOF-801 heterolites. (Top) generalized scheme for the activation of a MOF-801 heterolite and the subsequent sorption studies of the activated heterolite. (Bottom left) SEM image of a MOF-801 heterolite supercrystals as synthesized. (Bottom right) SEM image of MOF-801 heterolite supercrystals after activation.
Figure 14:
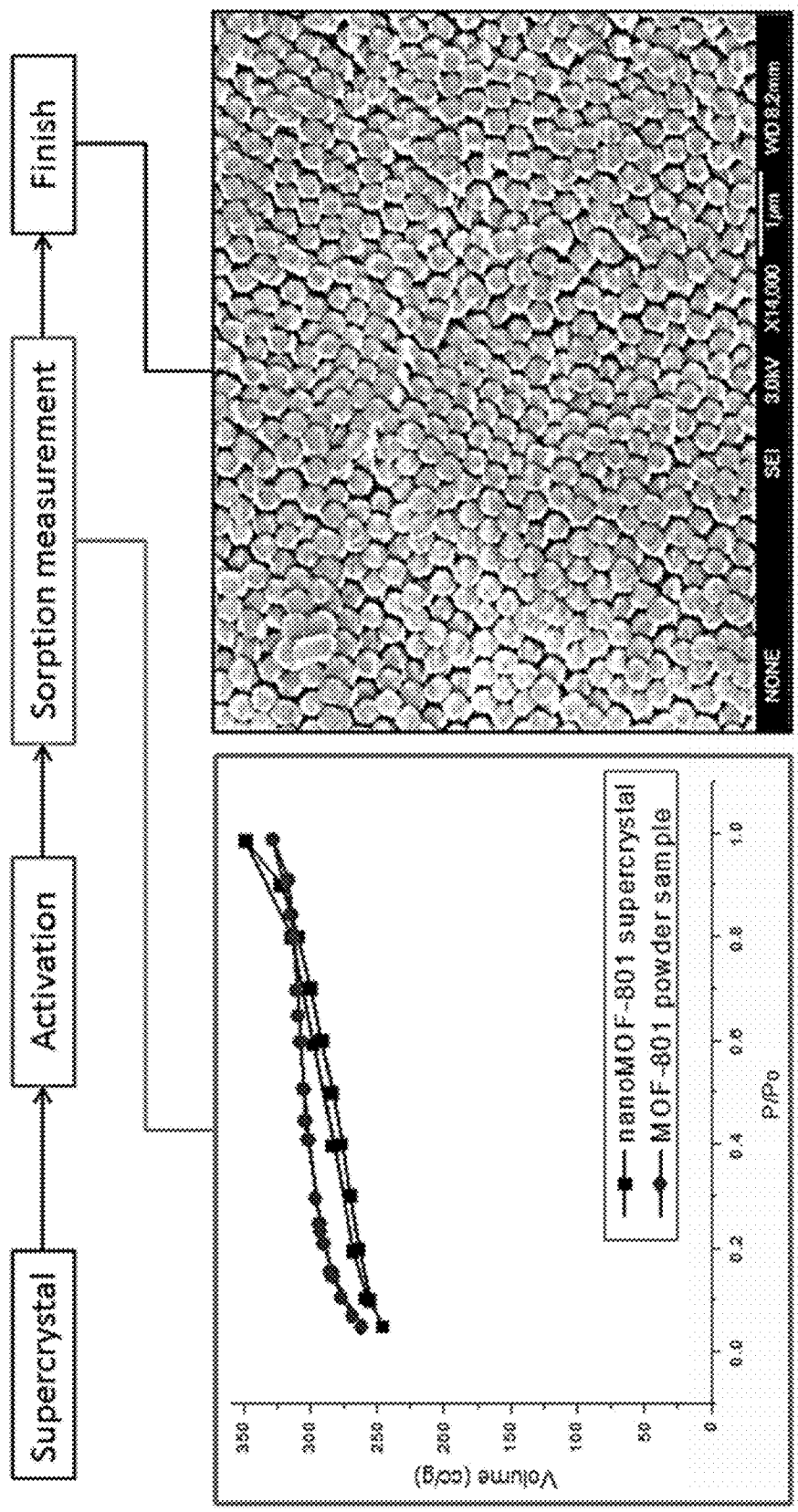
FIG. 14 presents a method for characterizing MOF-801 heterolite. (Top) generalized scheme for the activation of MOF-801 heterolite supercrystals and the subsequent sorption studies of the activated supercrystals. (Bottom left) Isotherm studies looking at the sorption characteristics of MOF-801 heterolite supercrystals. (Bottom right) SEM image of MOF-801 heterolite supercrystals post sorption studies.
Figure 15:
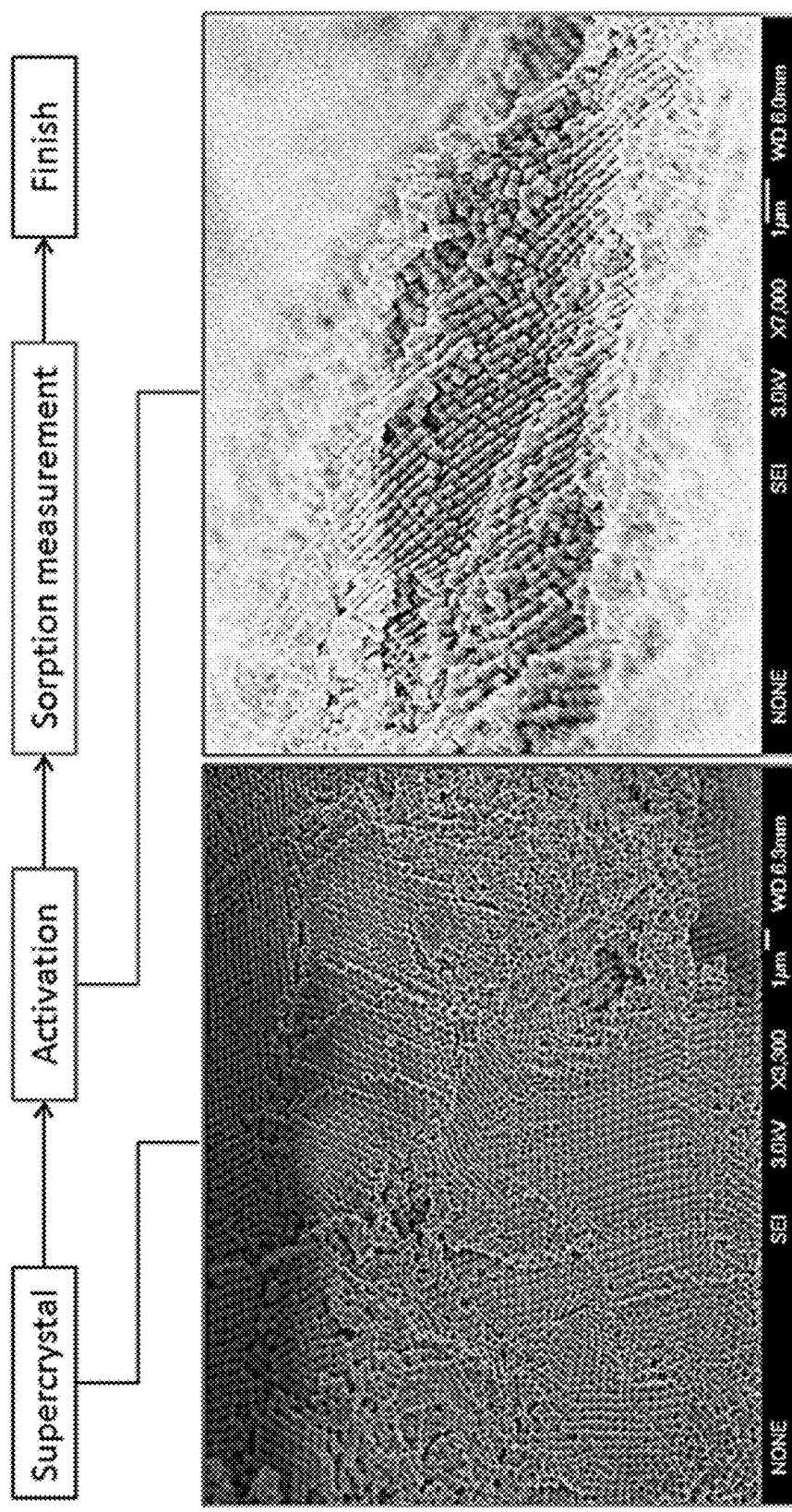
FIG. 15 presents a method for characterizing Uio-66 heterolite supercrystals. (Top) generalized scheme for the activation of Uio-66 heterolite supercrystals and the subsequent sorption studies of the activated supercrystals. (Bottom left) SEM image of Uio-66 heterolite supercrystals as synthesized. (Bottom right) SEM image of Uio-66 heterolite supercrystals after activation.
Figure 16:
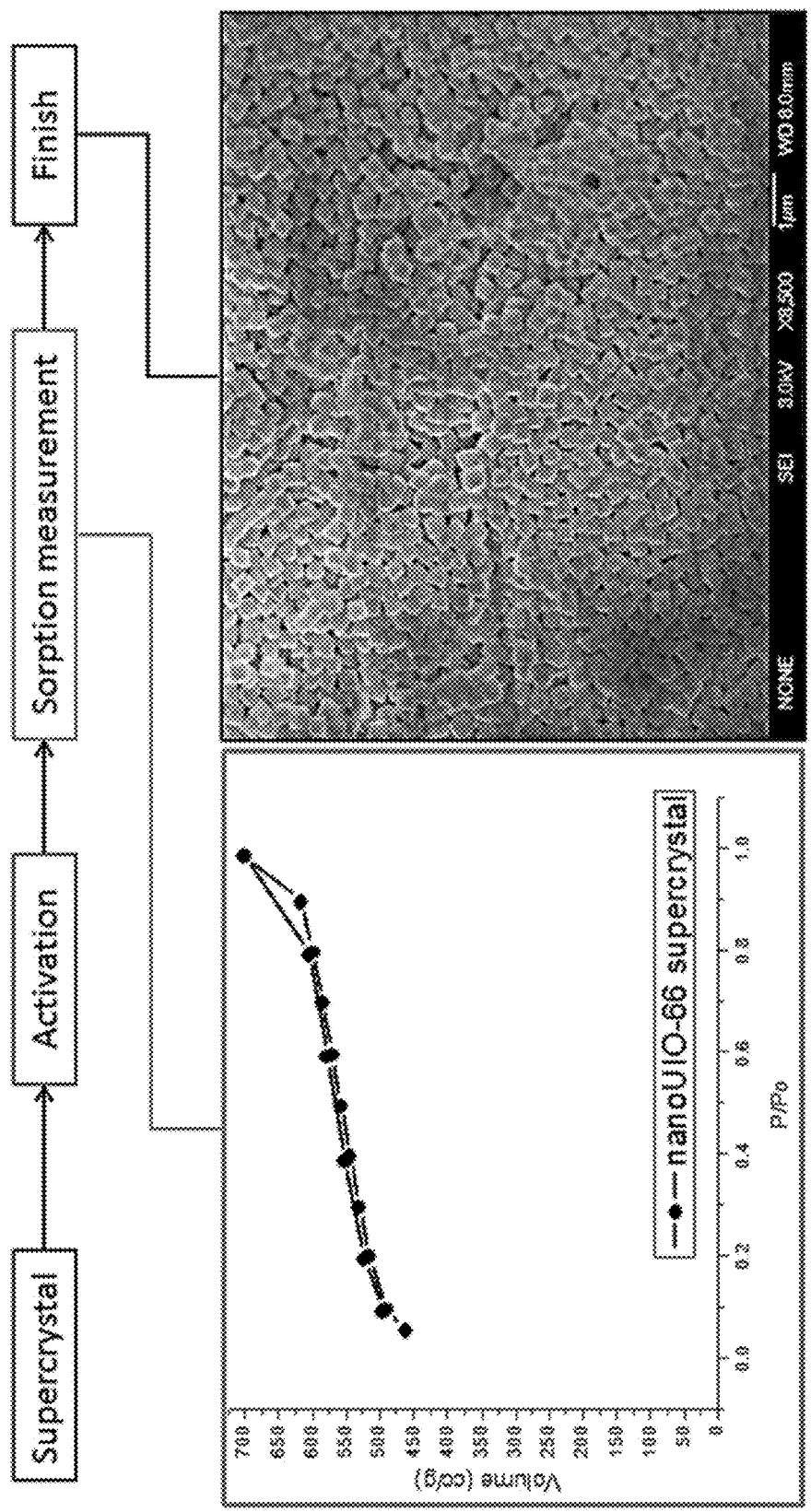
FIG. 16 presents a method for characterizing Uio-66 heterolite supercrystals. (Top) generalized scheme for the activation of Uio-66 heterolite supercrystals and the subsequent sorption studies of the activated supercrystals. (Bottom left) Isotherm studies looking at the sorption characteristics of Uio-66 heterolite supercrystals. (Bottom right) SEM image of Uio-66 heterolite supercrystals post sorption studies.
Figure 17:
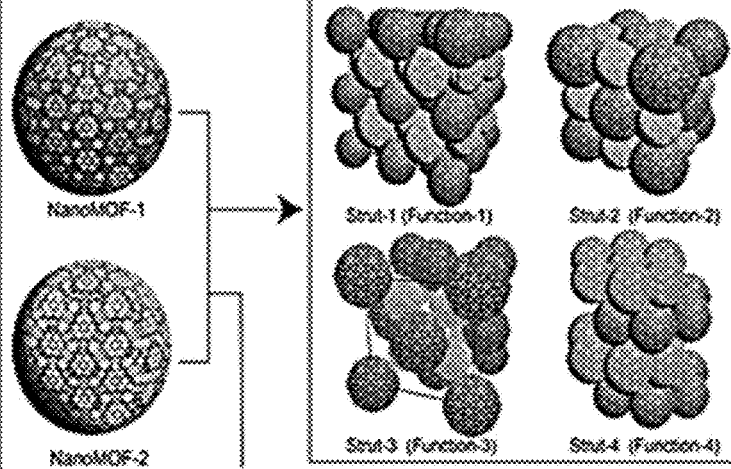
FIG. 17 provides diagrams demonstrating the assembly of mesoscopic materials which are comprised of ordered superlattices of multiple heterogeneous microporous metal-organic framework (MOF) nanocrystals using co-sedimentation or ligand-directed self-assembly.
Figure 17:
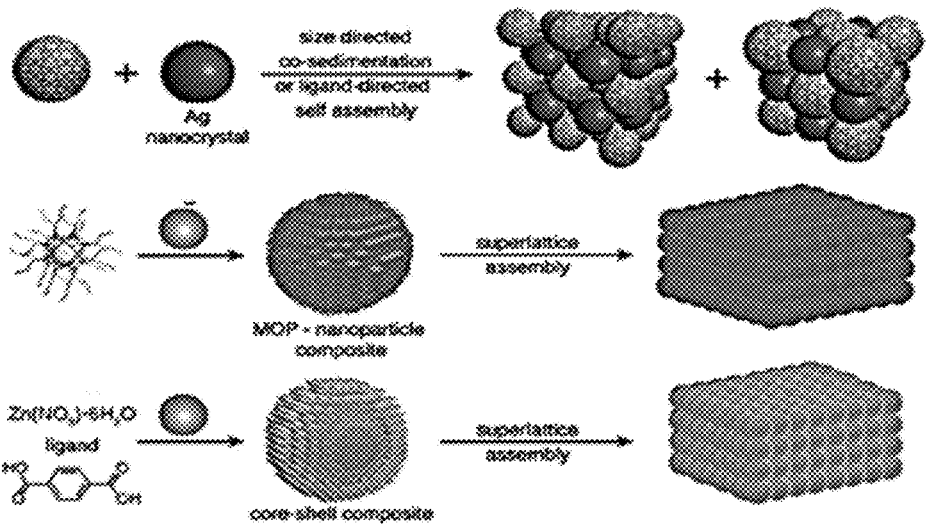
Figure 18:
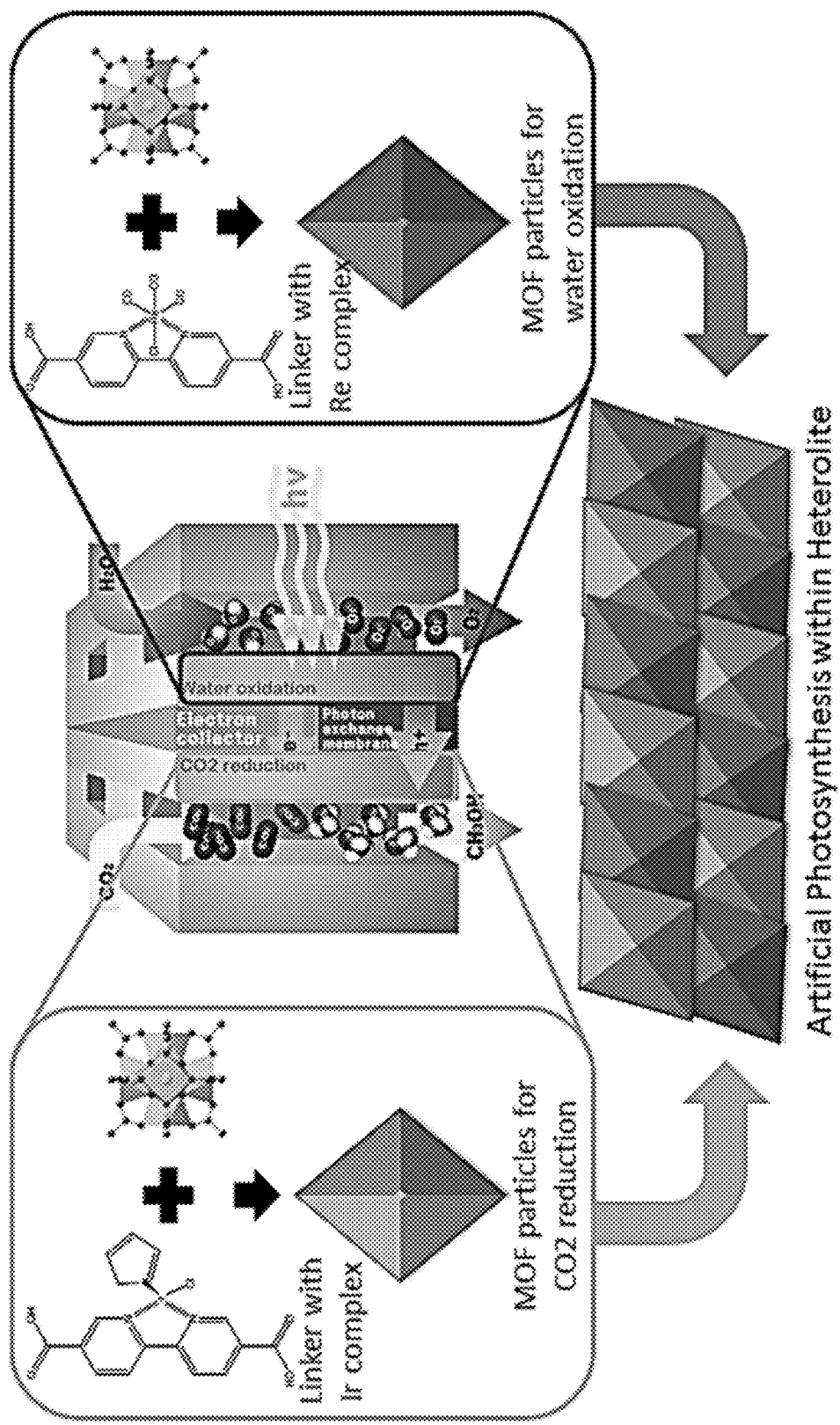
FIG. 18 presents an application of MOF heterolites for artificial photosynthesis. MOFs that reduce $CO_2$ can be joined with MOFs which oxidize water to form a MOF heterolite superlattice that can be used to perform artificial photosynthesis.
Figure 19:
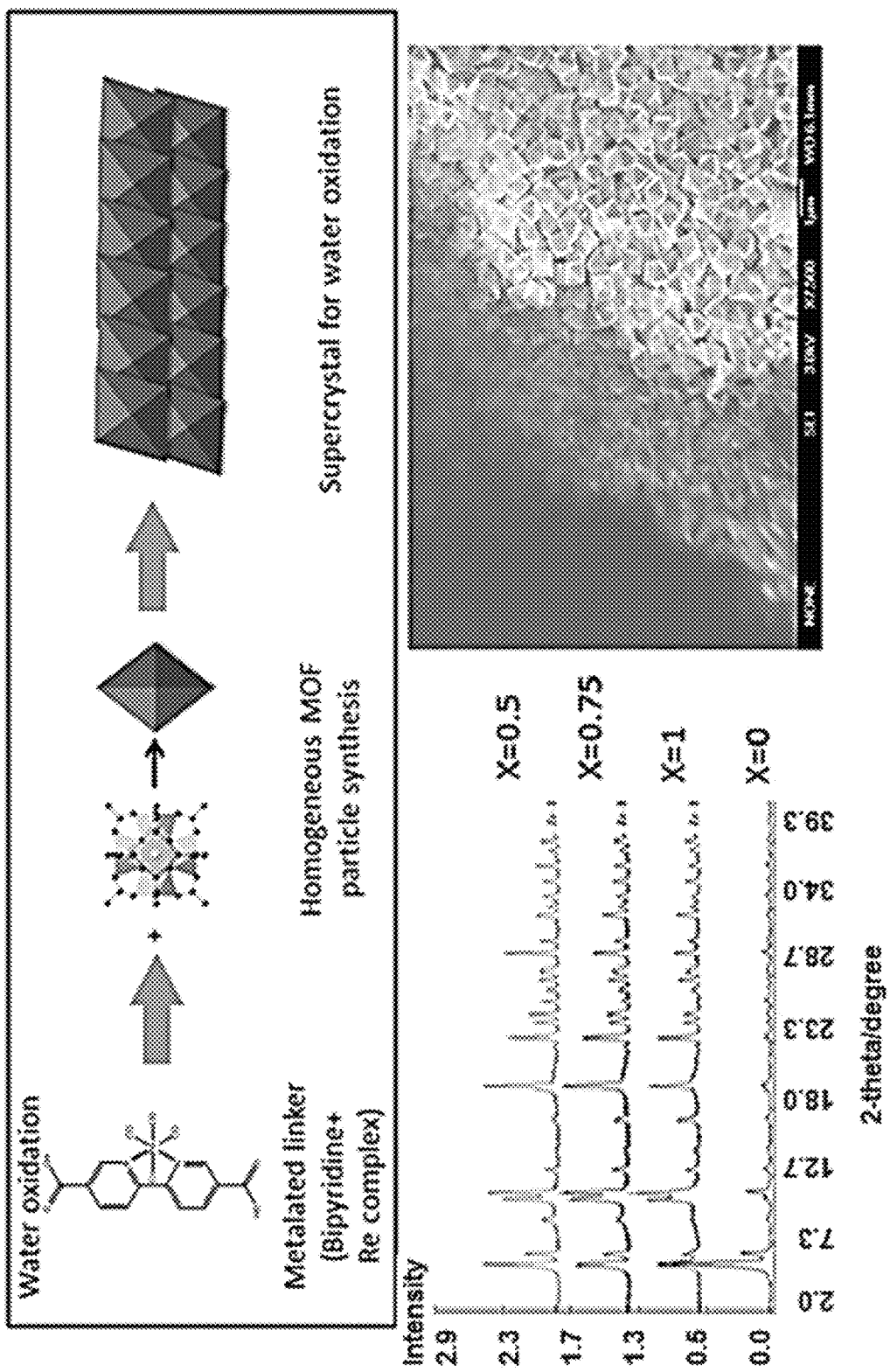
FIG. 19 provides for the formation of heterolite supercrystals of Zr-bipyridine based MOF that have been metalated with a Re complex. (Top) generalized scheme to produce a heterolite supercrystal for water oxidation. (Bottom left) Powder x-ray diffraction patterns of Zr-bipyridine based MOFs. (Bottom right) SEM image of a heterolite of Zr-bipyridine based MOFs.
Figure 20:
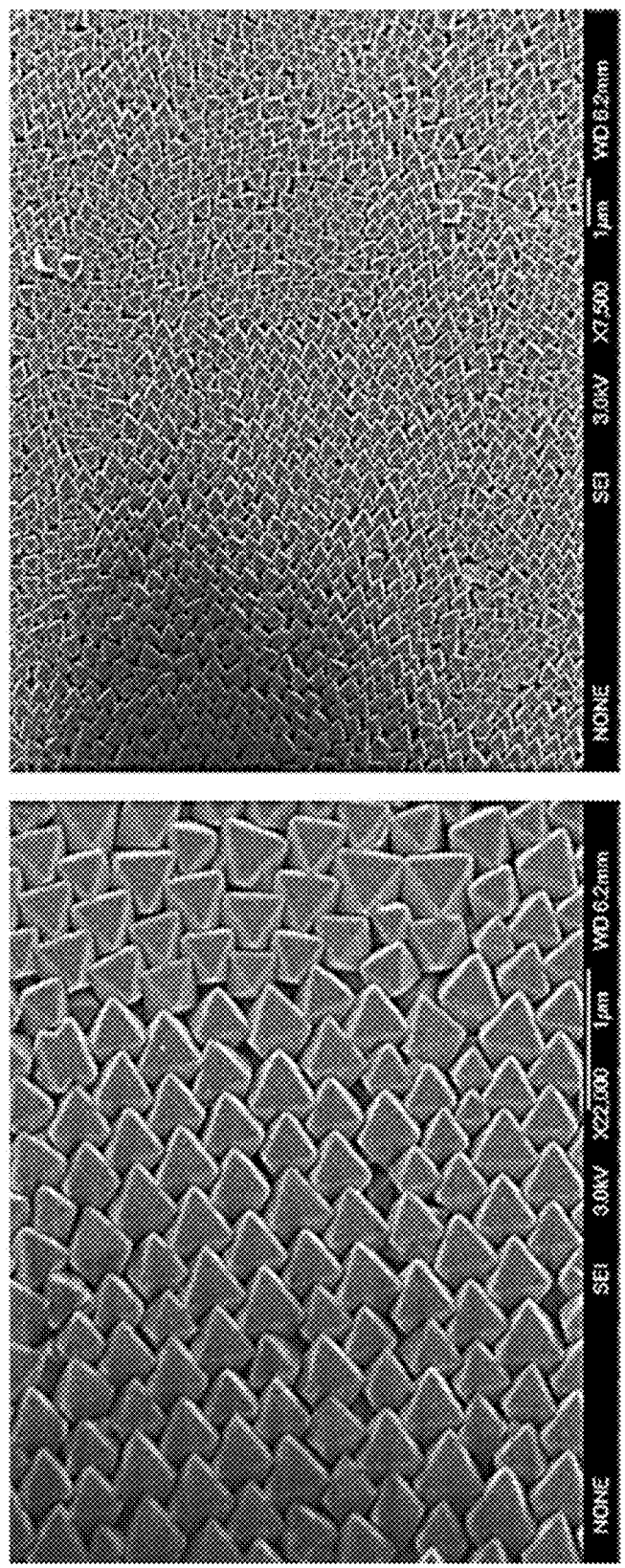
FIG. 20 presents a magnified SEM image of a heterolite of Zr-bipyridine based MOF that have been metalated with a Re complex.
Figure 21:
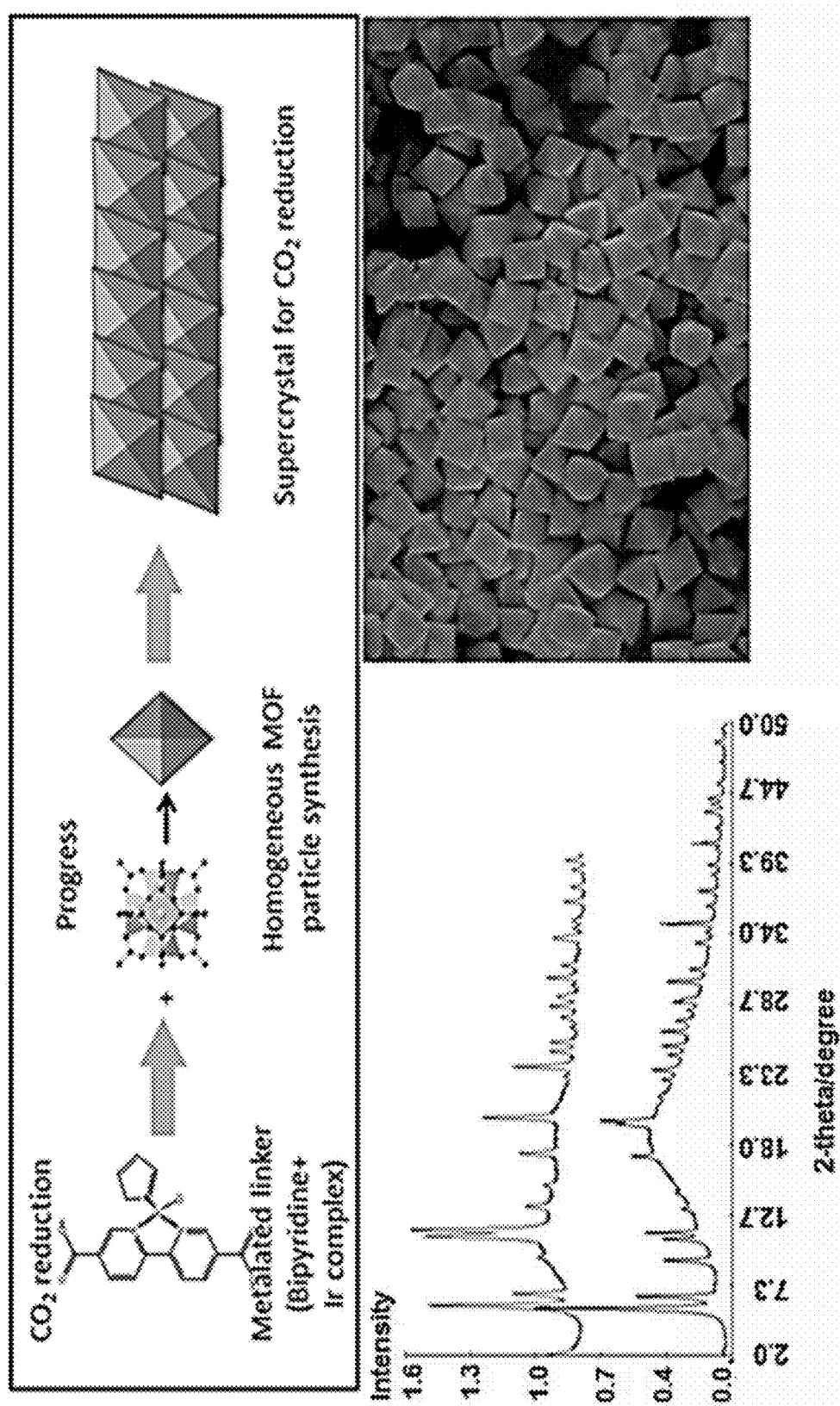
FIG. 21 provides for the formation of a heterolite of Zr-bipyridine based MOFs that have been metalated with an Ir complex. (Top) generalized scheme to produce a heterolite for $CO_2$ reduction. (Bottom left) Powder x-ray diffraction patterns of a Zr-bipyridine based MOFs. (Bottom right) SEM image of a heterolite of Zr-bipyridine based MOFs.
Figure 22:
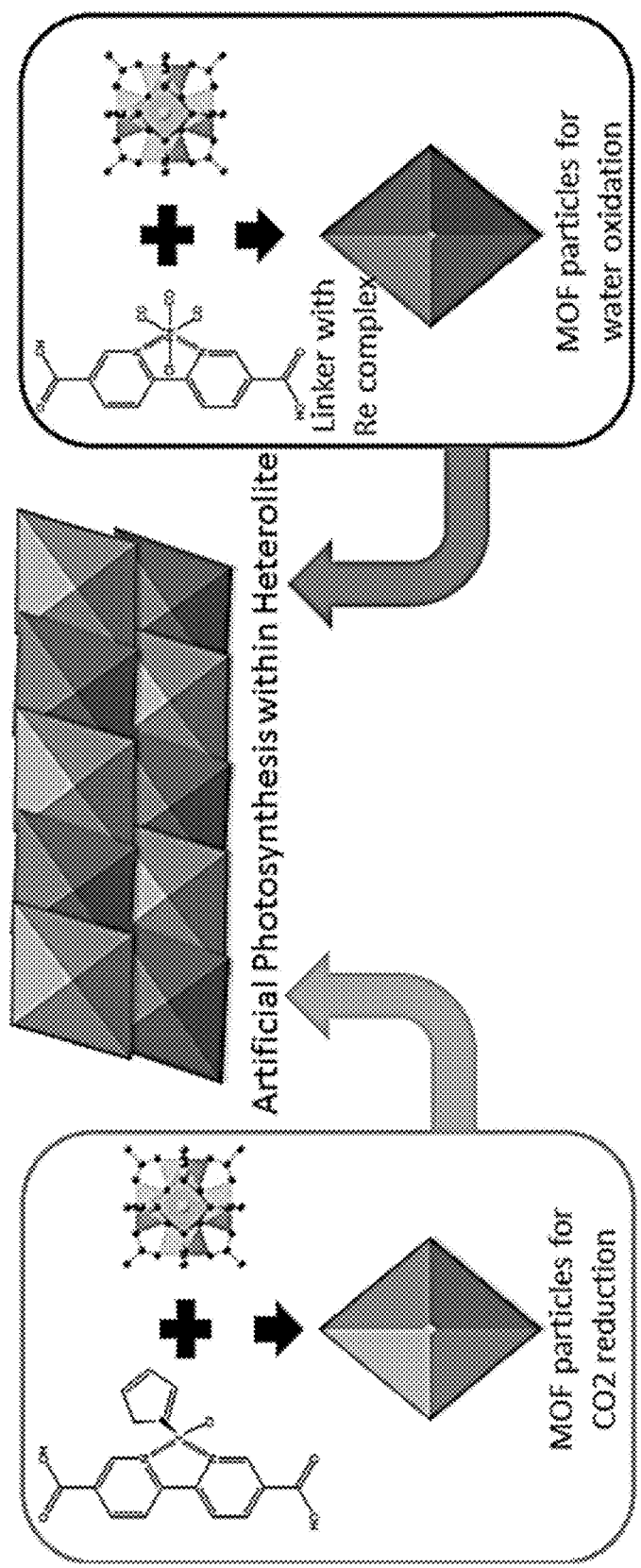
FIG. 22 shows the formation of MOF heterolites that can potentially perform artificial photosynthesis.

As used herein and in the appended claims, the singular forms "a," "and," and "the" include plural referents unless the context clearly dictates otherwise. Thus, for example, reference to "an organic linking ligand" includes a plurality of such linking ligands and reference to "the metal ion" includes reference to one or more metal ions and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned throughout the disclosure are incorporated herein by reference in full for the purpose of describing and disclosing the methodologies, which are described in the publications, which might be used in connection with the description herein. The publications discussed throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

Unless defined otherwise, all technical and scientific terms used herein have the same meaning as commonly understood to one of ordinary skill in the art. Although there are many methods and reagents similar or equivalent to those described herein, the exemplary methods and materials are presented herein.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates a bond that may be a single covalent bond or alternatively a double covalent bond. But in the case where an atom's maximum valence would be exceeded by forming a double covalent bond, then the bond would be a single covalent bond.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "cluster" refers to identifiable associations of 2 or more atoms. Such associations are typically established by some type of bond-ionic, covalent, Van der Waal, coordinate and the like.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "framework" as used herein, refers to a highly ordered structure comprised of secondary building units (SBUs) that can be linked together in defined, repeated and controllable manner, such that the resulting structure is characterized as being porous, periodic and crystalline. Typically, "frameworks" are two dimensional (2D) or three dimensional (3D) structures. Examples of "frameworks" include, but are not limited to, "metal-organic frameworks" or "MOFs", "zeolitic imidazolate frameworks" or "ZIFs", or "covalent organic frameworks" or "COFs". While MOFs and ZIFs comprise SBUs of metals or metal ions linked together by forming covalent bonds with linking clusters on organic linking moieties, COFs are comprised of SBUs of organic linking moieties that are linked together by forming covalent bonds via linking clusters. "Frameworks" are highly ordered and extended structures that are not based upon a centrally coordinated ion, but involve many repeated secondary building units (SBUs) linked together. Accordingly, "frameworks" are orders of magnitude much larger than coordination complexes and have different structural and chemical properties due to the framework's open and ordered structure.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

The term "heterocycle", as used in this disclosure, refers to ring structures that contain at least 1 noncarbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-aryl" used alone or as a suffix or prefix, refers to a heterocycle or heterocyclyl having aromatic character. Examples of heteroaryls include, but are not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

A "linking moiety" refers to a parent chain that binds a metal or metal ion or a plurality of metals or metal ions. A linking moiety may be further substituted post synthesis by reacting with one or more post-framework reactants.

The term "linking cluster" refers to one or more atoms capable of forming an association, e.g. covalent bond, polar covalent bond, ionic bond, and Van Der Waal interactions, with one or more atoms of another linking moiety, and/or one or more metal or metal ions. A linking cluster can be part of the parent chain itself and/or additionally can arise from functionalizing the parent chain, e.g. adding carboxylic acid groups to the parent chain. For example, a linking cluster can comprise $NN(H)N$, $N(H)NN$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, POSH, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Generally, the linking clusters disclosed herein are Lewis bases, and therefore have lone pair electrons available and/or can be deprotonated to form stronger Lewis bases. The deprotonated version of the linking clusters, therefore, are encompassed by the disclosure and anywhere a linking cluster that is depicted in a non-de-protonated form, the de-protonated form should be presumed to be included, unless stated otherwise.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals.

A "metal ion" refers to an ion of a metal. Metal ions are generally Lewis Acids and can form coordination complexes. Typically, the metal ions used for forming a coordination complex in a framework are ions of transition metals.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "post framework reactants" refers to all known substances that are directly involved in a chemical reaction. Post framework reactants typically are substances, either elemental or MOF frameworks, which have not reached the optimum number of electrons in their outer valence levels, and/or have not reached the most favorable energetic state due to ring strain, bond length, low bond dissociation energy, and the like. Some examples of post framework reactants include, but are not limited to:

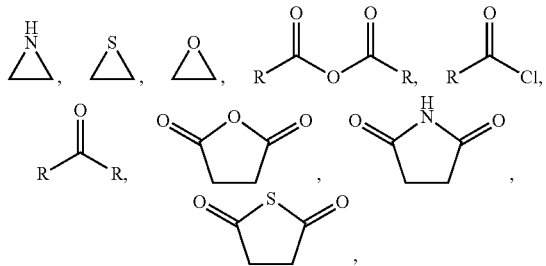

I—R, Br—R, CR₃—Mg—Br, CH₂R—Li, CR₃, Na—R, and K—R; and wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catecholborane), phosphorus-containing groups (e.g., phosphorous tribromide), and aluminum-containing groups (e.g., lithium aluminum hydride).

The term "substantially" as used to modify a term means that the modified term includes minor variations in size, purity, structure and the like by only a minor amount. Accordingly, "substantially homogenous in size" means that the material does not vary by more than 1%, 5%, 10%, 20% or 30% (or any value there between) in size from an average size. Thus, MOF nanocrystals do not vary in size by more than 30% from an average size.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

A "superlattice" is a periodic structure of layers of the same or two (or more) different materials. This also includes an ordered dispersion of individual MOF crystal in other MOF crystals of a different composition. Typically, the thickness of one layer is several nanometers. A MOF superlattice refers to layered MOF crystals, wherein a single layer of MOF crystals has a thickness of x and superlattice has a thickness of nx, wherein n is 2 or greater. The layered nanocrystal MOFs form mesoscopic materials (MOF heterolites), comprising ordered superlattices of a plurality of nano- or micro-porous metal-organic framework (MOF) nanocrystals. The MOF heterolites disclosed herein exhibit chemical and physical properties based on the interplay between the nanoscopic MOF building blocks at the mesoscopic level. Due to the long range crystalline ordering of the MOF heterolites, the mesoscopic materials are open materials that are ideal for catalysis, gas storage and gas separation. The MOF heterolites unit lengths can be tuned to any frequency of interest, leading to the use of MOF heterolites in light capturing applications, catalysis, and metamaterials. The superlattice materials can undergo targeted self-assembly as disclosed herein. Moreover, the self-assembly methods allow for size and shape directed sedimentation of MOF nanocrystals, including MOFs with large chemical differences, to form permanently porous supercrystals. The individual building blocks (MOF nanocrystals) can form interlocking well organized structure.

The term "unsubstituted" with respect to hydrocarbons, heterocycles, and the like, refers to structures wherein the parent chain contains no substituents.

Metal-organic frameworks (MOFs) are porous crystalline materials that are constructed by linking metal clusters called Secondary Binding Units (SBUs) and organic linking moieties. MOFs have high surface area and high porosity which enable them to be utilized in diverse fields, such as gas storage, catalysis, and sensors. Discovered about 15 years ago, more than 30,000 metal-organic frameworks, or MOFs, have been made so far. However, mesoscopic materials (MOF heterolites) constructed from superlattices of MOFs have not been previously characterized. Among the advantages of MOF heterolites is the ability to combine MOFs with different functionalities together in a structured superlattice array. The MOF heterolites place the MOFs in close proximity thereby providing possible synergistic effects for gas sorption or catalysis.

The disclosure provides for the synthesis and characterization of mesoscopic superlattice structures (heterolites) constructed from arranging metal-organic frameworks (MOFs) into a supercrystal array (MOF heterolites). It should be understood that while MOF heterolites are shown to be constructed from Zirconium-based MOFs in the figures and examples presented herein, that the assembly methods presented herein can equally be used with any MOF that is described in the literature to make a MOF heterolite of the disclosure. For a desired application (e.g., catalysis), the initial choice of MOF nanocrystals will provide the MOF heterolites with the requisite features.

The assembly methods provided herein are based on a two part strategy. First, the MOFs (sometimes referred to as MOF nanocrystals) are prepared to be the same-size with well-defined morphologies by dissolving synthetic modulators in MOF preparation solutions. These modulators provide a role in making homogenous nanocrystals by controlling the nucleation and growth of the nanocrystals so that they are formed at the same rate. After making homogenous MOF, MOF heterolites are constructed by using sedimentation process from colloidal solutions comprising the MOF nanocrystals. For the colloidal solutions, each MOF is coated with surfactant and dispersed in the solution. By using a sedimentation process, a well-ordered superlattice structure of the MOF heterolite can be generated. This supercrystal structure is porous and provides channels or cavities suitable to adsorb and/or separate gases. In addition, the MOFs may comprise functional groups that can be modified in order to improve the sorption properties of the materials.

In a particular embodiment, the disclosure provides for MOF heterolites which are comprised of homogenous MOF. In an alternate embodiment, the disclosure provides for MOF heterolites which are comprised of heterogeneous MOFs. In yet a further embodiment, the MOF heterolites are comprised of at least two, at least three, at least four, at least five, at least six, at least seven, or at least eight different MOFs. In a further embodiment, the MOFs may have similar or different catalytic, gas sorption, gas separation, luminescence, drug delivery, or sensor properties/activities.

In a further embodiment, the MOF heterolites disclosed herein are comprised of interconnected MOFs that have different catalytic specificities thereby controlling which and what kind of active compounds can be prepared. Further, the MOF heterolites disclosed herein organize the active compounds in three dimensions while maintaining porosity and providing unhindered access to active sites. In a particular embodiment, the disclosure provides for a MOF heterolite that is comprised of at least two different catalytic MOFs, wherein the first MOF catalyzes the oxidation of water, while the second type of MOF catalyzes the reduction of $CO_2$.

The MOF heterolites disclosed herein can be synthesized from multiple MOFS that utilize metal ions in distinct but different coordination geometries, in combination with ligands possessing multidentate functional groups in the presence or absence of suitable templating agents. In a particular embodiment, MOF heterolites disclosed herein comprise a supercrystal between 100 nm to 5000 nm, 150 nm to 2500 nm, 200 nm to 2000 nm, 250 nm to 1500 nm, or 500 nm to 1000 nm in size.

In a certain embodiment, the disclosure provides for the production of MOF heterolites from MOFs wherein the MOFs comprise a plurality of linked M-X-L secondary binding units (SBUs), wherein M is a metal, metal ion, or metal containing complex; X is an atom or cluster from an organic linking ligand that can form one or more bonds with M; and L is an organic linking ligand comprising an optionally substituted ($C_1$-$C_{20}$) alkyl, optionally substituted ($C_1$-$C_{20}$) alkenyl, optionally substituted ($C_1$-$C_{20}$) alkynyl, optionally substituted ($C_1$-$C_{20}$) hetero-alkyl, optionally substituted ($C_1$-$C_{20}$) hetero-alkenyl, optionally substituted ($C_1$-$C_{20}$) hetero-alkynyl, optionally substituted ($C_3$-$C_{12}$) cycloalkyl, optionally substituted ($C_3$-$C_{12}$) cycloalkenyl, optionally substituted aryl, optionally substituted heterocycle or optionally substituted mixed ring system, (in some embodiments, the linking ligand comprises at least two or more carboxylate linking clusters).

In a certain embodiment, one or more metals and/or metal ions that can be used in the synthesis of MOF nanocrystals making up a MOF heterolite disclosed herein, include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and combinations thereof, including any complexes which contain the metals or metal ions listed above, as well as any corresponding metal salt counter-anions.

The MOFs making up the MOF heterolites disclosed herein can be generated by first utilizing a plurality of linking moieties. In some embodiments, the linking moieties have different functional groups. In further embodiments, the linking moieties have different functional groups wherein at least one of these functional groups may be modified, substituted, or eliminated with a different functional group post-synthesis of the framework. In other words, at least one linking moiety comprises a functional group that may be post-synthesized reacted with a post framework reactant to further increase the diversity of the functional groups of the MOFs making up the MOF heterolites disclosed herein.

For example, and not by way of limitation, MOFs can be generated by condensing a metal or metal ion with a linking ligand. The linking ligand typically comprises a linking cluster (e.g., a COO— cluster) that undergoes condensation with a metal of metal ion (i.e., the X in M-X-L). Examples of linking ligands that can be used in such a reaction include:

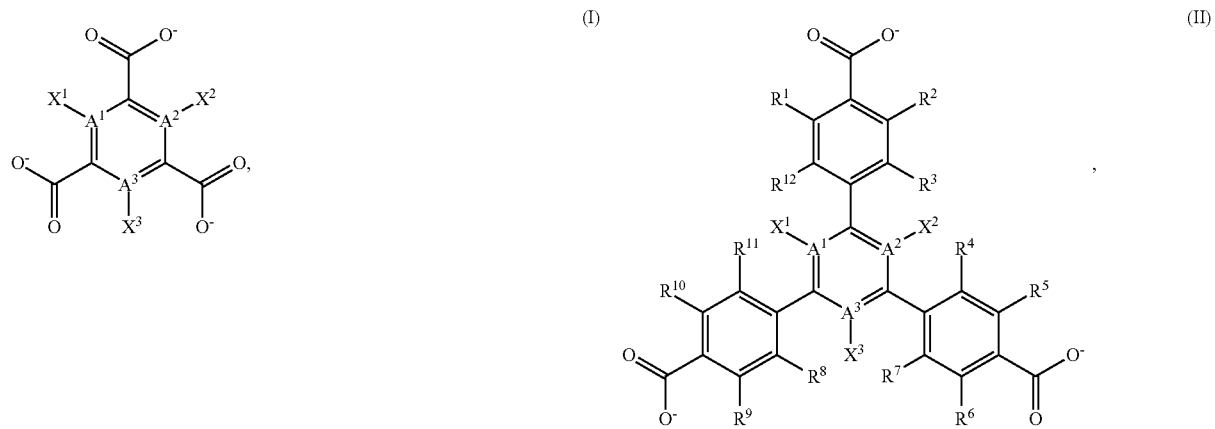

-continued
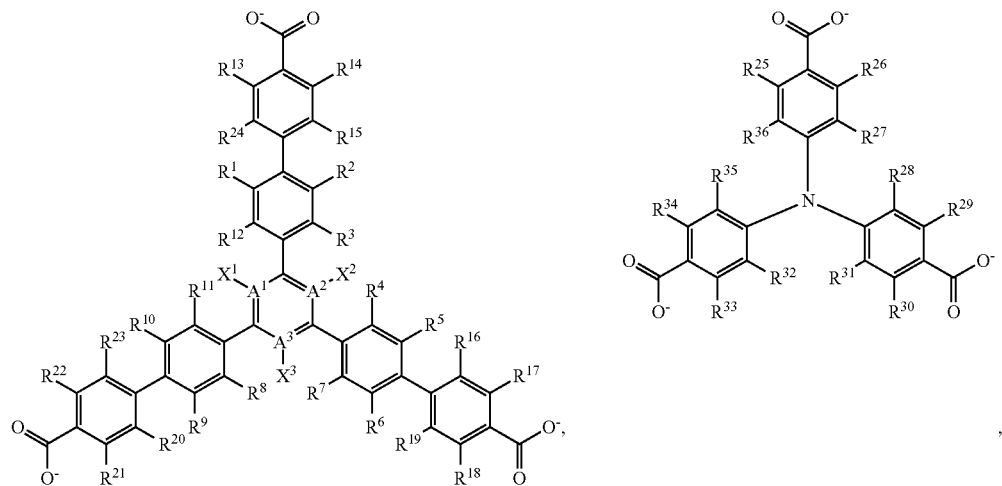
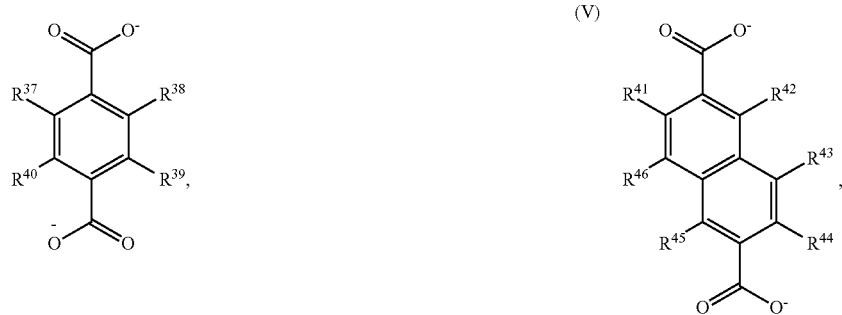

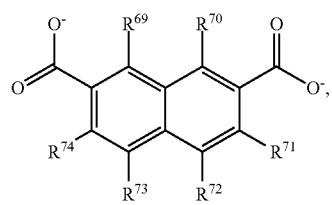
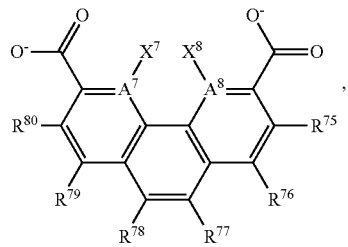
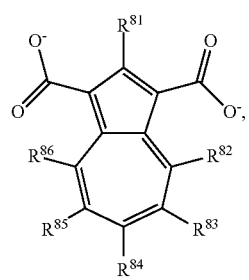
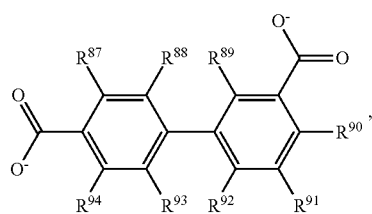
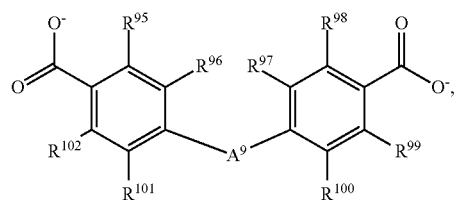
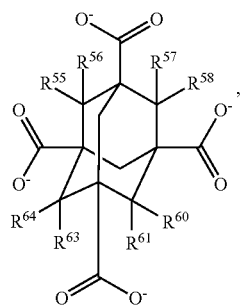
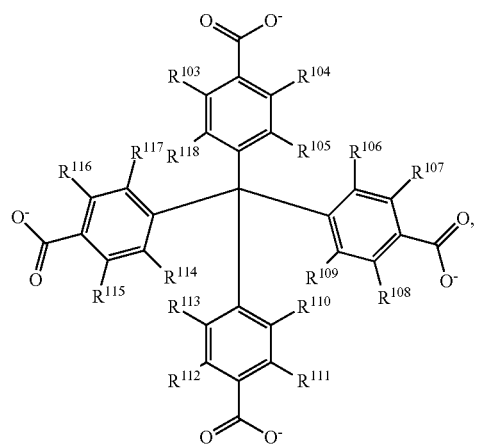
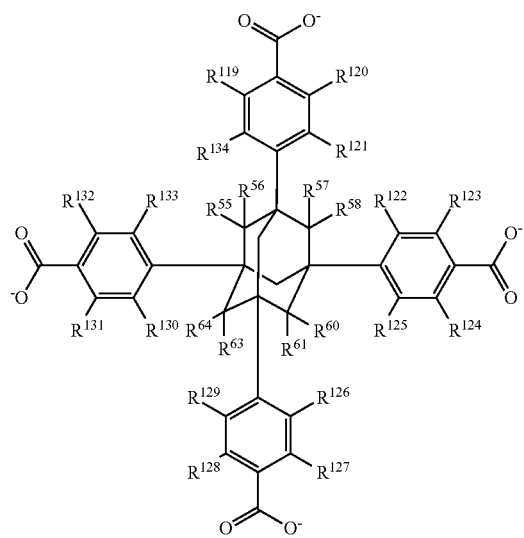

-continued
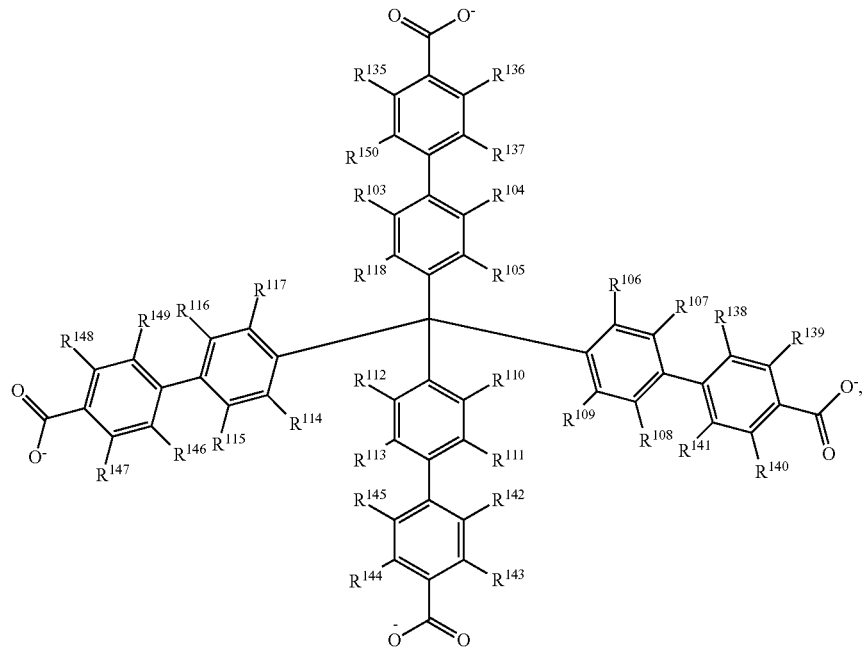
(XIX)
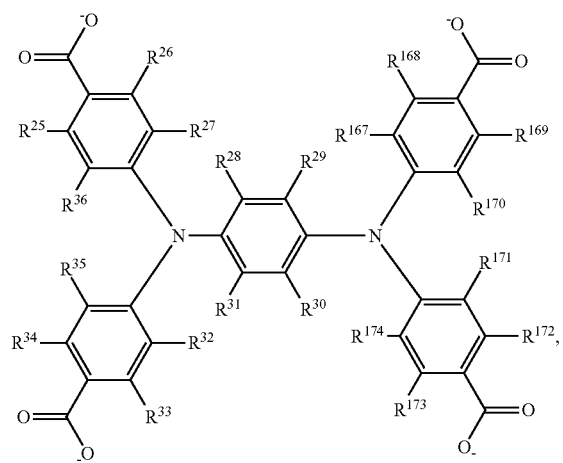
(XX)

(XXI)

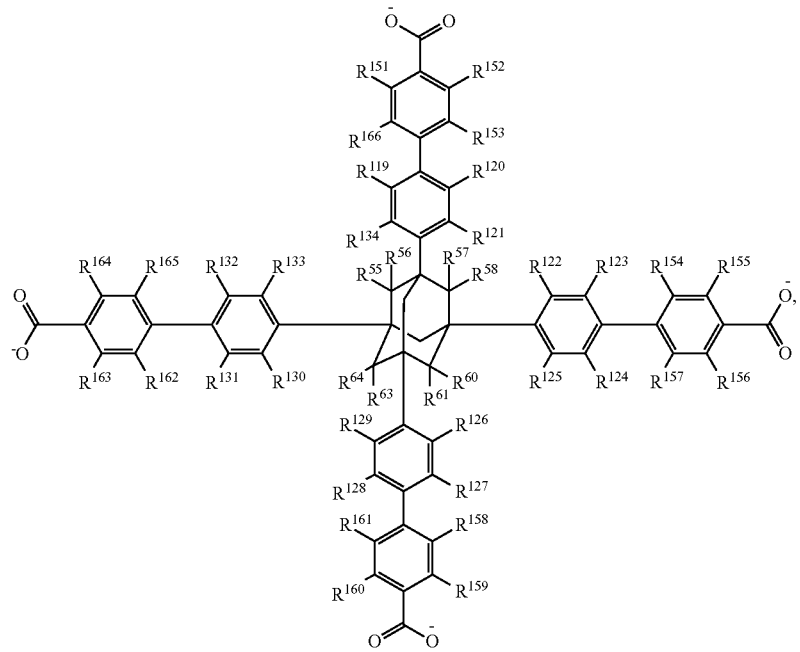

(XXII)

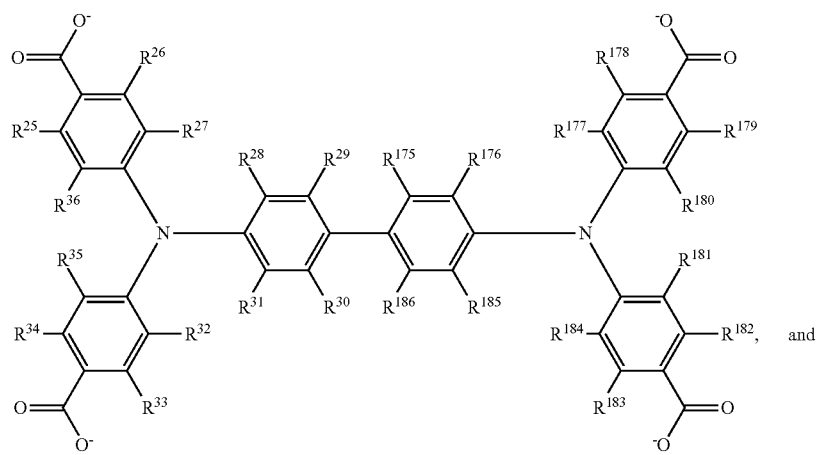
and

Formula XXIII

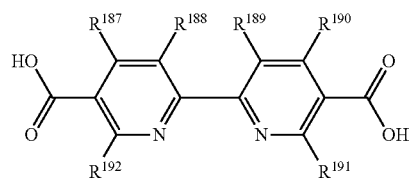

wherein, $A^1$-$A^8$ are independently a C, N, O, or S; $A^9$ is selected from

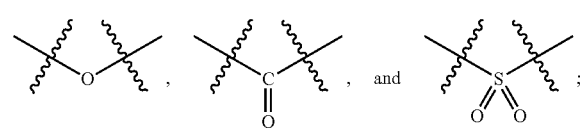

$X^1$-$X^8$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$) alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$) cycloalkenyl, optionally substituted aryl, optionally substituted heterocycle, optionally substituted mixed ring system, wherein one or more adjacent R groups can be linked together to form one or more optionally substituted rings selected from the group comprising cycloalkyl, cycloalkenyl, heterocycle, aryl, and mixed ring system; and $R^1$-$R^{192}$ are independently selected from H, D, optionally substituted FG, optionally substituted ($C_1$-$C_{20}$)alkyl, optionally substituted ($C_1$-$C_{19}$)heteroalkyl, optionally substituted (C₁-C₂₀)alkenyl, optionally substituted (C₁-C₁₉)heteroalkenyl, optionally substituted (C₁-C₁₉)alkynyl, optionally substituted (C₁-C₁₉)heteroalkynyl, optionally substituted (C₁-C₁₉)cycloalkyl, optionally substituted (C₁-C₁₉)cycloalkenyl, optionally substituted aryl, optionally substituted heterocycle, optionally substituted mixed ring system, wherein one or more adjacent R groups can be linked together to form one or more optionally substituted rings selected from the group comprising cycloalkyl, cycloalkenyl, heterocycle, aryl, and mixed ring system. For example, R¹-R¹⁹² can be independently selected from:

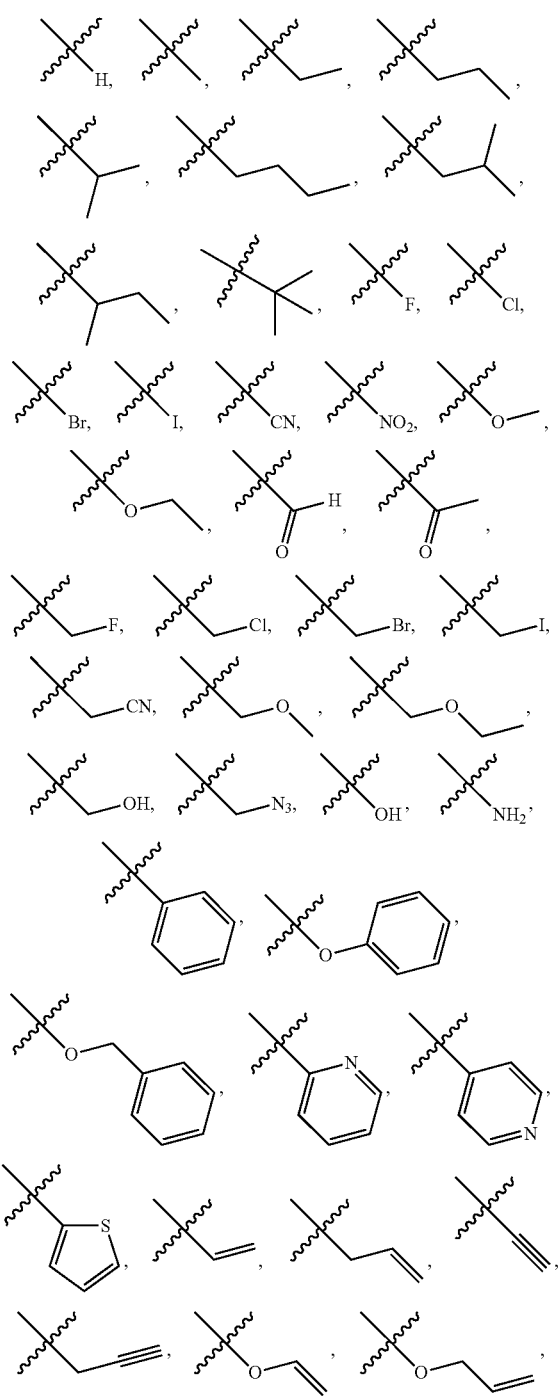

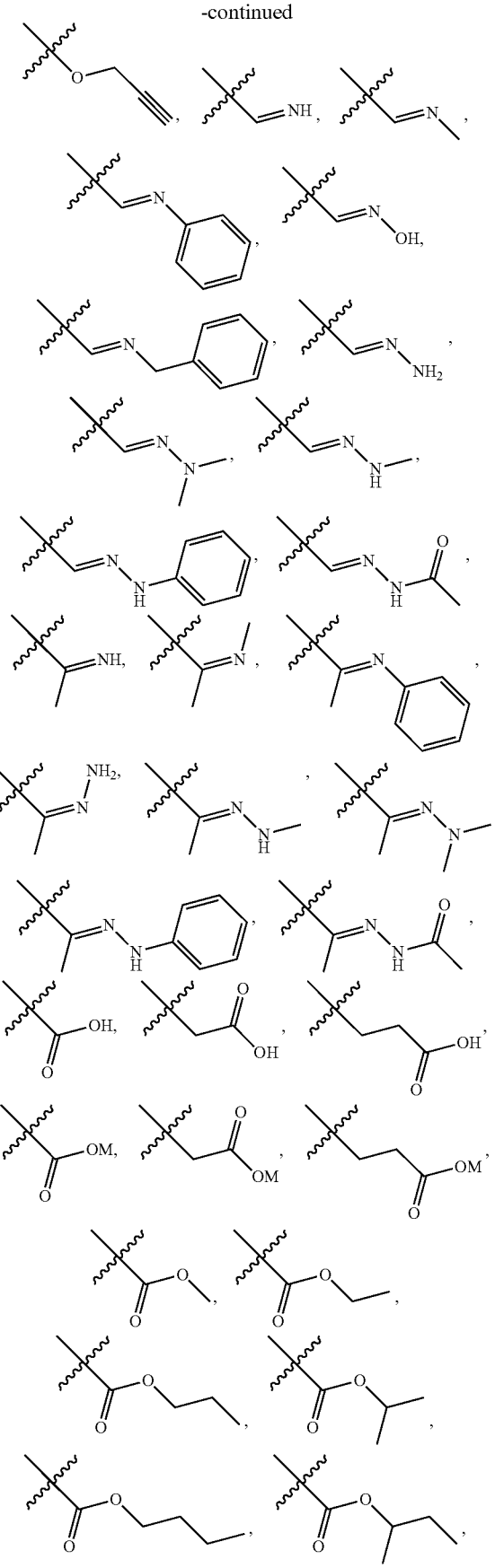

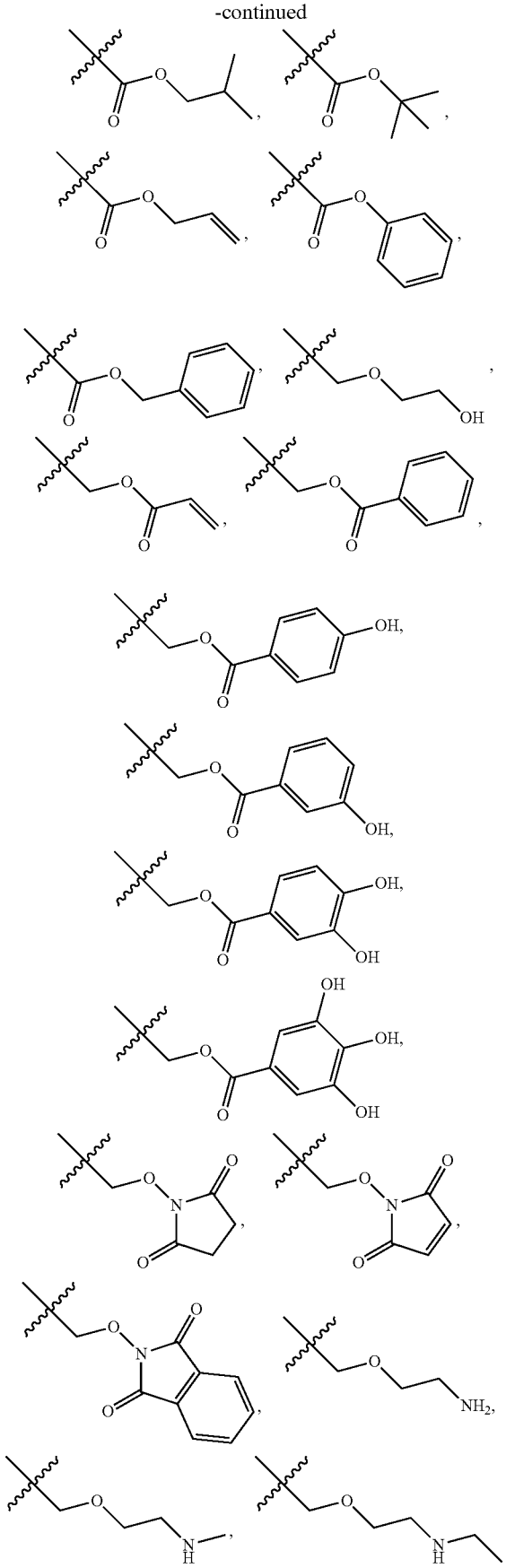
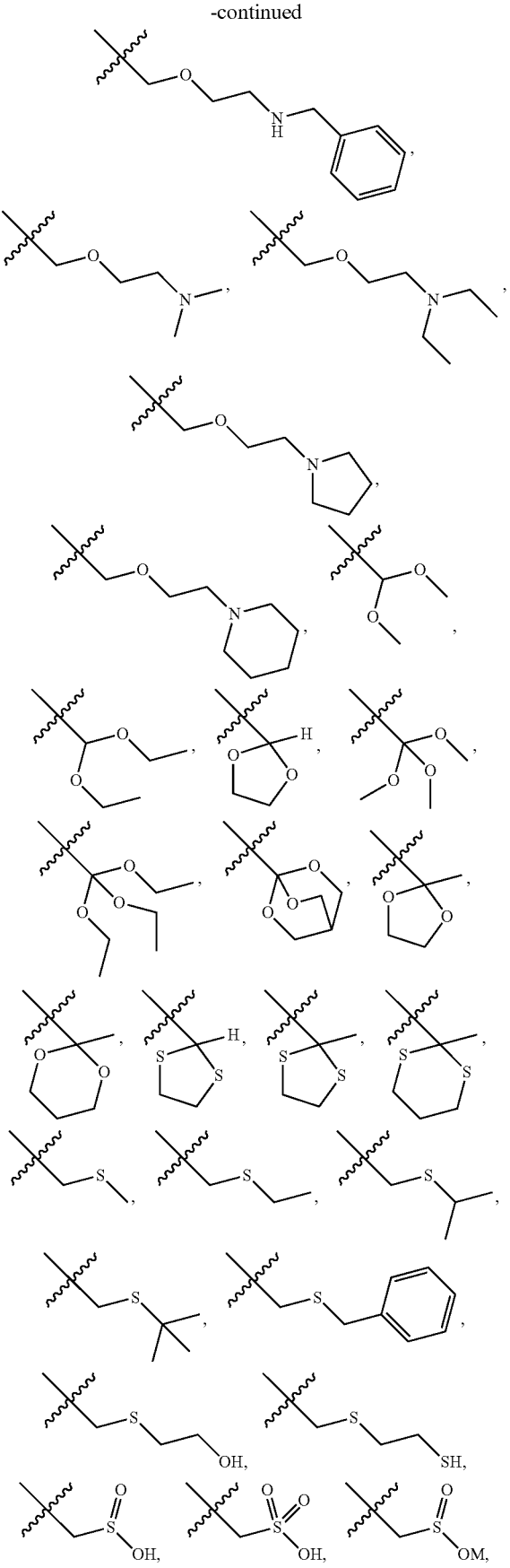

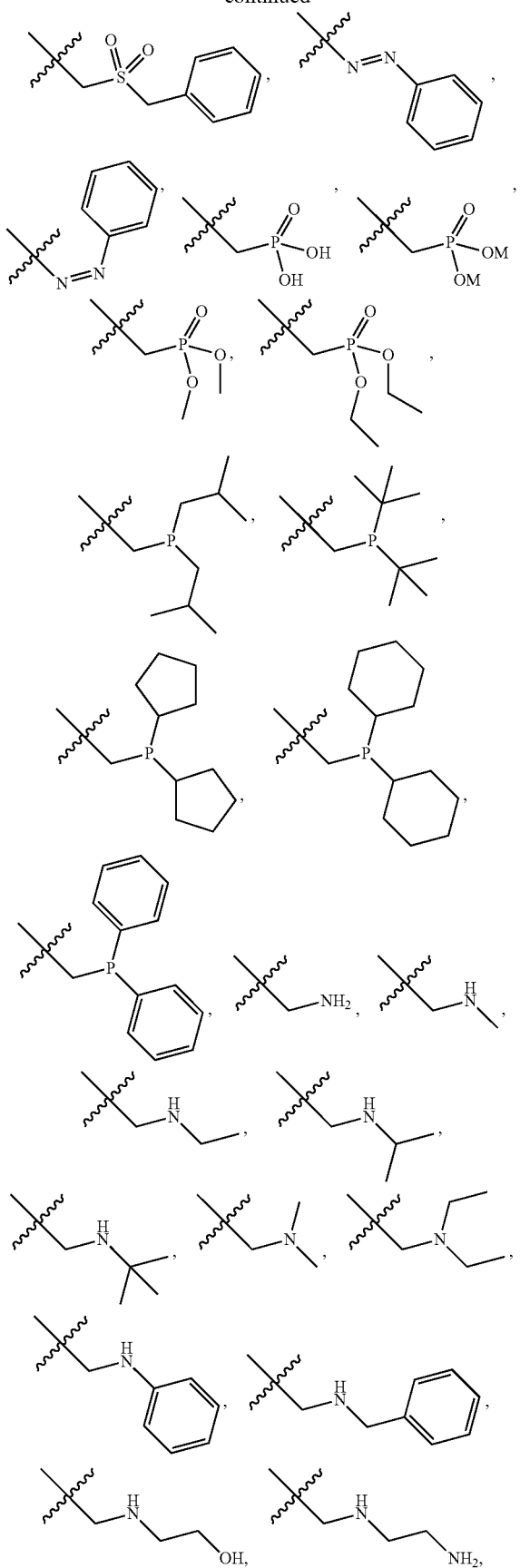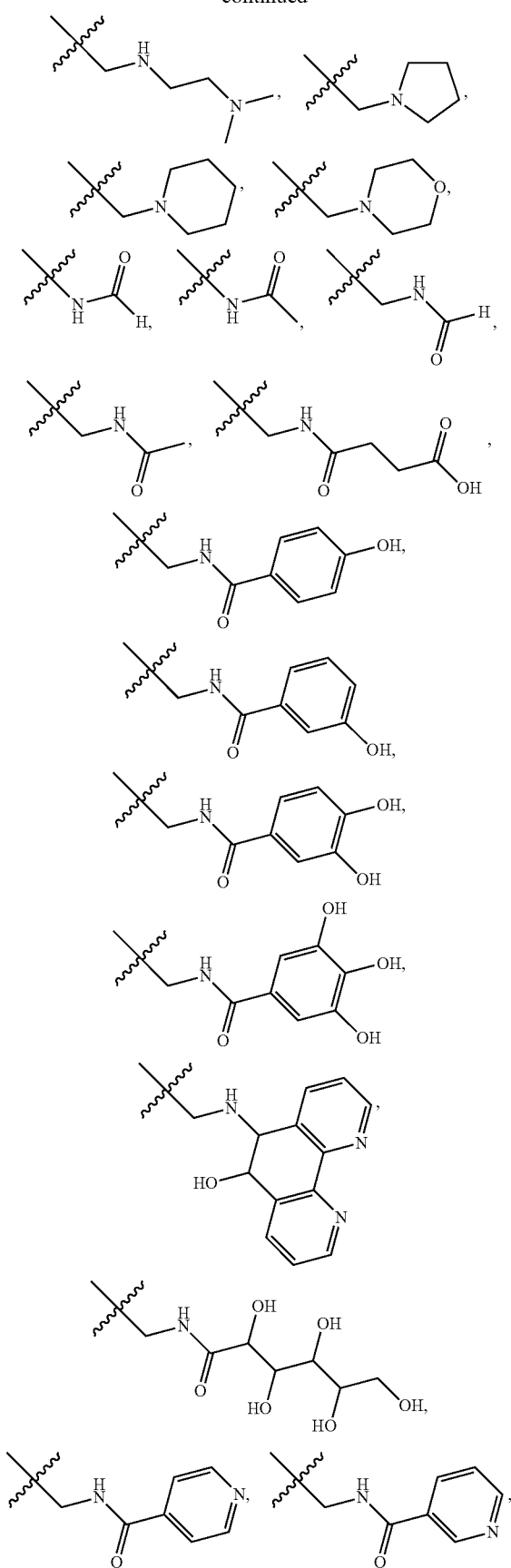

-continued

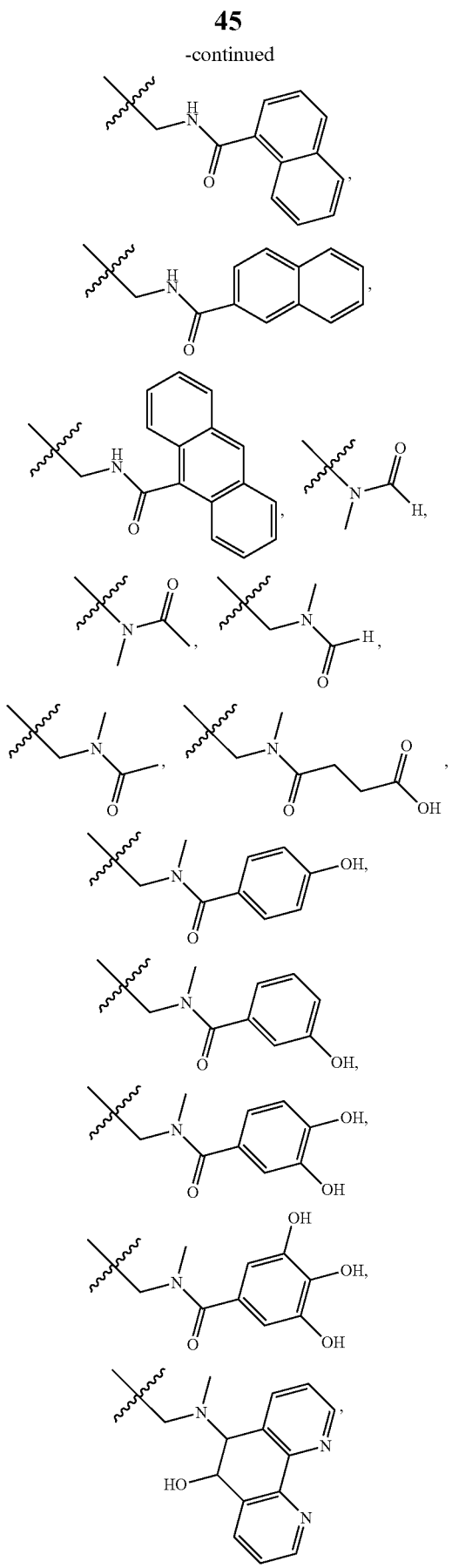

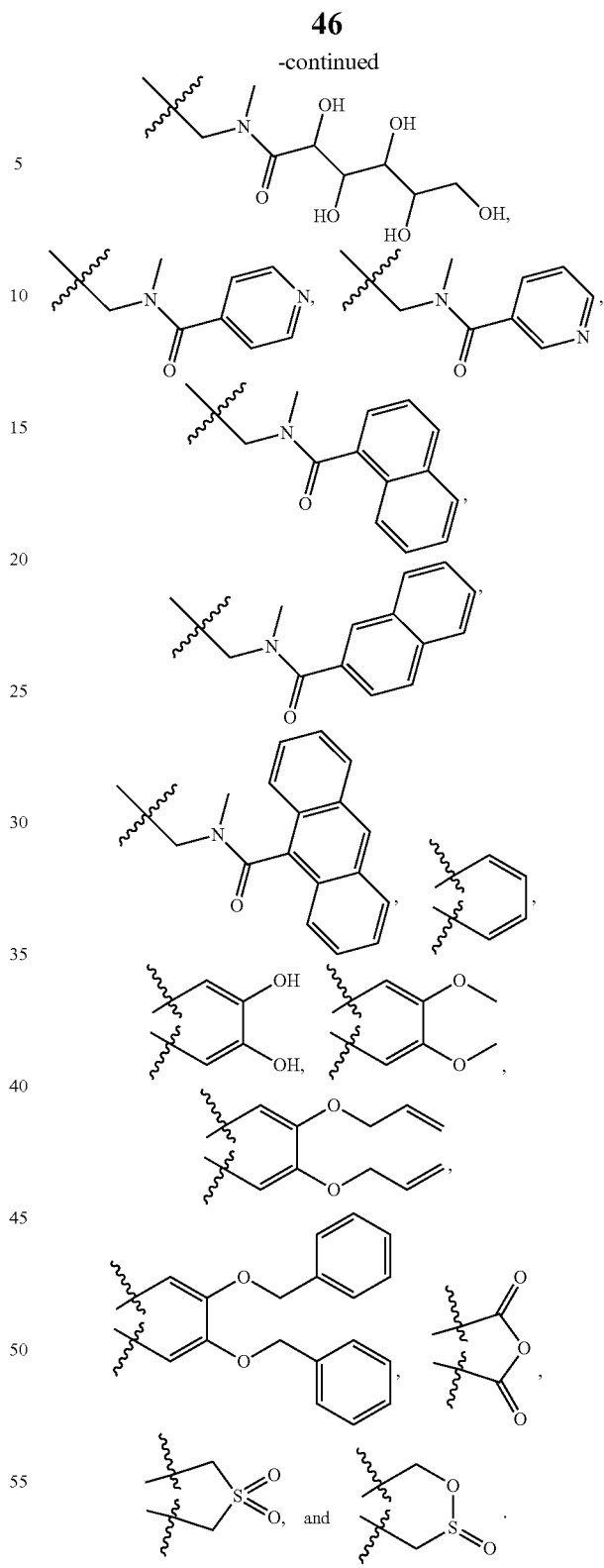

Figure 23:
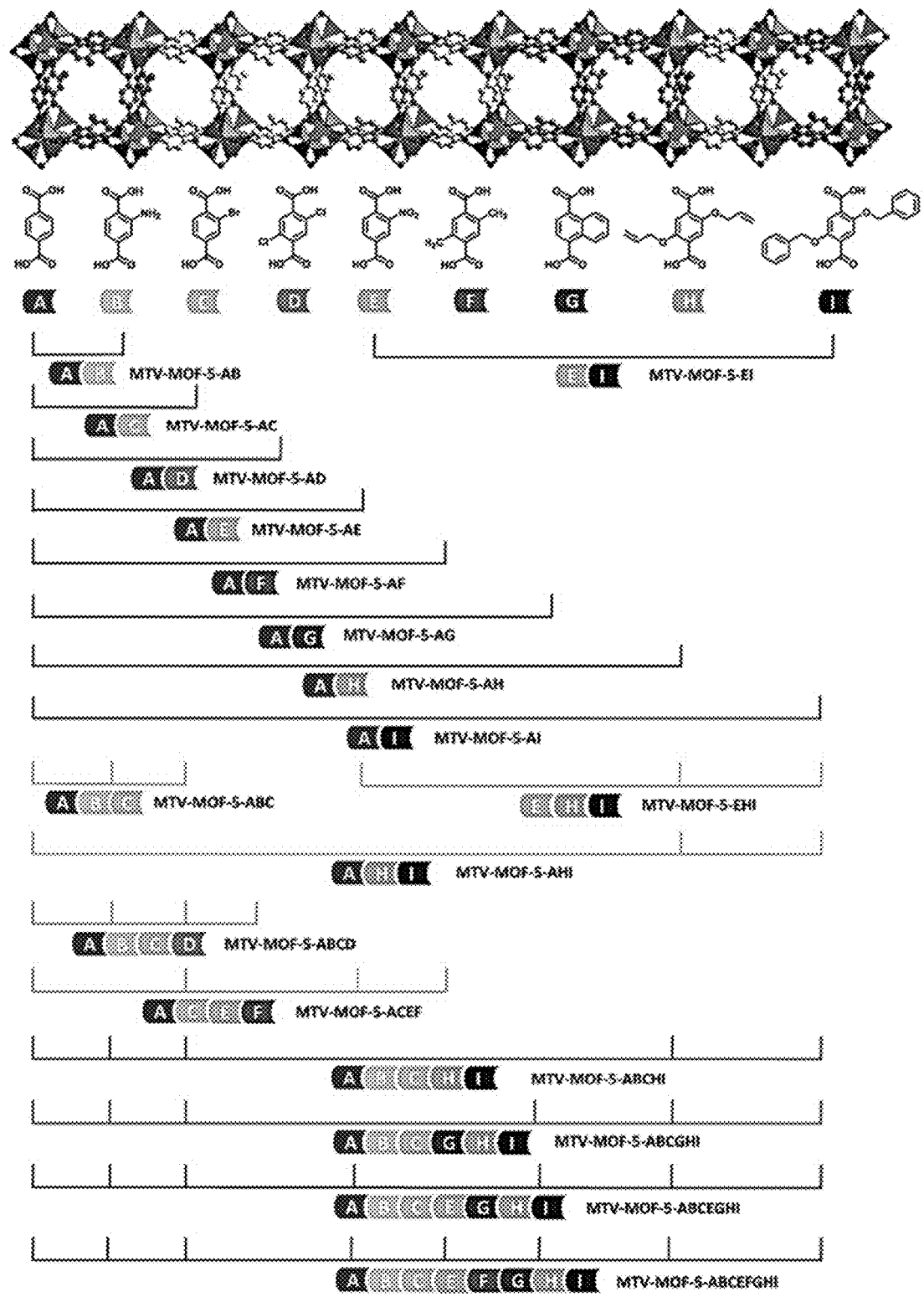
FIG. 23 demonstrates multi-varied links used to generate mvMOFs as well as examples of mvMOFs. The mvMOFs can then be used for from heterolites.

In addition, multivariant MOFs (aka mvMOFs or MTVs) can be used to make a MOF heterolite of the disclosure. Such MTVs comprise a linking moiety having a backbone of as selected above, but by which the side-groups linked to the backbone can be selectively modified. In MTVs a plurality of linking moieties with different functional groups whose orientation, number, relative position and ratio along the backbone are controllable by virtue of the unchanged size of the linking moiety and the unaltered connectivity of the backbone and wherein the functional groups modify the chemical and physical properties of a pore in the framework (see, FIG. 23 and International Application Publ. No. WO2010/148296, the disclosure of which is incorporated herein by reference).

After MOFs are synthesized, the MOFs may be further modified by reacting with one or more post framework reactants that may or may not have denticity prior to assembling into the MOF heterolites of the disclosure. In a certain embodiment, the MOFs as-synthesized are not reacted with a post framework reactant. In another embodiment, the MOFs as-synthesized are reacted with at least one post framework reactant. In yet another embodiment, the MOFs as-synthesized are reacted with at least two post framework reactants. In a further embodiment, the MOFs as-synthesized are reacted with at least one post framework reactant that will result in adding denticity to the MOFs.

The disclosure provides for chemical reactions that modify, substitute, or eliminate a functional group post-synthesis of a MOF disclosed herein with a post framework. These chemical reactions may use one or more similar or divergent chemical reaction mechanisms depending on the type of functional group and/or post framework reactant used in the reaction. Examples of chemical reaction include, but are not limited to, radical-based, unimolecular nucleophilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloadition, ring closing metathesis (RCM), pericylic, electrocylic, rearrangement, carbene, carbenoid, cross coupling, and degradation. By modifying the MOFs post-synthetically, access to functional groups that were previously inaccessible or accessible only through great difficulty and/or cost is possible and facile.

In another embodiment, a post framework reactant adds at least one effect to the MOFs making up a MOF heterolite disclosed herein, including, but not limited to, modulating the gas storage ability of the MOFs making up a MOF heterolite disclosed herein; modulating the sorption properties of the MOFs making up a MOF heterolite disclosed herein; modulating the pore size of the MOFs making up a MOF heterolite disclosed herein; modulating the catalytic activity of the MOFs making up a MOF heterolite disclosed herein; modulating the conductivity of the MOFs making up a MOF heterolite disclosed herein; and modulating the sensitivity of the MOFs making up a MOF heterolite disclosed herein to the presence of an analyte of interest. In a further embodiment, a post framework reactant adds at least two effects to the MOFs making up a MOF heterolite disclosed herein, including, but not limited to, modulating the gas storage ability of the MOFs making up a MOF heterolite disclosed herein; modulating the sorption properties of the MOFs making up a MOF heterolite disclosed herein; modulating the pore size of the MOFs making up a MOF heterolite disclosed herein; modulating the catalytic activity of the MOFs making up a MOF heterolite disclosed herein; modulating the conductivity of the MOFs making up a MOF heterolite disclosed herein; and modulating the sensitivity of the MOFs making up a MOF heterolite disclosed herein to the presence of an analyte of interest.

In a particular embodiment, a post framework reactant is selected to modulate the size of the pores of the MOFs making up a MOF heterolite disclosed herein.

In another embodiment, a post framework reactant is selected to increase the hydrophobicity of the MOFs making up a MOF heterolite disclosed herein.

In yet another embodiment, a post framework reactant is selected to modulate gas separation of the MOFs making up a MOF heterolite disclosed herein. In a certain embodiment, a post framework reactant creates an electric dipole moment on the surface of the MOFs making up a MOF heterolite disclosed herein when it chelates a metal ion.

In a further embodiment, a post framework reactant is selected to modulate the gas sorption properties of the MOFs making up a MOF heterolite disclosed herein. In another embodiment, a post framework reactant is selected to promote or increase greenhouse gas sorption of the MOFs making up a MOF heterolite disclosed herein. In another embodiment, a post framework reactant is selected to promote or increase hydrocarbon gas sorption of the MOFs making up a MOF heterolite disclosed herein.

In yet a further embodiment, a post framework reactant is selected to increase or add catalytic efficiency to the MOFs making up a MOF heterolite disclosed herein. In a particular embodiment, a post framework reactant is selected so that organometallic complexes (e.g., Re complexes) can be tethered to the MOFs making up a MOF heterolite disclosed herein. Such tethered organometallic complexes can be used, for example, as heterogeneous catalysts.

In a particular embodiment, the MOF heterolites of the disclosure can be used for catalysis, adsorption and separation, energy gas storage (e.g., hydrogen, methane and other natural gases), greenhouse gas capture, respirator against toxic gas/vapor, adsorptive thermal battery, water supply and purification, proton conductor, photovoltaic devices, artificial photosynthesis, and radioactive ion capture.

In one embodiment of the disclosure, a gas storage or separation material comprising a MOF heterolite of the disclosure is provided. Advantageously, the MOF heterolite includes one or more sites for storing and/or separating gas molecules. Gases that may be stored in the gas storage material of the disclosure include gas molecules which have high electron density for attachment to the one or more sites on the surface area of a pore or interpenetrating porous network. Such electron density includes molecules having multiple bonds between two atoms contained therein or molecules having a lone pair of electrons. Suitable examples of such gases include, but are not limited to, the gases comprising a component selected from the group consisting of ammonia, argon, carbon dioxide, carbon monoxide, hydrogen, and combinations thereof. In a particularly useful variation the gas storage material is a hydrogen storage material that is used to store hydrogen ($H_2$). In another particularly useful variation, the gas storage material is a carbon dioxide storage material that may be used to separate carbon dioxide from a gaseous mixture.

The disclosure provides an apparatus and method for separating one or more components from a multi-component gas using a separation system having a feed side and an effluent side separated by a MOF heterolite of the disclosure. The apparatus may comprise a column separation format.

In an embodiment of the disclosure, a gas storage material comprising a MOF heterolite is provided. Gases that may be stored or separated by the methods, compositions and systems of the disclosure includes gas molecules comprising available electron density for attachment to the one or more sites. Such electron density includes molecules having multiple bonds between two atoms contained therein or molecules having a lone pair of electrons. Suitable examples of such gases include, but are not limited to, the gases comprising ammonia, argon, carbon dioxide, carbon monoxide, hydrogen, and combinations thereof. In particularly useful variation, the gas binding material is a carbon dioxide binding material that may be used to separate carbon dioxide from a gaseous mixture.

In an embodiment, a gas separation material comprising one or more MOF heterolite disclosed herein is provided. Advantageously, a MOF heterolite disclosed herein includes one or more open metal sites for sorption of one or more select gas molecules resulting in separation of these gas molecules from a multicomponent gas. Furthermore, gases that may be separated by one or more MOF heterolites disclosed herein include gas molecules that have available electron density for attachment to the one or more open metal sites on the surface area of a pore or interpenetrating porous network. Such electron density includes molecules having multiple bonds between two atoms contained therein or molecules having a lone pair of electrons. Suitable examples of such gases include, but are not limited to, the gases comprising ammonia, argon, carbon dioxide, hydrogen sulfide, carbonyl sulfide, carbon disulfide, mercaptans, carbon monoxide, hydrogen, and combinations thereof. In a particular embodiment, one or more MOFs disclosed herein, can be used to separate one or more component gases from a multi-component gas mixture. In a certain embodiment, one or more MOF heterolites disclosed herein can be used to separate one or more gases with high electron density from a gas mixture. In another embodiment, one or more MOF heterolites disclosed herein can be used to separate one or more gases with high electron density from one or more gases with low electron density. In yet another embodiment, the disclosure provides for MOF heterolites that are comprised of at least two, at least three, at least four, at least five, at least six, at least seven, or at least eight different MOFs that have different gas sorption properties and/or different gas adsorption specificities.

In a particular embodiment, one or more MOF heterolites disclosed herein are part of a device. In another embodiment, a gas separation device comprises one or more MOF heterolites of the disclosure. In a further embodiment, a gas separation device used to separate one or more component gases from a multi-component gas mixture comprises one or more MOF heterolites disclosed herein. Examples of gas separation and/or gas storage devices include, but are not limited to, purifiers, filters, scrubbers, pressure swing adsorption devices, molecular sieves, hollow fiber membranes, ceramic membranes, cryogenic air separation devices, and hybrid gas separation devices. In a certain embodiment, a gas separation device used to separate one or more gases with high electron density from gas mixture comprises one or more MOFs of the disclosure. In a further embodiment, a gas separation device used to separate one or more gases with high electron density from one or more low density gases comprises one or more MOF heterolites of the disclosure.

In a particular embodiment of the disclosure, a gas storage material comprises one more MOF heterolites disclosed herein. A gas that may be stored or separated by the methods, compositions and systems of the disclosure includes gas molecules comprising available electron density for attachment to the one or more open metal sites. Such electron density includes molecules having multiple bonds between two atoms contained therein or molecules having a lone pair of electrons. Suitable examples of such gases include, but are not limited to, the gases comprising ammonia, argon, hydrogen sulfide, carbon dioxide, hydrogen sulfide, carbonyl sulfide, carbon disulfide, mercaptans, carbon monoxide, hydrogen, and combinations thereof. In particularly useful variation, a gas binding material is a carbon dioxide binding material that may be used to separate carbon dioxide from a gaseous mixture. In a particularly useful variation a gas storage material is a hydrogen storage material that is used to store hydrogen ($H_2$). In another particularly useful variation, a gas storage material is a carbon dioxide storage material that may be used to separate carbon dioxide from a gaseous mixture.

In yet a further embodiment, one or more MOF heterolites disclosed herein can be used to separate and/or store one or more gases selected from the group comprising carbon monoxide, carbon dioxide, hydrogen sulfide, carbonyl sulfide, carbon disulfide, mercaptans, nitrous oxide, and ozone.

In another embodiment, one or more MOF heterolites disclosed herein can be used to separate and/or store one or more gases selected from the group comprising carbon monoxide, carbon dioxide, hydrogen sulfide, carbonyl sulfide, carbon disulfide, and mercaptans.

In yet another embodiment, one or more MOF heterolites disclosed herein can be used to separate and/or store carbon monoxide or carbon dioxide.

In an embodiment, one or more MOF heterolites disclosed herein can be used to separate and/or store hydrogen.

In another embodiment, a gas storage device comprises one or more MOF heterolites disclosed herein. In a further embodiment, a gas storage device used to adsorb and/or absorb one or more component gases from a multi-component gas mixture comprises one or more MOF heterolites disclosed herein. In a certain embodiment, a gas storage device used to adsorb and/or absorb one or more gases with high electron density from gas mixture comprises one or more MOF heterolites disclosed herein. In a further embodiment, a gas storage device used to adsorb and/or absorb one or more gases with high electron density from one or more low density gases comprises one or more MOF heterolites disclosed herein.

In a particular embodiment, the disclosure provides for an artificial photosynthesis device which comprises one or more MOF heterolites of the disclosure. In particular, one or more MOF heterolites disclosed herein can oxidize water and/or can reduce $CO_2$.

The disclosure also provides methods using MOF heterolites disclosed herein. In a certain embodiment, a method to separate or store one or more gases comprises contacting one or more gases with one or more MOF heterolites disclosed herein. In a further embodiment, a method to separate or store one or more gases from a mixed gas mixture comprises contacting the gas mixture with one or more MOF heterolites disclosed herein. In yet a further embodiment, a method to separate or store one or more high electron density gases from a mixed gas mixture comprises contacting the gas mixture with one or more MOF heterolites disclosed herein. In a certain embodiment, a method to separate or store one or more gases from a fuel gas stream comprises contacting the fuel gas stream with one or more MOF heterolites disclosed herein. In a further embodiment, a method to separate or store one or more acid gases from a natural gas stream comprises contacting the natural gas stream with one or more MOF heterolites disclosed herein. In yet another embodiment, a method to separate or store one or more gases from the exhaust of a combustion engine comprises contacting the exhaust with one or more MOF heterolites disclosed herein. In a certain embodiment, a method to separate or store one or more gases from flue-gas comprises contacting the flue-gas with one or more MOF heterolites disclosed herein.

The MOF heterolites of the disclosure can be used for removing contaminants from natural gas streams, including carbon dioxide, hydrogen sulfide, and water vapor. "Natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. The natural gas will also typically contain ethane, higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil.

In a certain embodiment, one or more MOF heterolites disclosed herein can be used to separate and/or store one or more gases from a natural gas stream. In another embodiment, one or more MOF heterolites disclosed herein can be used to separate and/or store one or more acid gases from a natural gas stream. In yet another embodiment, one or more MOF heterolites disclosed herein can be used to separate and/or store one or more gases from a town gas stream. In yet another embodiment, one or more MOF heterolites disclosed herein can be used to separate and/or store one or more gases of a biogas stream. In a certain embodiment, one or more MOF heterolites disclosed herein can be used to separate and/or store one or more gases from a syngas stream.

Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

MOF heterolites of the disclosure can be used as standard compounds for sorption instruments, and obtained results would be helpful to improve various industrial plants (i.e. separation or recovery of chemical substance).

The MOFs used in making the MOF heterolites of the disclosure include a plurality of pores for gas adsorption. In one variation, the plurality of pores has a unimodal size distribution. In another variation, the plurality of pores have a multimodal (e.g., bimodal) size distribution.

The disclosure further provides for catalysts comprising a MOF heterolite of the disclosure. The MOF heterolites disclosed herein can be used in the catalytic conversion of organic molecules or inorganic molecules (e.g., $CO_2$, water, etc.) to different molecules. Reactions of this type are, for example, oxidations, such as the oxidation of water or epoxidation of olefins (e.g. the preparation of propylene oxide from propylene and $H_2O_2$, the hydroxylation of aromatics, the preparation of hydroquinone from phenol and $H_2O_2$, and the conversion of toluene into cresol); the conversion of alkanes into alcohols, aldehydes and acids; isomerization reactions, for example the conversion of epoxides into aldehydes, and reductions, such as the conversion of $CO_2$ to methanol.

The following examples are intended to illustrate but not limit the disclosure. While they are typical of those that might be used, other procedures known to those skilled in the art may alternatively be used (see, e.g., Zhao et al., J. Am. Chem. Soc. 2015, 137, 2199-2202; the disclosure of which is incorporated herein for all purposes).

EXAMPLES

Materials for MOFs:

All reagents unless otherwise stated were obtained from commercial sources (Sigma-Aldrich, and Merck) and were used without further purification. Specifically, terephthalic acid (benzene-1,4-dicarboxylic acid or $BDCH_2$), 4,4'-biphenyldicarboxylic acid ($BPDCH_2$), (2,2'-bipyridine)-5,5'-dicarboxylic acid ($BPYDCH_2$), $ZrCl_4$, and N,N-dimethylformamide (DMF), were purchased from Sigma-Aldrich. Hexane, ethanol, acetone and distilled water were purchased from Merck.

Reaction Conditions to Produce MOFs of Uniform Size and Orientation:

The MOF heterolites can be synthesized using a MOF nanocrystal reaction mixture comprising metal ions having distinct and different coordination geometries in combination with ligands having multidentate functional groups and a suitable modulating agent in a suitable solvent system. It should be understood that ligands having multidentate functional groups can also bring with them corresponding counter cations, such as $H^+$, $Na^+$, $K^+$, $Mg^{2+}$, $Ca^{2+}$, $Sr^{2+}$; ammonium ions, such as alkyl-substituted ammonium ions, aryl-substituted ammonium ions; counter ions such as $F^-$, $Cl^-$, $Br^-$, $I^-$, $ClO^-$, $ClO^{2-}$, $ClO^{3-}$, $ClO^{4-}$, $OH^-$, $NO^{3-}$, $NO^{2-}$, $SO^{3-}$, $PO^{3-}$, $CO^{3-}$, and $PF^{6-}$; and organic counter ions such as acetate, $CH_3CO^{2-}$, and triflates $CF_3SO^{3-}$.

Examples of metal ions that can use to prepare the heterolites include, but are not limited to, $Mg^{2+}$, $Ca^{2+}$, $Ba^{2+}$, $Y^{3+}$, $Ti^{4+}$, $Zr^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{3+}$, $Ru^{3+}$, $Ru^{2+}$, $Os^{3+}$, $Os^{2+}$, $Co^{3+}$, $Co^{2+}$, $Rh^{3+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Ti^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^+$, $Sb^{3+}$, $Sb^+$, $Bi^{5+}$, $Bi^{3+}$, and Bit, along with the corresponding metal salt counterion.

The preparation of microporous MOF materials can be carried out in either an aqueous or non-aqueous system. The solvent may be polar or nonpolar as the case may be. Examples of non-aqueous solvents include n-alkanes, such as pentane, hexane, benzene, toluene, xylene, chlorobenzene, nitrobenzene, cyanobenzene, aniline, naphthalene, naphthas; alcohols, such as methanol, ethanol, n-propanol, and isopropanol; acetone; dichloromethane; methylene chloride; chloroform; carbon tetrachloride; tetrahydrofuran; dimethylformamide; dimethylsulfoxide; N-methylpyrollidone; dimethylacetamide; diethylformamide; thiophene; pyridine; ethanolamine; triethylamine; ethylenediamine; and the like. Those skilled in the art would readily be able to determine an appropriate solvent based on the starting reactants.

In order to control the nucleation and growth of the crystals, the reaction mixture should contain one or more modulating agents. The modulating agent should suppress the reaction at the initial point thereby enabling mass nucleation and growth to occur at the same time. Any modulating agent known to affect the outcome of the reaction, such as formic acid, acetic acid, hydrochloric acid, propionic acid, heptanoic acid, oleic acid can be used.

MOF Nanocrystal Synthesis:

The MOF nanocrystal crystallizing step is carried out by: leaving the MOF nanocrystal reaction mixture at room temperature or in an isothermal oven for up to 200° C.;

adding a diluted base to the solution to initiate crystallization; and/or transferring the reaction mixture to a closed vessel and heating to a predetermined temperature to allow for crystal formation.

Preparing a Colloidal Solution of MOF Nanocrystals:

The preparation of MOF heterolites is carried from a colloidal solution comprising MOF nanocrystals. When interactions between the surface of MOF nanocrystals and solvent prevent the suspension of the MOF nanocrystals in a colloidal solution, then a surfactant can be used. Any surfactant having long molecular chains or a polymer structure can be used, such as polyvinylpyrrolidone, sodium dodecyl sulfate, cetrimonium bromide and triton X-100. In the subsequent sedimentation step, the use of the surfactant can also control sedimentation velocity.

Assembly of MOF Nanocrystals into MOF Heterolites:

Assembly of MOF nanocrystals into a MOF heterolite is facilitated by either using accelerated sedimentation in a centrifuge; or gravimetric sedimentation in a pipette assembly. After completing sedimentation, the supernatant is removed and the MOF heterolite is dried under a low rate vacuum.

X-Ray Diffraction Analysis:

X-ray diffraction (SXRD) data are typically collected on a Bruker D8-Venture diffractometer equipped with Mo— ($\lambda$=0.71073 Å) and Cu-target ($\lambda$=1.54184 Å) micro-focus X-ray tubes and a PHOTON 100 CMOS detector, unless indicated otherwise. Additional data is collected using synchrotron radiation in the beamline 11.3.1 of the Advanced Light Source, LBNL.

Powder X-ray diffraction patterns (PXRD) are recorded using a Bruker D8 Advance diffractometer (Gobel-mirror monochromated Cu K$\alpha$ radiation $\lambda$=1.54056 Å). Room-temperature neutron powder diffraction data are collected on the high-resolution neutron powder diffractometer, BT1, using a Ge(311) monochromator ($\lambda$=2.0781 Å) and a 60 minute collimator.

Nuclear Magnetic Resonance (NMR) and Elemental Microanalysis (EA):

Solution $^1$H NMR spectra are acquired on a Bruker AVB-400 NMR spectrometer. EA are performed using a Perkin Elmer 2400 Series II CHNS elemental analyzer. Attenuated total reflectance (ATR) FTIR spectra of neat samples are performed using a Bruker ALPHA Platinum ATR-FTIR Spectrometer equipped with a single reflection diamond ATR module.

Thermal Gravimetric Analysis:

TGA curves are recorded on a TA Q500 thermal analysis system under air flow.

Isotherm Analysis:

Low-pressure gas ($N_2$ and Ar) adsorption isotherms are recorded using a Quantachrome Autosorb-1 volumetric gas adsorption analyzer. Liquid nitrogen and argon baths are used for the measurements at 77 and 87 K, respectively. Water isotherms are measured on a BEL Japan BELSORP-aqua3, and the water uptake in weight percent (wt %) unit is calculated as [(adsorbed amount of water)/(amount of adsorbent)×100], consistent with the established procedures. Prior to the water adsorption measurements, water (analyte) are flash frozen under liquid nitrogen and then evacuated under dynamic vacuum at least five times to remove any gases in the water reservoir. The measurement temperature is controlled with a water circulator. Helium is used for the estimation of dead space for gas and water adsorption measurements. Ultra-high-purity grade $N_2$, Ar, and He gases (Praxair, 99.999% purity) are used throughout the experiments.

Figure 24:
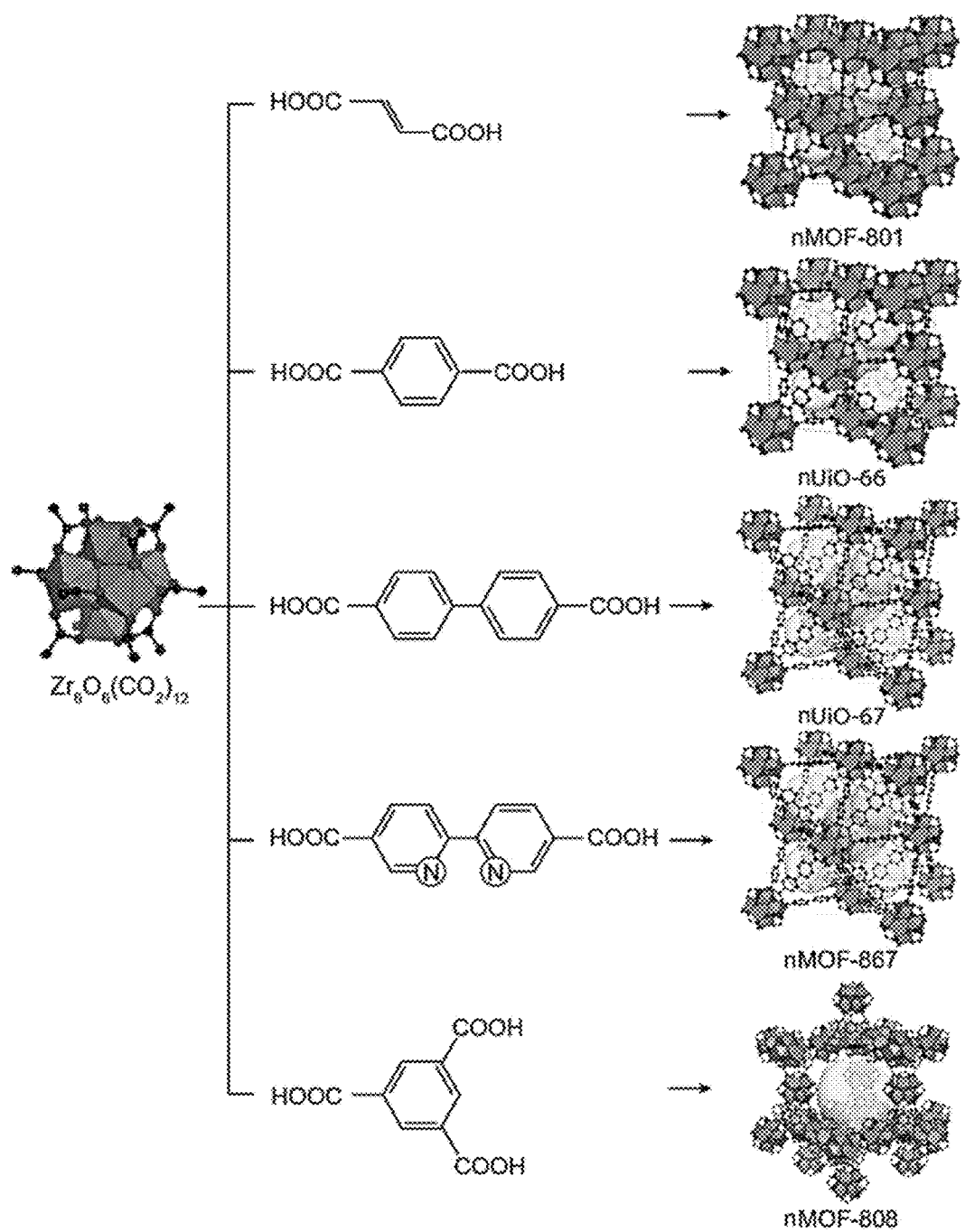
FIG. 24 shows reaction schemes for the synthesis of various MOFs of the disclosure.

FIG. 24 depicts a scheme for synthesis of various nMOFs of the disclosure.

MOF-801, $Zr_6O_4(OH)_4$ (Fumarate)$_6$:

36 mg of fumaric acid and 30 µL of triethylamine were dissolved in 5 mL of DMF while 66.8 mg of $ZrCl_4$ and 0.69 mL of acetic acid were dissolved in 5 mL of DMF separately. The solutions of fumaric acid and $ZrCl_4$ were combined in a 20 mL vial, capped, and placed in 85° C. oven for a day. The resulting MOF-801 was washed three times with DMF using a centrifuge (4,400 rpm for 20 min) and sonication and then sequentially immersed in methanol for three 24 h periods. Finally, MOF-801 was activated by removing the solvent under vacuum for 12 hrs at room temperature.

MOF-801-L, $Zr_6O_4(OH)_4$ (Fumarate)$_6$:

36 mg of fumaric acid and 30 µL of triethylamine were dissolved in 5 mL of DMF, while 66.8 mg of $ZrCl_4$ was dissolved in 5 mL of DMF separately. The solutions of fumaric acid and $ZrCl_4$ were combined in 20 mL vial, capped and placed in 85° C. oven for a day. The resulting MOF-801L was washed three times with DMF using a centrifuge (4,400 rpm for 20 min) and sonication and then sequentially immersed in methanol for three 24 h periods. Finally, MOF-801L was activated by removing the solvent under vacuum for 12 hrs at room temperature.

Uio-66, $Zr_6O_4(OH)_4$ (BDC)$_6$:

49.8 mg of $BDCH_2$ and 30 µL of triethylamine were dissolved in 5 mL of DMF while 66.8 mg of $ZrCl_4$ and 1.38 mL of acetic acid were dissolved in 5 mL of DMF separately. The solutions of terephthalic acid and $ZrCl_4$ were combined in 20 mL vial, capped and placed in 85° C. oven for a day. The resulting UiO-66 was washed three times with DMF using a centrifuge (4,400 rpm for 20 min) and sonication, and then sequentially immersed in methanol for three 24 h periods. Finally, UiO-66 was activated by removing the solvent under vacuum for 12 hrs at room temperature.

Uio-67, $Zr_6O_4(OH)_4$ (BPDC)$_6$ (BPDC=4,4'-Biphenyldicarboxylate):

19.36 mg of $BPDCH_2$ and 120 µL of triethylamine were dissolved in 5 mL of DMF while 18.64 mg of $ZrCl_4$ and 1.38 mL of acetic acid were dissolved in 5 mL of DMF separately. The solutions of 4 4'-biphenyldicarboxylic acid and $ZrCl_4$ were combined in 20 mL vial, capped and placed in 85° C. oven for a day. The resulting UiO-67 was washed three times with DMF using a centrifuge (4,400 rpm for 20 min) and sonication, and then sequentially immersed in methanol for three 24 h periods. Finally, UiO-67 was activated by removing the solvent under vacuum for 12 hrs at room temperature.

MOF-867, $Zr_6O_4(OH)_4$ (BPYDC)$_6$ (BPYDC=2,2'-Bipyridine-5,5'-Dicarboxylate):

19.5 mg of $BPYDCH_2$ and 30 µL of triethylamine were dissolved in 5 mL of DMF while 18.64 mg of $ZrCl_4$ and 1.38 mL of acetic acid were dissolved in 5 mL of DMF separately. The solutions of (2,2'-bipyridine)-5,5'-dicarboxylic acid and $ZrCl_4$ were combined in 20 mL vial, capped, and placed in 85° C. oven for a day. The resulting MOF-867 was washed three times with DMF using a centrifuge (4,400 rpm for 20 min) and sonication, and then sequentially immersed in methanol for three 24 h periods. Finally, MOF-867 was activated by removing the solvent under vacuum for 12 hrs at room temperature.

MOF-808, $Zr_6O_4(OH)_4$ (BTC)$_2$ (HCOO)$_6$ (BTC=1,3,5-Benzenetricarboxylate):

0.21 mg of $BTCH_3$ and 0.97 mg of $ZrOCl_2.8H_2O$ dissolved in a solvent mixture of 30 mL of DMF and 30 mL of formic acid were placed in a 125 mL screw-capped glass jar and placed in a 100° C. oven for a day. White powder was collected by filtration and washed with fresh DMF and methanol. Finally, MOF-808 was activated by removing the solvent under vacuum for 12 hrs at room temperature.

Figure 25:
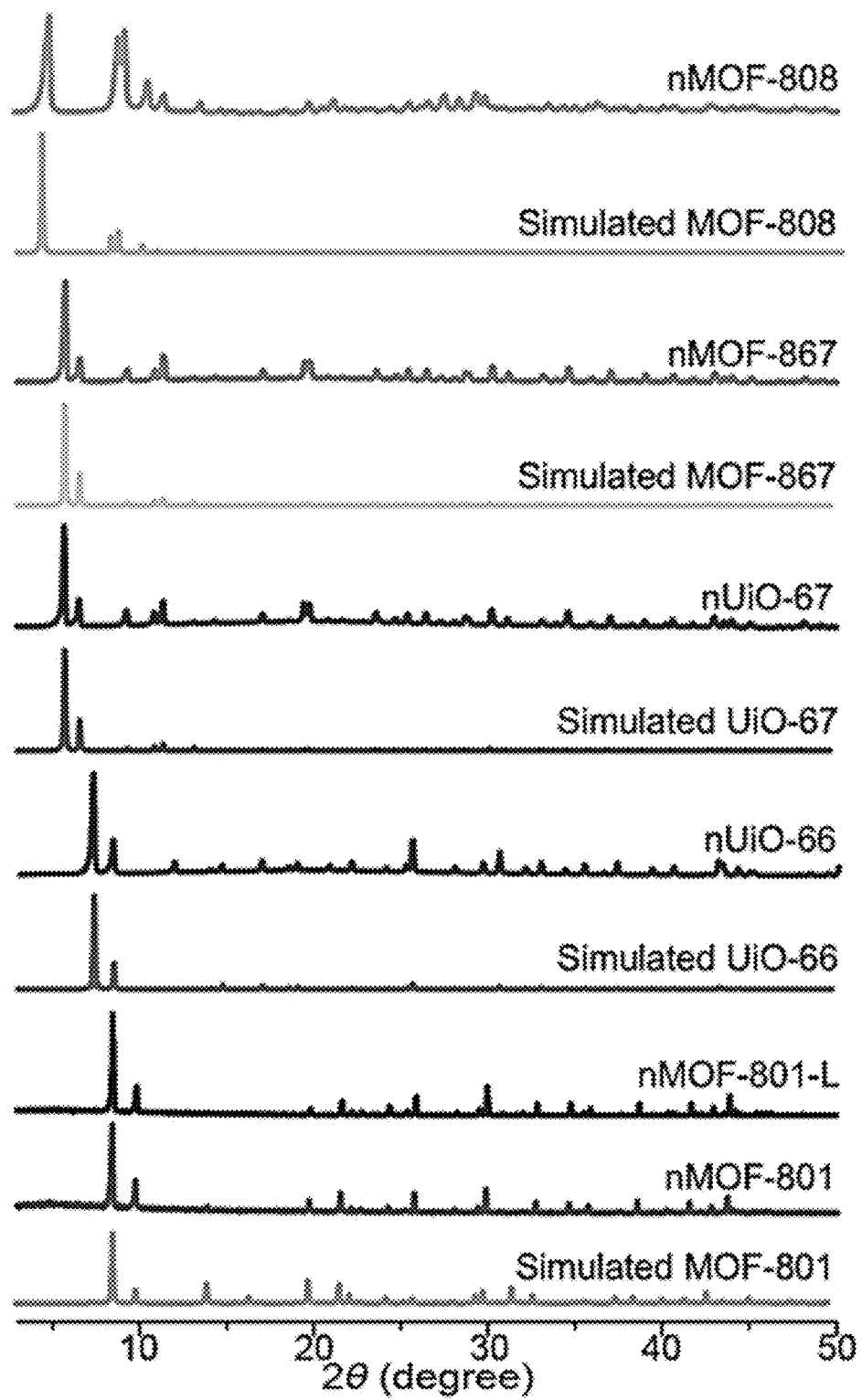
FIG. 25 shows PXRD patterns of simulated MOF-801, synthesized MOF-801, MOF-801-L, simulated UiO-66, synthesized UiO-66, simulated UiO-67, synthesized UiO-67, simulated MOF-867, synthesized MOF-867, simulated MOF-808, and synthesized MOF-808.
Figure 26:
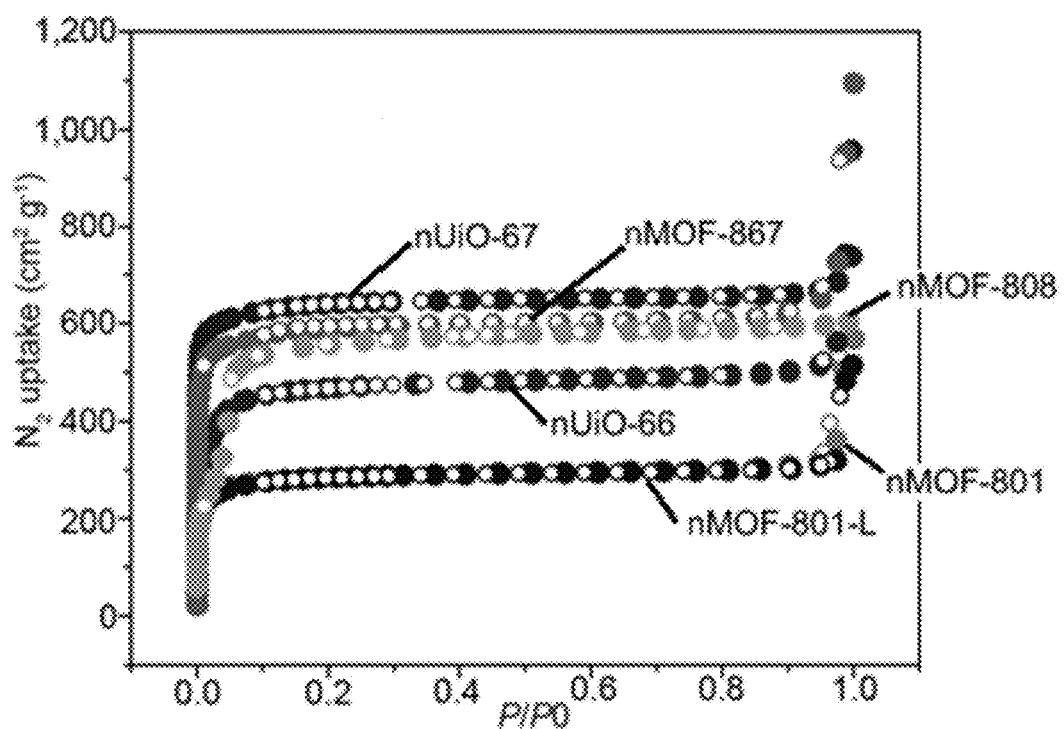
FIG. 26 shows nitrogen sorption isotherms for MOF-801, MOF-801-L, UiO-66, UiO-67, MOF-867, and MOF-808 measured at 77 K. Solid and open circles represent adsorption and desorption branches, respectively.

FIGS. 25 and 26 show the PXRD patters and nitrogen sorption of the nMOFs of the disclosure.

A number of embodiments have been described herein. Nevertheless, it will be understood that various modifications may be made without departing from the spirit and scope of this disclosure. Accordingly, other embodiments are within the scope of the following claims.

What is claimed is:

1. A mesoscopic material that is comprised of an ordered superlattice of a plurality of two to eight structurally different nano- or micro-porous metal-organic framework (MOF) nanocrystals, wherein the ordered superlattice comprises interlocking well-organized nanocrystals, and wherein the mesoscopic material exhibits chemical and physical properties that result from the interplay between nanoscopic MOF building blocks at the mesoscopic level.

2. The mesoscopic material of claim 1, wherein the plurality of MOF nanocrystals are comprised of a plurality of linked M-X-L units, wherein M is a metal, metal ion, or metal containing complex; X is an atom from an organic linking ligand that can form one or more bonds with M; and L is an organic linking ligand comprising an optionally substituted ($C_1$-$C_{20}$) alkyl, optionally substituted ($C_1$-$C_{20}$) alkenyl, optionally substituted ($C_1$-$C_{20}$) alkynyl, optionally substituted ($C_1$-$C_{20}$) hetero-alkyl, optionally substituted ($C_1$-$C_{20}$) hetero-alkenyl, optionally substituted ($C_1$-$C_{20}$) hetero-alkynyl, optionally substituted ($C_3$-$C_{12}$) cycloalkyl, optionally substituted ($C_3$-$C_{12}$) cycloalkenyl, optionally substituted aryl, optionally substituted heterocycle or optionally substituted mixed ring system, wherein the organic linking ligand comprises at least two or more carboxylate linking clusters.

3. The mesoscopic material of claim 2, wherein the organic linking ligand is selected from the group consisting of:

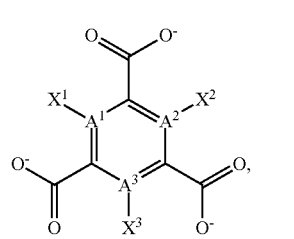
(I)

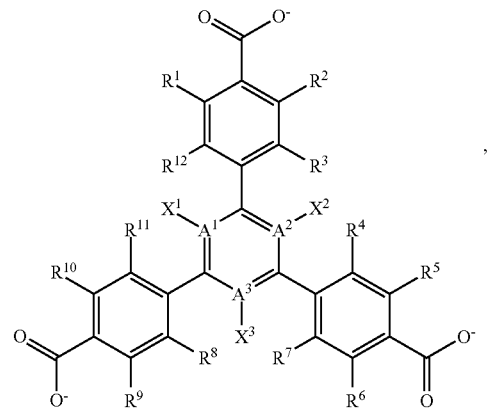
(II)

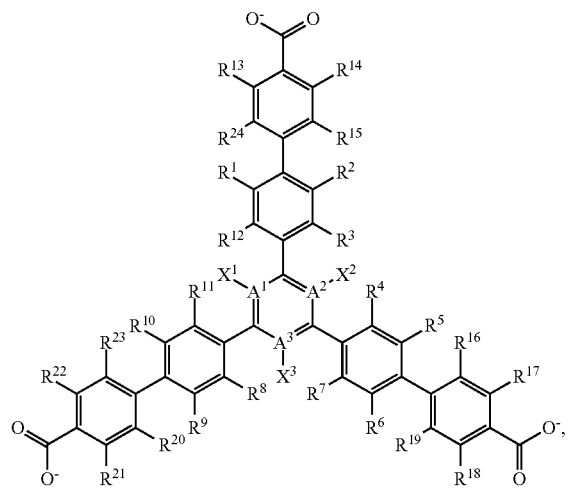
(III)

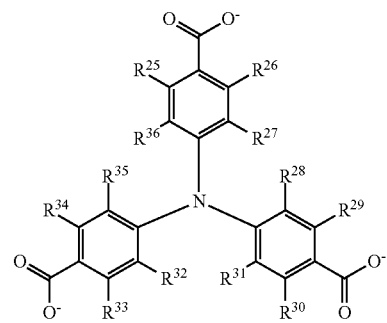
(IV)

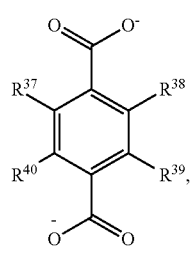
(V)

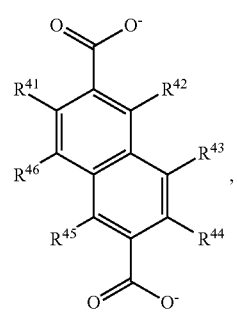
(VI)

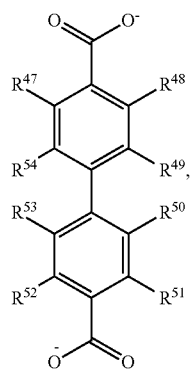
(VI)
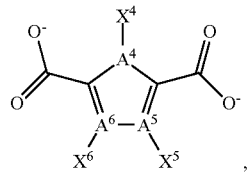
(VII)
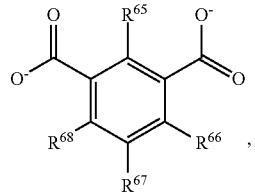
(VIII)
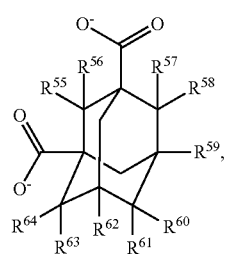
(IX)
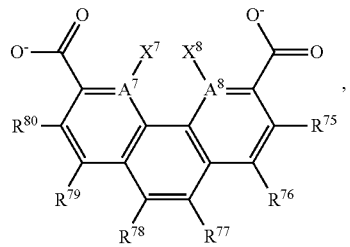
(X)
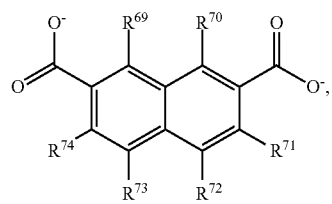
(XI)
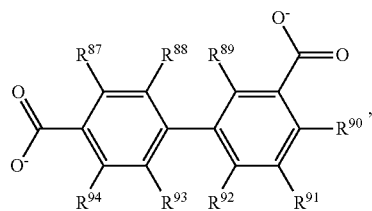
(XII)
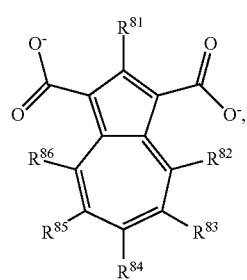
(XIII)
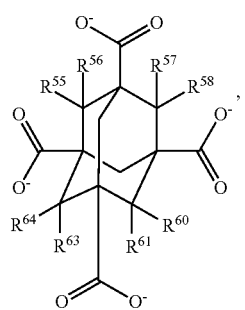
(XIV)
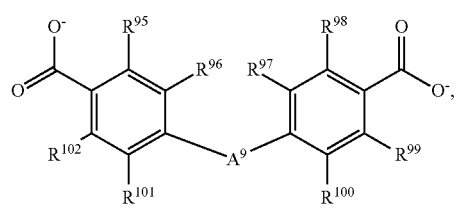
(XV)
(XVI)

-continued
(XVII)
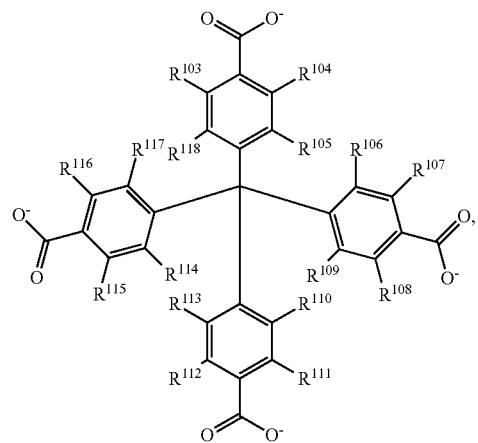
(XVIII)
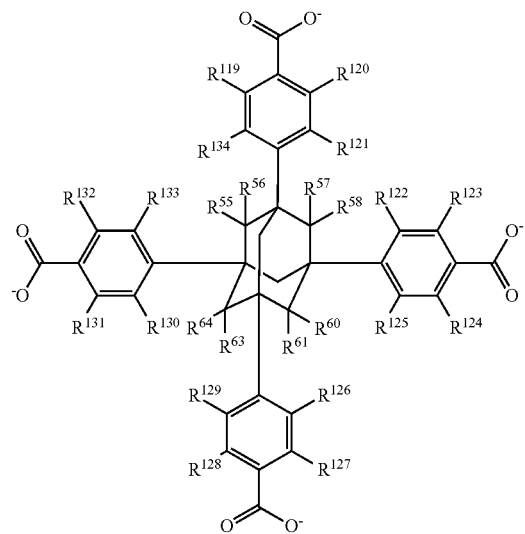
(XIX)
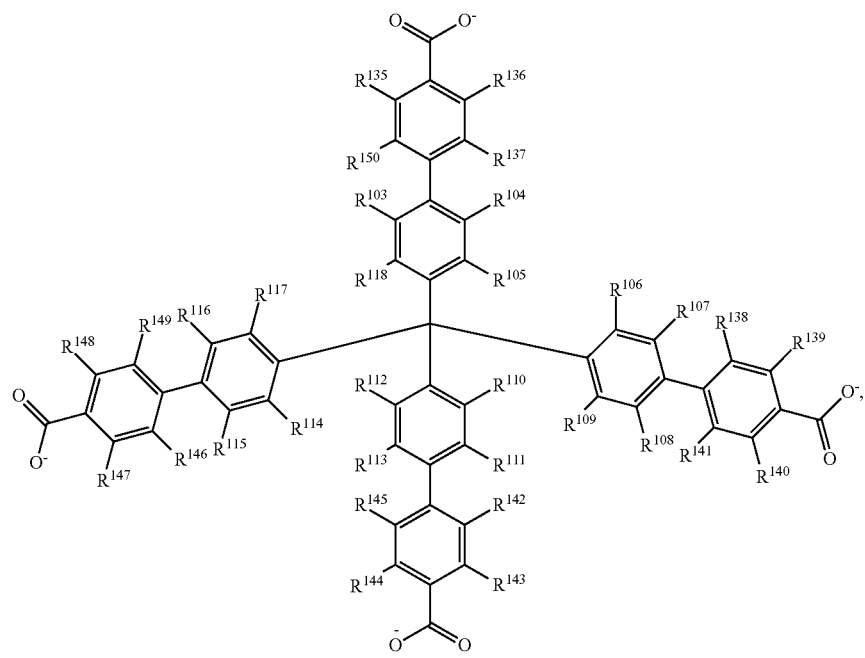

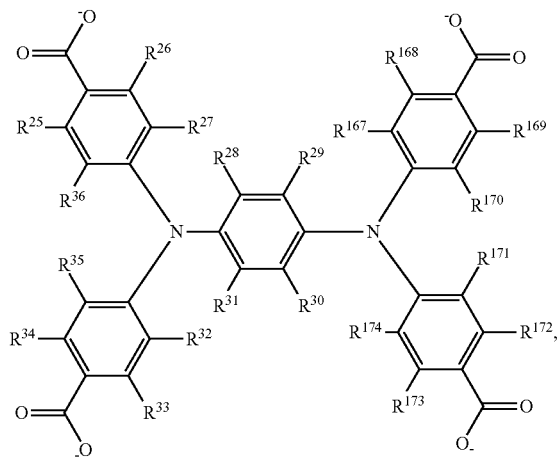
(XX)
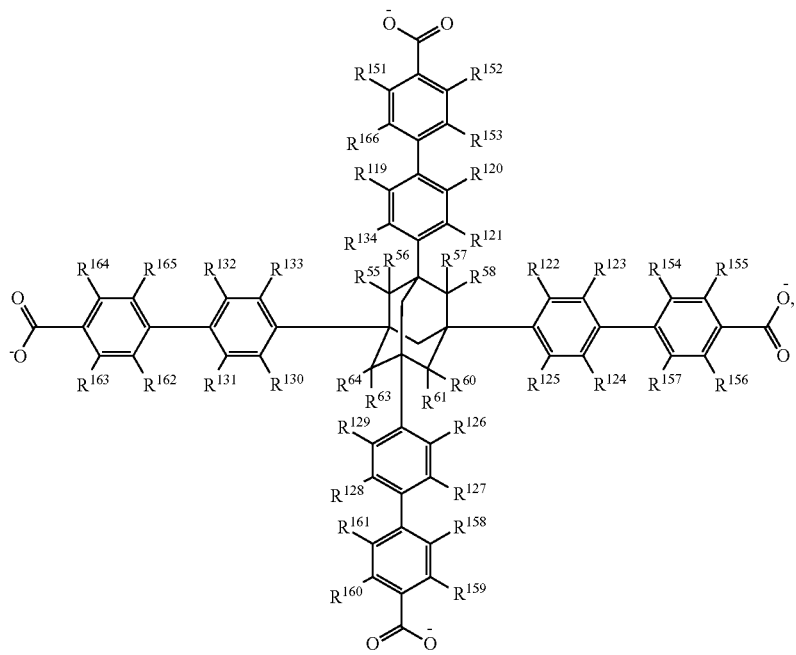
(XXI)
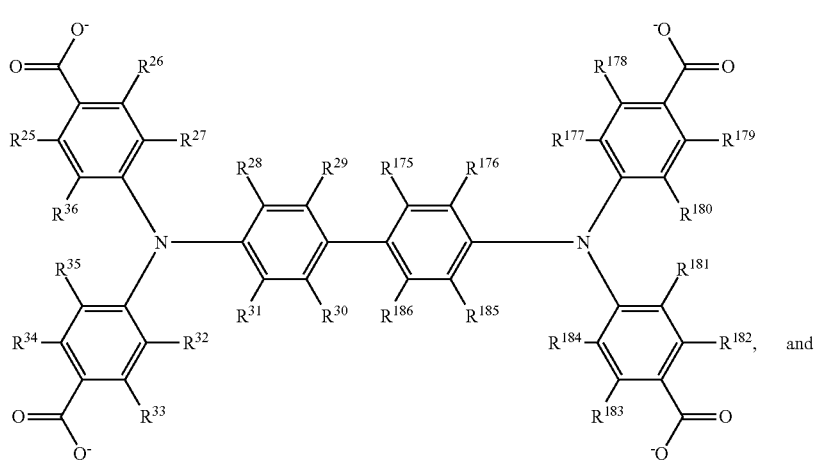
(XXII)

-continued

Formula XXIII

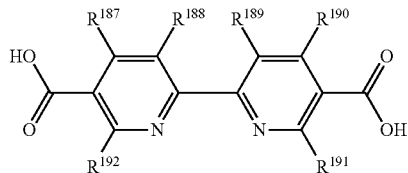

wherein the carboxylate groups depicted in formulas I-XXXIII form a bond with a metal, metal ion or metal complex, and wherein,
$A^1$-$A^8$ are independently a C, N, O, or S;
$A^9$ is selected from

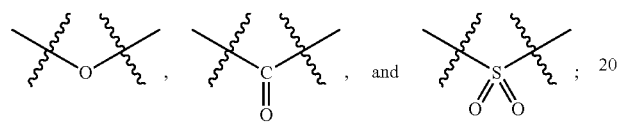

$X^1$-$X^8$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$) alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, and optionally substituted mixed ring system; and $R^1$-$R^{192}$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$) alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, and optionally substituted mixed ring system.

4. The mesoscopic material of claim 3, wherein the organic linking ligand comprises a structured selected from the group consisting of:

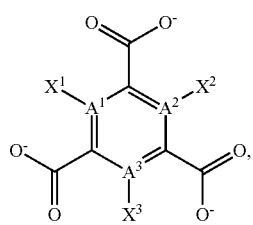

(I)

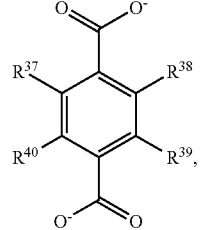

(V)

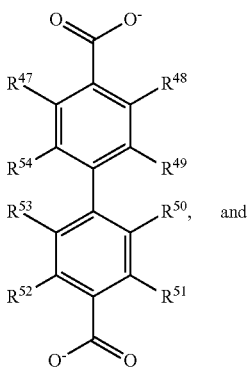

(VII)

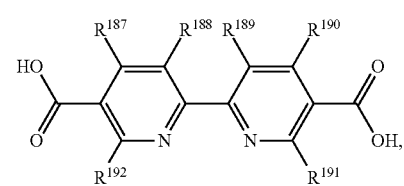

Formula XXIII wherein the carboxylate groups in Formula I, V, VII and XXIII undergo condensation with a metal, metal ion or metal complex, and wherein $A^1$-$A^3$ are independently a C, N, O, or S $X^1$-$X^3$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$) alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, and optionally substituted mixed ring system; and $R^{37}$-$R^{40}$, $R^{47}$-$R^{54}$, $R^{187}$-$R^{192}$ are independently selected from H, D, optionally substituted FG, optionally substituted ($C_1$-$C_{20}$)alkyl, optionally substituted ($C_1$-$C_{19}$) heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$) cycloalkyl, optionally substituted ($C_1$-$C_{19}$)cycloalkenyl, optionally substituted aryl, and optionally substituted heterocycle, optionally substituted mixed ring system.

5. The mesoscopic material of claim 3, wherein $R^1$-$R^{192}$ are independently selected from:

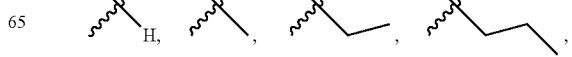

-continued

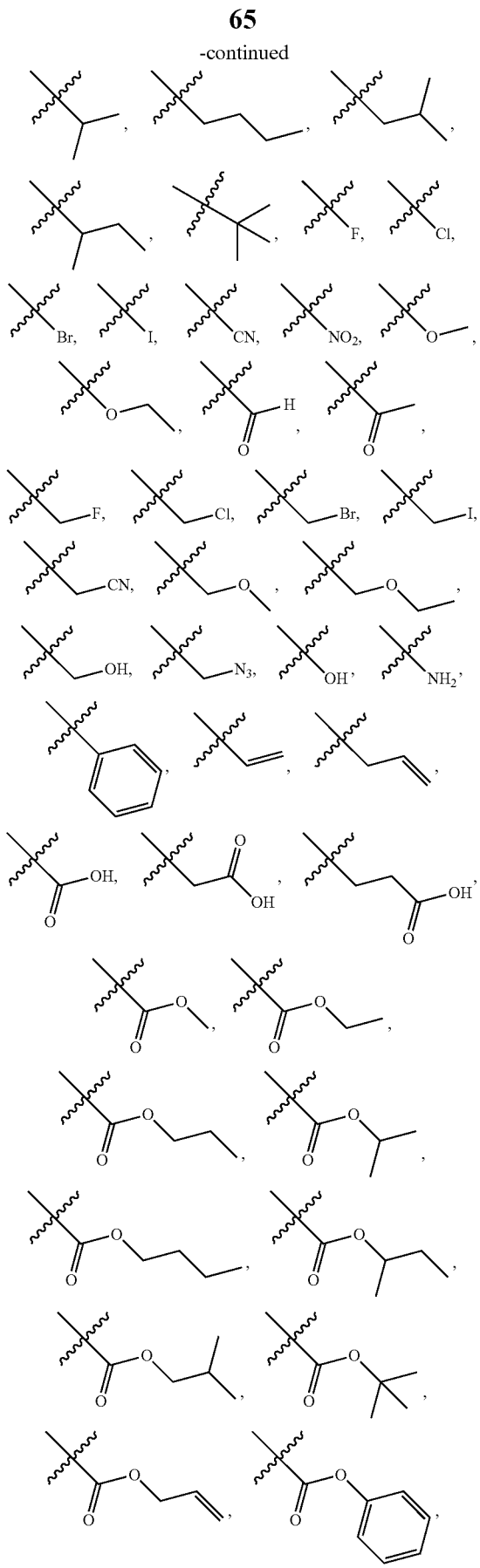

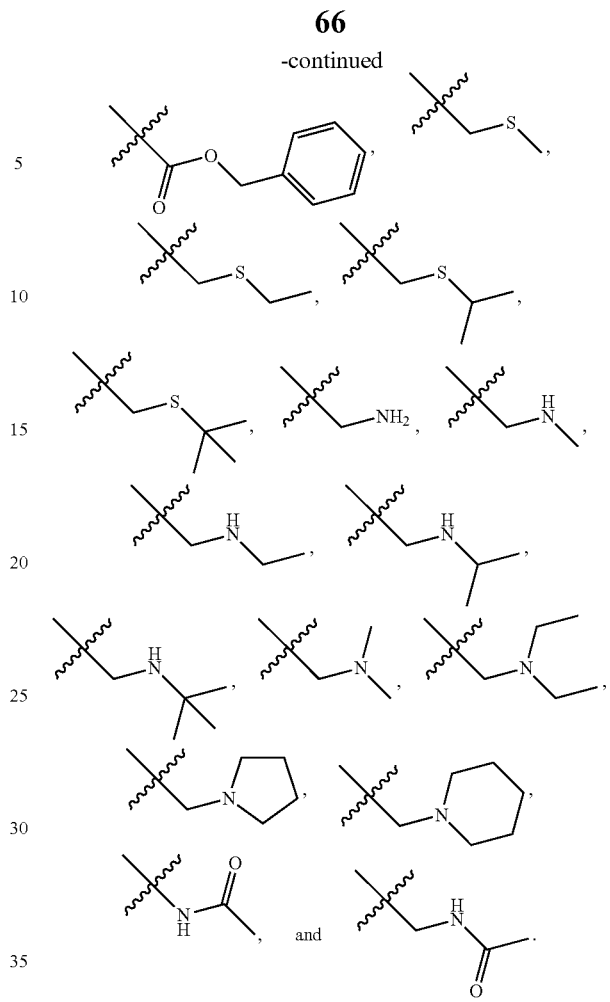

6. The mesoscopic material of claim 2, wherein M is a metal or metal ion selected from $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and combinations thereof, including any complexes which contain the metals or metal ions listed above, as well as any corresponding metal salt counter-anions.

7. The mesoscopic material of claim 1, wherein the ordered superlattice is comprised of a plurality of zirconium based MOF nanocrystals.

8. The mesoscopic material of claim 1, wherein the ordered superlattice is comprised of homogeneous MOF nanocrystals.

9. The mesoscopic material of claim 1, wherein the ordered superlattice is comprised of heterogeneous MOF nanocrystals.

10. The mesoscopic material of claim 1, wherein the structurally different MOFs have different gas sorption and/or gas separation properties.

11. The mesoscopic material of claim 1, wherein the structurally different MOFs have different catalytic properties.

12. The mesoscopic material of claim 10, wherein at least one MOF catalyzes the oxidation of water, and wherein at least one MOF catalyzes the reduction of carbon dioxide.

13. The mesoscopic material of claim 1, wherein the ordered superlattice is between 250 nm to 1500 nm in size.

14. The mesoscopic material of claim 13, wherein the mesoscopic material comprises the ordered superlattice that is between 500 nm to 1000 nm in size.

15. A method to produce the mesoscopic material of claim 1 comprising:

preparing a MOF reaction mixture comprising metal or metal ions, organic molecules comprising multidentate functional groups, a suitable modulating agent, and a suitable solvent system;

heating at a predetermined temperature and sufficient period of time to allow for crystal formation;

preparing a colloidal solution comprising the plurality of MOF nanocrystals;

assembling the plurality of MOF nanocrystals from the colloidal solution into a mesoscopic material by using accelerated sedimentation in a centrifuge or gravimetric sedimentation in a pipette assembly.

16. The method of claim 15, wherein a surfactant is added to colloidal solution.

17. The method of claim 16, wherein the surfactant is selected from polyvinylpyrrolidone, sodium dodecyl sulfate, cetrimonium bromide and triton X-100.

18. A device comprising the mesoscopic material of claim 1.

19. The device of claim 18, wherein the device is a gas separation and/or gas storage device.

20. The mesoscopic material of claim 1, wherein the plurality of MOF nanocrystals are substantially homogeneous in size.

* * * * *